(12) United States Patent
Menees

(10) Patent No.: US 9,771,577 B2
(45) Date of Patent: Sep. 26, 2017

(54) METHODS FOR ANALYZING LARIAT RNA

(71) Applicant: The Curators of the University of Missouri, Columbia, MO (US)

(72) Inventor: Thomas Matthew Menees, Overland Park, KS (US)

(73) Assignee: THE CURATORS OF THE UNIVERSITY OF MISSOURI UNIVERSITY OF MISSOURI, OFFICE OF IPA, Columbia, MO (US)

(*) Notice: Subject to any disclaimer, the term of this patent is extended or adjusted under 35 U.S.C. 154(b) by 232 days.

(21) Appl. No.: 14/520,392

(22) Filed: Oct. 22, 2014

(65) Prior Publication Data
US 2015/0141265 A1    May 21, 2015

Related U.S. Application Data

(63) Continuation of application No. 13/663,240, filed on Oct. 29, 2012, now abandoned.

(60) Provisional application No. 61/628,316, filed on Oct. 28, 2011.

(51) Int. Cl.
| | |
|---|---|
| C12N 15/10 | (2006.01) |
| C12N 9/16 | (2006.01) |
| C12N 9/22 | (2006.01) |
| C12N 9/24 | (2006.01) |
| C12N 9/44 | (2006.01) |
| C12P 19/34 | (2006.01) |

(52) U.S. Cl.
CPC .......... *C12N 15/1096* (2013.01); *C12N 9/16* (2013.01); *C12N 9/22* (2013.01); *C12N 9/24* (2013.01); *C12N 9/2457* (2013.01); *C12N 15/1093* (2013.01); *C12P 19/34* (2013.01)

(58) Field of Classification Search
None
See application file for complete search history.

(56) References Cited

U.S. PATENT DOCUMENTS

2009/0170711 A1    7/2009    Ellington et al.

OTHER PUBLICATIONS

Nam et al (1994) "Yeast Lariat Debranching Enzyme" Journal of Biological Chemistry 269(32):20613-20621.*
Altschul et al., "Basic Local Alignment Search Tool," J. Mol. Biol., 1990, vol. 215, pp. 403-410.
Altschul et al., "Gapped BLAST and PSI-BLAST: a new generation of protein database search programs," Nucleic Acids Research, 1997, vol. 25, No. 17, pp. 3389-3402.
Bartel et al., "Isolation of New Ribozymes from a Large Pool of Random Sequences," Science, 1993, New Series vol. 261, Issue 5127, pp. 1411-1418.

(Continued)

*Primary Examiner* — Karen S Weiler
(74) *Attorney, Agent, or Firm* — Polsinelli PC

(57) ABSTRACT

The present invention relates to compositions and methods useful for analyzing lariat RNA, which plays a role in the regulation of gene expression. A sample of RNA is specifically treated to remove linear mRNA and enrich for lariat RNA. The enriched lariat RNA sample may be analyzed further to identify introns, branch point sequences, alternative splicing patters, and gene transcription levels. The enriched lariat RNA sample may also be exploited as a detection or compound screening tool, as well as other uses.

13 Claims, 14 Drawing Sheets

(56) References Cited

OTHER PUBLICATIONS

Gray et al., "Mouse Brain Organization Revealed Through Direct Genome-Scale TF Expression Analysis," Science, 2004, vol. 306, pp. 2255-2257.
Helene et al., "Control of Gene Expression by Triple Helix-Forming Oligonucleotides," Annals New York Academy of Sciences, 1992, vol. 660, pp. 27-36.
Kaiser et al., "A Human Ubiquitin-conjugating Enzyme Homologous to Yeast UBC8," The Journal of Biological Chemistry, 1994, vol. 269, No. 12, pp. 8797-8802.
Karlin et al., "Methods for assessing the statistical significance of molecular sequence features by using general scoring schemes," Proc. Natl. Acad. Sci. USA, 1990, vol. 87, pp. 2264-2268.
Karlin et al., "Applications and statistics for multiple high-scoring segments in molecular sequences," Proc. Natl. Acad. Sci. USA, 1993, vol. 90, pp. 5873-5877.
Khalid et al., "Structure-function analysis of yeast RNA debranching enzyme (Dbr1), a manganese-dependent phosphodiesterase," Nucleic Acids Research, 2005, vol. 33, No. 19, pp. 6349-6360.
Martin et al., "Prp43 Is an Essential RNA-dependent ATPase Required for Release of Lariat-Intron from the Spliceosome," The Journal of Biological Chemistry, 2002, vol. 277, No. 20, pp. 17743-17750.
Schmittgen et al., "Analyzing real-time PCR data by the comparative CT method." Nature Protocols, 2008, vol. 3, No. 6, pp. 1101-1108.
Spingola et al., "Genome-wide bioinformatic and molecular analysis of introns in *Saccharomyces cerevisiae*." RNA Journal, 1999, vol. 5, pp. 221-234.
Storici et al., "In vivo site-directed mutagenesis using oligonucleotides," Nature Biotechnology, 2001, vol. 19, pp. 773-776.
Suzuki et al., "Chariacterization of RNase R-digested cellular RNA source that consists of lariat and circular RNAs from pre-mRNA splicing." Nucleic Acids Research, 2006, vol. 34, No. 8, pp. 1-7.
Ahern, "Boichemical, Reagents Kits Offer Scientist Good Return on Investment," The Scientist, 1995, vol. 9, No. 15.
Office Action related to U.S. Appl. No. 13/663,240 dated Apr. 22, 2014, 19 pages.

\* cited by examiner

FIG. 14

| | | | | |
|---|---|---|---|---|
| MTKLRIAVQ  | CC GQLNQIY | KEVSRIHAKT | PIDLLILILG  | FQSIRDGQDE | KSIAIPEKYQ | 60 |
| RLGDFISYYN | NEIEAPVPTI | FIGGN ESMR | HLMLLPHGGY | VAKNIFYMGY | SNVIWENGIR | 120 |
| IGSLSGIWKE | WDENKQRPDW | NDLENNNWKA | NIRNLYHVRI | SDIAPLFMIK | HRIDIMLS D | 180 |
| WPNGVVYHGD | TKHLLKLKPF | FEQDIKEGKL | GSPVTWQLLR | DLRPQWWLSA | L VREMASI | 240 |
| KHNKRSHEPP | NKSTSKTKKN | NNEIDLDLSS | DEDERSGIMN | CQEENEYDSK | YGETRFLALD | 300 |
| KCLPRRRWLE | ILEIEPDTSH | ASWKDENHRM | FWDPEFINNL | VICQKNKNLL | SNKPFNSVNW | 360 |
| IELSQSNREE | GRDIDWENYA | IPAYTLDIQK | DEVRQTKAFI | SKFMT | | 405 |

METHODS FOR ANALYZING LARIAT RNA

CROSS REFERENCE TO RELATED APPLICATIONS

This application is a continuation of U.S. non-provisional application Ser. No. 13/663,240, filed Oct. 29, 2012, which claims the priority of U.S. provisional application No. 61/628,316, filed Oct. 28, 2011, each of which is hereby incorporated by reference in its entirety.

FIELD OF THE INVENTION

The present invention relates to compositions, methods, and kits for analyzing lariat RNA. In particular, the invention relates to enriching an RNA population for lariat RNA and then analyzing the lariat RNA population.

BACKGROUND OF THE INVENTION

Pre-mRNA introns play an important role in the regulation of gene expression for many eukaryotes because their presence allows for the occurrence of alternative splicing. Such alternative splicing results in the creation of multiple proteins from a single gene, many of which are expressed in cell- or tissue-specific patterns. The pre-mRNA introns are excised in a lariat conformation to produce mRNA. Following excision, the 3' tails of the lariats are subject to exonucleolytic degradation up to the lariat branch point. The predominant pathway for further exonucleolytic degradation requires cleavage of the 2'-5' bond located at the branch point. This cleavage event occurs via a RNA debranching enzyme, a 2'-5' phosphodiesterase.

Although intron RNA sequences contain information necessary for their removal from pre-mRNAs, some introns contain additional information. In most eukaryotes microRNAs (miRNAs) and small nucleolar RNAs (snoRNAs) are encoded within introns. In studies with human cells it has been found that the vast majority of intronic miRNAs are excised from pre-mRNAs. Intronic snoRNAs, on the other hand, are processed from excised introns, as determined in baker's yeast, humans, and other eukaryotes.

Debranching and subsequent degradation of most intron RNAs are rapid, resulting in low steady state levels of intron RNAs relative levels of the corresponding mRNAs. The exceptions are intron sequences corresponding to RNAs with additional functions (e.g. snoRNAs). Studies in many different organisms have determined that cleavage of the 2'-5' bond by an RNA debranching enzyme is important for the maturation of intron-encoded snoRNAs and mirtrons, which is another class of miRNAs that are processed from excised introns.

Genome-wide studies analyzing excised intron RNAs in fruit flies and yeast have identified new introns and alternative splicing patterns. These analyses relied on creating cell populations that accumulate excised intron RNAs at elevated levels due to either mutation of the gene encoding debranching enzyme or knock down of debranching enzyme expression with siRNA. Analysis of RNA samples with elevated levels of RNA lariats increases the detectability of rare splicing variants. Cells defective for RNA debranching activity accumulate excised introns in their lariat forms with shorted 3' tails. Without the full length 3' tail, information for the 3' intron-exon junction is not obtainable from the intron lariat RNA sequences. However, studies have shown that the positions of RNA branch points may be deduced from analyzing intron RNA lariats. Direct information on branch points is only obtainable from analysis of RNA lariats. Therefore, there is a need to provide new compositions and methods for the analysis of RNA lariats that allow analysis of rare splicing variants and branch point sequences.

REFERENCE TO COLOR FIGURES

The application file contains at least one photograph executed in color. Copies of this patent application publication with color photographs will be provided by the Office upon request and payment of the necessary fee. The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows the annealing positions of primers for RT-PCR detection of ACT1 gene intron lariat RNA and mRNA. The intron lariat RNA is detected using primers oligo 146 and oligo 363 (depicted by arrows within the intron lariat RNA loop). The linear mRNA is detected using primers oliog 215 and oligo 216 (depicted by small arrows below the mRNA arrow).

FIG. 2A shows an agarose gel analysis of RT-PCRs for ACT1 intron lariat RNA following a series of enzyme treatments (PNPase) at decreasing amounts (indicated by the wedge at the tope of the gel image, highest amount of enzyme used in lane 1 and lowest in lane 7). RT-PCRs for ACT1 intron lariat RNA were performed with primers 146 and 363 (see FIG. 1A) and run for 15 cycles after the touchdown phase of the reaction.

FIG. 3A shows primer pairs for amplifying different segments along the length of FLO8 mRNA: 1/2=primers 372 and 373; 3/4=primers 374 and 375; 5/6=primers 376 and 377; 7/8=primers 378/and 379; 9/10=primers 380 and 381; 11/12=primers 382 and 383. FIG. 3B shows a PAGE analysis of RT-PCRs for FLO8 mRNA segments following enzyme treatment (PNPase, + lanes) and mock treatment (− lanes) of a total cellular RNA sample that had been pretreated with DNase I. Lanes containing the various FLO8 RT-PCRs are indicated below the gel image; the FLO8 primer pairs are indicated above the gel image. RT-PCRs for ACT1 RNAs are in the four lanes under the ACT1 title and serve as controls that indicate the PNPase reactions preceded as expected. The RT-PCRs for ACT1 mRNA and intron RNA are indicated below the corresponding lanes. These reactions used primer pairs 215/216 and 146/363, respectively. The lane marked "M" contains a DNA molecular weight standard (50 base pair (bp) ladder). FIG. 3C shows a PAGE analysis of RT-PCRs as described for FIG. 3B except that the total cellular nucleic acid samples were not treated with DNase I prior to PNPase enzyme treatment and RT-PCRs. For all RT-PCRs in FIGS. 3B and 3C, reactions were performed with 24 cycles after the touchdown phase.

FIG. 4A shows the elution profile of histidine-tagged yeast Dbr1p, purified from *E. coli*, collected for 100 mM and 200 mM concentrations of imidazole. Dbr1p bound to a nickel-nitrilotriacetic acid (nickel-NTA) column was eluted with increasing concentrations of imidazole. Six, ~1.5 mL fractions were collected for each imidazole concentration. FIG. 4B shows the elution profile of histidine-tagged yeast Dbr1p collected for 300 mM and 500 mM concentrations of imidazole. Key: "M" is the protein molecular weight standard; and, 1-6 are the fractions collected from the nickel-nitrilotriacetic column. FIG. 4C shows the matrix-assisted laser desorption/ionization-time-of-flight (MALDI-TOF) mass spectrometry analysis to assess the molecular mass of the main elution product in fractions 2-6 of the 100 mM imidazole elution.

FIG. 5 shows an agarose gel analysis of RT-PCRs for ACT1 RNAs following treatment with Dbr1p (+ lanes) and mock treatment (− lanes) of total cellular RNA sample. Key: lanes 2 and 4 contain RT-PCRs for ACT1 intron lariat RNA; lanes 1 and 3 are RT-PCRs for ACT1 mRNA; lane M contains a DNA molecular weight standard (50 bp ladder). RT-PCRs for ACT1 intron lariat RNA were run for 19 cycles after the touchdown phase of the reaction; RT-PCRs for ACT1 mRNA were run for 24 cycles after the touchdown phase of the reaction.

FIG. 6A shows an agarose gel analysis of RT-PCRs for ACT1 RNAs following treatment of a total cellular RNA sample from a dbr1 strain with Dbr1p (+Dbr1p) and PNPase (+ PNPase) as well as mock treatment (− treatment). In this experiment, PNPase treatment preceded Dbr1p treatment for samples that were treated with both enzymes. Lanes 1, 3, 5, and 7 contain RT-PCRs for ACT1 mRNA of a total cellular RNA sample. Lanes 2, 4, 6, and 8 contain parallel RT-PCRs for ACT1 intron lariat RNA.

FIG. 7A shows the annealing positions of primers for RT-PCR detection of mRNA (FWDm primer and REVm primer) and intron lariat RNA species (FWDi primer and REVi primer). A TaqMan probe is designed to span the same exon-exon junction. The star and the triangle at opposite ends of the TaqMan probes represent the fluorescent reporter molecule and the quencher that are bound to the 5' and 3' ends, respectively. The TaqMan probes that anneal to a particular mRNA and lariat RNA pair contain different fluorescent reporter molecules, indicated by solid and stippled stars. Note that lariat RNA detection does not involve annealing of PCR primers or TaqMan probes across lariat branch points. FIG. 7B graphically illustrates the relative quantification of ACT1 intron lariat RNA in total RNA samples from different yeast strains. RQ, the relative quantification, is the ratio of intron RNA to mRNA for a particular sample relative to the ratio of intron RNA to mRNA for the DBR1 (wild-type) sample at the left end of the bar graph (which sets the RQ for DBR1 itself to 1). Quantification experiments were repeated three times and the qPCRs were performed in triplicate each time. The standard error bars display the calculated maximum (RQ-max) and minimum (RQMin) expression levels that represent standard error of the mean expression level (RQ value). FIG. 7C graphically illustrates the relative quantification of RPP1B intron lariat RNA for the same RNA samples presented in FIG. 7B. FIG. 7D graphically illustrates the relative quantification of YRA1 intron lariat RNA for the same RNA samples presented in FIG. 7B.

FIG. 13A shows chromosome 6 is depicted at the top, below which a 20 kilo-base pair (kbp) segment is highlighted (black bar), along with a detailed map of the genes that lie within this segment. Gene open reading frames (ORFs) are indicated by red or blue bars, depending on which DNA strand of the chromosome encodes the sense strand for each ORF (red for the upper strand, blue for the lower strand).

FIG. 14 shows the conserved amino acid conservation among RNA debranching enzymes using the sequence of *Saccharomyces cerevisiae* Dbr1 (405 total amino acid residues) (SEQ ID. NO: 47) as a representative example. (Key: green numbers=amino acid residue number of last amino acid in each line (out of 405 total amino acids residues); highlighted yellow=identical among all RNA debranching enzymes; red=conserved among all RNA debranching enzymes; blue=not conserved.

SUMMARY OF THE INVENTION

Figure 1A:
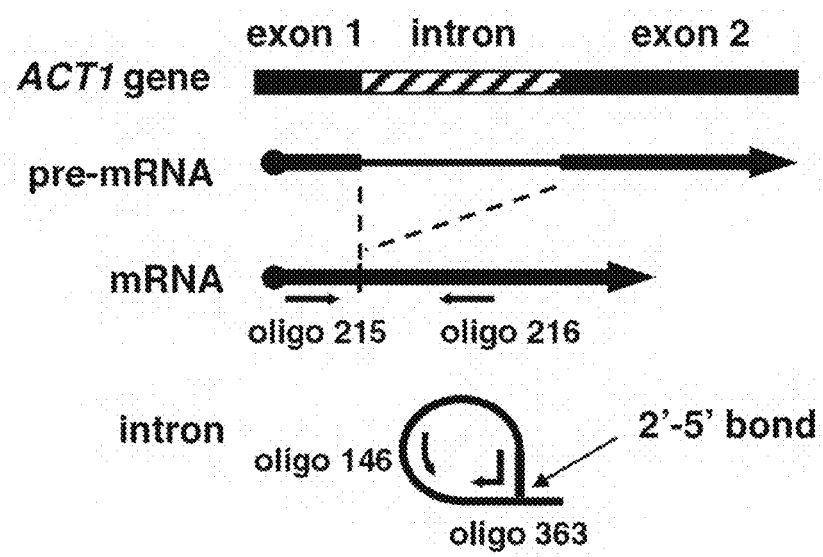
FIG. 1A,B illustrates reverse transcriptase polymerase chain reaction (RT-PCR) detection of lariat RNA.

The present invention is directed to compositions and methods for analyzing lariat RNA. The compositions of the invention include isolated enzymes and supportive buffers for efficient use of the isolated enzymes. The methods of the invention include methods of enriching an RNA population for lariat RNA and analyzing lariat RNA. The compositions and methods of the invention may be provided in a kit.

The enzymes of the invention include linear RNA degrading enzymes, 5' cap removing enzymes and debranching enzymes. Suitable linear RNA degrading enzymes include those capable of degrading linear RNA or mRNA. Such linear RNA degrading enzymes include, without limitation, exonucleases, 3' exonucleases, 5' exonucleases, those with both 5' and 3' exonuclease activity, those known in the art or yet to be discovered, and combinations thereof.

Suitable 5' cap removing enzymes include those capable of degrading or excising the 5' cap of linear RNA or mRNA. Such enzymes include those commonly known in the art, such as Dcp1 or Dcp2, as well as those yet to be discovered, and combinations thereof.

Suitable debranching enzymes include those capable of degrading, excising, or cleaving the 2'-5' bond at the branch point of lariat RNA. Such enzymes include 2'-5' phosphodiesterases, such as Dbr1, all those known in the art or yet to be discovered, and combinations thereof. Also, such enzymes include those encoding an amino acid sequence having at least 35% sequence identity to at least one of SEQ ID NOs: 46, 47, 48, 49, 50, 51, 52, 53, 54, 55, 56, 57, 58, 59, 60, 61, 62, 63, 64, 65, or 66. The sequence identity may be about 40, 45, 50, 55, 60, 65, 70, 75, 80, 81, 82, 83, 84, 85, 86, 87, 88, 89, 90, 91, 92, 93, 94, 95, 96, 97, 98, 99% or more. In another embodiment, the nucleic acid sequence may have at least 35% sequence identity to the metallophosphatase domain of at least one of SEQ ID NO: 46-66. The sequence identity may be about 40, 45, 50, 55, 60, 65, 70, 75, 80, 81, 82, 83, 84, 85, 86, 87, 88, 89, 90, 91, 92, 93, 94, 95, 96, 97, 98, 99% or more. In *S. cerevisiae* Dbr1 (SEQ ID NO: 47), the metallophosphatase domain is located at amino acid residues 6 to 238 (FIG. 14).

The invention also includes methods of enriching an RNA population for lariat RNA. Such methods include providing an RNA population and contacting the RNA population with a linear RNA degrading enzyme to form a lariat RNA enriched population. Suitable methods may further include contacting the RNA population with a debranching enzyme.

The invention also includes methods of analyzing the lariat RNA in an RNA sample or population. Such methods include providing an RNA population and contacting the RNA population with a linear RNA degrading enzyme to form a lariat RNA enriched population. The lariat RNA enriched population may be used to create a cDNA library. In one embodiment the cDNA library is created by reverse transcribing the lariat RNA enriched population. Methods known in the art for creating a cDNA library may be used. Suitable methods may also further include sequencing the cDNA library created using the lariat RNA enriched population.

The invention includes kits for practicing the methods of the invention. Suitable kits contain at least one linear RNA degrading enzyme and instructions. Kits may also include a linear RNA degrading enzyme buffer, debranching enzyme, debranching enzyme buffer, 5' decapping enzyme, 5' decapping enzyme buffer, and combinations thereof.

DESCRIPTION OF THE PREFERRED EMBODIMENTS

In accordance with the present invention, processes of comprehensively analyzing lariat RNA have been discovered. In particular, the present invention provides compositions, methods, and kits useful for analyzing lariat RNA. The compositions and methods are directed to enriching an RNA population for lariat RNA and analyzing the lariat RNA.

Various aspects of the invention are described in further detail in the following subsections.

I. Compositions

A. Enzymes

One aspect of the invention pertains to isolated enzymes that are used in the methods described herein. Suitable enzymes include those capable of degrading linear RNA, linearizing lariat RNA, removing the 5' cap from linear RNA (mRNA), or combinations thereof.

Enzymes capable of degrading linear RNA are used to remove the linear RNA from the RNA population, enriching the population for lariat RNA. Suitable linear RNA degrading enzymes include, without limitation, 3' exonucleases, 5' exonucleases, 5'/3' exonucleases, and combinations thereof. Any enzyme capable of degrading linear RNA is contemplated herein, as well as those not yet discovered. For example, the polynucleotide phosphorylases of *Bacillus stearothermophilus* (BsPNPase) and *Thermus thermophilus* (TtPNPase), as well as the RNase of *E. coli* (RNase R) are suitable linear RNA degrading enzymes.

Enzymes capable of removing the 5' cap from linear RNA or mRNA are used to allow linear RNA degrading enzymes to work, where the 5' cap may inhibit degradation. Suitable 5' cap removing enzymes include those capable of cleaving or degrading the 5' cap from linear RNA or mRNA. Any enzyme capable of 5' cap removal is contemplated herein, as well as those not yet discovered. For example, the 5' cap removing enzymes Dcp1 and Dcp2 are suitable for the invention. The invention also includes 5' cap removal treatments known in the art or yet to be discovered.

Enzymes capable of linearizing lariat RNA are debranching enzymes, which are used to unfold the lariat structure of the RNA to allow further analysis. Suitable debranching enzymes are those capable of cleaving the 2'-5' bond at the branch point of lariat RNA. Such debranching enzymes include, without limitation, debranching enzymes having sequence homology to SEQ ID NO: 46-66.

Preferably, the nucleic acid sequence of debranching enzymes have at least 35% sequence identity to the nucleic acid sequence that encodes the amino acid sequence of at least one of SEQ ID NO: 46, 47, 48, 49, 50, 51, 52, 53, 54, 55, 56, 57, 58, 59, 60, 61, 62, 63, 64, 65, or 66. The sequence identity may be about 40, 45, 50, 55, 60, 65, 70, 75, 80, 81, 82, 83, 84, 85, 86, 87, 88, 89, 90, 91, 92, 93, 94, 95, 96, 97, 98, 99% or more. In another embodiment, the nucleic acid sequence may have at least 35% sequence identity to the metallophosphatase domain of the nucleic acid sequence that encodes at least one of SEQ ID NO: 46, 47, 48, 49, 50, 51, 52, 53, 54, 55, 56, 57, 58, 59, 60, 61, 62, 63, 64, 65, or 66. The sequence identity may be about 40, 45, 50, 55, 60, 65, 70, 75, 80, 81, 82, 83, 84, 85, 86, 87, 88, 89, 90, 91, 92, 93, 94, 95, 96, 97, 98, 99% or more. In S. cerevisiae Dbr1 (SEQ ID NO: 47), the metallophosphatase domain is located at amino acid residues 6 to 238 (FIG. 14).

A nucleic acid molecule of the present invention, e.g., a nucleic acid molecule having the nucleotide sequence of SEQ ID NO: 46-66, or a complement of any of these nucleotide sequences, may be isolated using standard molecular biology techniques and the sequence information provided herein. Using all or portion of the nucleic acid sequences of SEQ ID NO:46-66, debranching enzyme nucleic acid molecules may be isolated using standard hybridization and cloning techniques (e.g., as described in Sambrook et al., eds., Molecular Cloning: A Laboratory Manual. 2nd. ed., Cold Spring Harbor Laboratory, Cold Spring Harbor Laboratory Press, Cold Spring Harbor, N.Y., 1989).

Accordingly, another aspect of the invention pertains to nucleic acid molecules encoding debranching enzymes that contain changes in amino acid residues that may or may not be essential for activity. Such debranching enzymes proteins differ in amino acid sequence from SEQ ID NO: 46-66. In one embodiment, the isolated nucleic acid molecule includes a nucleotide sequence encoding a protein that includes an amino acid sequence that is at least about 35%, 40%, 45%, 50%, 55%, 60%, 65%, 70%, 75%, 80%, 85%, 90%, 95%, 98% or more identical to the amino acid sequence of SEQ ID NO: 46-66. An isolated nucleic acid molecule encoding a debranching enzymes having a sequence which differs from that of SEQ ID NO: 46-66, may be created by introducing one or more nucleotide substitutions, additions or deletions into the nucleotide sequence of debranching enzymes (SEQ ID NO: 46-66) such that one or more amino acid substitutions, additions or deletions are introduced into the encoded protein. Mutations may be introduced by standard techniques known in the art, such as site-directed mutagenesis and PCR-mediated mutagenesis.

The present invention encompasses antisense nucleic acid molecules. Antisense molecules are complementary to a sense nucleic acid encoding a protein, complementary to the coding strand of a double-stranded cDNA molecule, or complementary to an mRNA sequence. Accordingly, an antisense nucleic acid hydrogen bonds to a sense nucleic acid. The antisense nucleic acid can be complementary to an entire debranching enzyme coding strand, or to only a portion thereof, such as all or part of the protein coding region (or open reading frame). An antisense nucleic acid molecule can be antisense to a non-coding region of the coding strand of a nucleotide sequence encoding a debranching enzyme. The non-coding regions ("5' and 3' untranslated regions") are the 5' and 3' sequences that flank the coding region and are not translated into amino acids. Given the coding strand sequences encoding debranching enzymes disclosed herein, antisense nucleic acids of the invention may be designed according to the rules of Watson and Crick base pairing. The antisense nucleic acid molecule may be complementary to the entire coding region of debranching enzyme mRNA, but more preferably is an oligonucleotide which is antisense to only a portion of the coding or non-coding region of a debranching enzyme mRNA. For example, the antisense oligonucleotide may be complementary to the region surrounding the translation start site of a debranching enzyme mRNA. An antisense oligonucleotide may be, for example, about 5, 10, 15, 20, 25, 30, 35, 40, 45 or 50 nucleotides in length. An antisense nucleic acid of the invention may be constructed using chemical synthesis and enzymatic ligation reactions using procedures known in the art. For example, an antisense nucleic acid (e.g., an antisense oligonucleotide) may be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which may be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid may be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are generated in situ such that they hybridize with or bind to cellular mRNA and/or genomic DNA encoding a debranching enzyme to thereby inhibit expression of the enzyme, e.g., by inhibiting transcription and/or translation. The hybridization may be by conventional nucleotide complementarity to form a stable duplex, or, for example, in the case of an antisense nucleic acid molecule which binds to DNA duplexes, through specific interactions in the major groove of the double helix.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) may be used to catalytically cleave debranching enzyme mRNA transcripts to thereby inhibit translation of debranching enzyme mRNA. A ribozyme having specificity for a debranching enzyme-encoding nucleic acid may be designed based upon the nucleotide sequence of the debranching enzyme cDNA. For example, debranching enzyme mRNA may be used to select a catalytic RNA having a specific ribonuclease activity from a pool of RNA molecules. See, e.g., Bartel and Szostak (1993) Science 261: 1411-1418.

The invention also encompasses nucleic acid molecules which form triple helical structures. For example, debranching enzyme gene expression may be inhibited by targeting nucleotide sequences complementary to the regulatory region of the debranching enzyme gene (e.g., promoter and/or enhancers) to form triple helical structures that prevent transcription of the debranching enzyme gene in target cells. See generally, Helene (1991) Anticancer Drug Des. 6(6):569-84; Helene (1992) Ann. N.Y. Acad. Sci. 660:27-36; and Maher (1992) Bioassays 14(12):807-15.

A useful debranching enzyme protein is a protein which includes an amino acid sequence at least about 45%, preferably 50%, 55%, 60%, 65%, 70%, 75%, 80%, 85%, 90%, 95%, 99% or more identical to the amino acid sequence of SEQ ID NO: 46-66, and retains the functional activity of a debranching protein of SEQ ID NO:46-66.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions.times.100).

The determination of percent homology between two sequences may be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences similar or homologous to nucleic acid sequences of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used.

One useful fusion protein is a fusion protein in which the debranching enzyme sequences are fused to tag or marker sequences. Such fusion proteins can facilitate the purification of recombinant debranching enzymes. Suitable tag and marker sequences are well known in the prior art and include all those known in the art or yet to be discovered. Exemplary tags or markers include, without limitation, HIS tag, GST, MYC tag, fluorescent proteins, flourophores, and others that are too numerous to include herein.

One skilled in the art will recognize that activity of enzymes depends upon conditions that are specific to each enzyme. Some enzymes are active at higher temperatures, such at 65° C., while others are active at lower temperatures, such at 37° C. Other conditions include pH and salt content. As such conditions depend upon the enzyme; the invention includes all conditions for which the enzymes useful for the invention are active.

II. Methods

The present invention includes methods of preparing and analyzing lariat RNA populations. Methods of the invention also include using the compositions described herein to modulate the proportion of lariat RNA in an RNA population.

Methods of preparing lariat RNA populations or enriched lariat RNA populations include providing an RNA population and contacting it with a linear RNA degrading enzyme to form a lariat RNA enriched population. In some embodiments, methods may further include contacting the RNA population with a debranching enzyme. The order with which the RNA population is contacted with the linear RNA degrading enzyme and debranching enzyme determines the composition of the resulting enriched RNA population. If the RNA population is contacted with the linear RNA degrading enzyme before the debranching enzyme, then the resulting enriched RNA population will be enriched for lariat RNA. If the RNA population is contacted with the debranching enzyme before the linear RNA degrading enzyme, then the resulting enriched RNA population will not be enriched for lariat RNA or linear RNA.

In some embodiments, methods may further include contacting the RNA population with a 5' cap removing enzyme or be subjected to a 5' cap removal treatment. Preferably, the 5' cap removing enzyme or treatment is contacted or used on the RNA population before the linear RNA degrading enzyme.

In some embodiments, methods may include inhibiting the RNA debranching enzyme in a population of cells prior to the methods of enriching for lariat RNA. Inhibiting the RNA debranching enzyme in a population of cells would allow the proportion of lariat RNA in a population of cells to increase, thereby allowing the enriched lariat RNA population to increase. The RNA debranching enzyme may be inhibited using methods known in the art. Such methods may include, without limitation, siRNA technology, ribozymes, knockout cell lines, knock down cell lines, and other methods known in the art.

The invention also includes methods of analyzing the lariat RNA in an RNA sample or population. In some embodiments, methods include providing an RNA population and contacting the RNA population with a linear RNA degrading enzyme to form a lariat RNA enriched population. The lariat RNA enriched population is contacted with a debranching enzyme and then subsequently with a linear RNA degrading enzyme to confirm true lariat RNAs are present.

In other embodiments, methods include providing an RNA population and contacting the RNA population with a linear RNA degrading enzyme to form a lariat RNA enriched population. The lariat RNA enriched population is then used to create a cDNA library. In one embodiment, the cDNA library is created by reverse transcribing the lariat RNA enriched population. Methods known in the art for creating a cDNA library may be used. Suitable methods may also further include sequencing the cDNA library created using the lariat RNA enriched population. Methods known in the art for sequencing may be used.

III. Kits

The present invention includes articles of manufacture and kits containing materials useful for preparing enriched lariat RNA populations as described herein. The article of manufacture may include a container of a composition as described herein with a label. Suitable containers include, for example, bottles, vials, and test tubes. The containers may be formed from a variety of materials such as glass or plastic.

In one embodiment, containers hold a composition having an active agent which is effective for degrading linear RNA or linearizing lariat RNA. The active agent may be an enzyme. Suitable enzymes include 3' exonucleases, 5' exonucleases, 5'/3' exonucleases, debranching enzymes, decapping enzymes, or combinations thereof. Active agents may be combined into a single container or provided in separate containers. Preferably, the active agents are provided in separate containers.

In another embodiment, containers may hold a composition having a supportive agent, which is supportive of the active agent. Such supportive agents may be buffers. The supportive agent will depend upon the active agent. Exemplary supportive agents include, without limitation, exonuclease reaction buffer, debranching enzyme reaction buffer, decapping enzyme reaction buffer, siRNA reaction buffer, RT-PCR reaction buffer, or combinations thereof. Supportive agents may be combined into a single container or provided in separate containers. Preferably, the active agents are provided in separate containers.

In another embodiment, containers may contain siRNAs or sources for producing siRNA. The siRNA may be species specific. Any siRNA known in the art or yet to be discovered may be provided with the kit.

In another embodiment, containers may contain total RNA for control RT-PCRs to assess lariat purification. The total RNA may be from any species.

In another embodiment, containers may contain oligonucleotides, or primers, for control RT-PCRs. Such primers will amplify a well characterized linear RNA, lariat RNA, or combinations thereof, depending upon the control desired. One skilled in the art will recognize that the primers may be species specific and may depend upon the source species of the total RNA. For example, if the source of the total RNA is *Saccharomyces cervisiae*, then the control primers could be those that would amplify ACT1 mRNA and the ACT1 intron lariat RNA.

The article of manufacture may also contain instructs of use.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, the phrase "metallophosphatase domain" refers to the amino acids that are conserved among debranching enzymes isolated from various species.

As used herein, the term "enrich" or forms thereof refer to increasing the amount of a substance found in a heterogeneous population. For example, enriching for lariat RNA in an RNA population refers to increasing the proportion of lariat RNA in an RNA population to a proportion above the other types of RNA found in the RNA population. The enrichment includes purifying an RNA population to only include a specific type of RNA, such as lariat RNA.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. A, non-limiting example of stringent hybridization conditions are hybridization in 6× sodium chloride/sodium citrate (SSC) at about 45° C., followed by one or more washes in 0.2.×SSC, 0.1% SDS at 50-65° C. (e.g., 50° C. or 60° C. or 65° C.) Preferably, the isolated nucleic acid molecule of the invention that hybridizes under stringent conditions corresponds to a naturally-occurring nucleic acid molecule. As used herein, a "naturally-occurring" nucleic acid molecule refers to RNA or DNA molecules having a nucleotide sequence that occurs in a human cell in nature (e.g., encodes a natural protein).

As used herein, the phrase "lariat RNA" refers to the pre-mRNA that is excised during the formation of mRNA. This excised pre-mRNA forms a lariat structure.

As used herein, the phrase "linear RNA" refers to RNA that does not form a lariat structure and that can be degraded by exonucleases.

As used herein, the phrase "linear RNA degrading enzyme" refers to any enzyme capable of degrading linear RNA. Such enzymes include, without limitation, 3' exonucleases, 5' exonucleases, exonucleases with 3' and 5' activity, as well as others known in the art or yet to be discovered.

As used herein, the term "nucleic acid sequence" is intended to include DNA molecules (e.g., cDNA or genomic DNA) and RNA molecules (e.g., mRNA or lariat) and analogs of the DNA or RNA generated using nucleotide analogs. The nucleic acid molecule can be single-stranded or double-stranded.

As used herein, the phrase "RNA population" refers to a sample containing ribonucleic acid. The RNA population may or may not be purified RNA.

The following examples are simply intended to further illustrate and explain the present invention. The invention, therefore, should not be limited to any of the details in these examples.

EXAMPLES

Example 1: Materials and Methods

Yeast and Bacterial Strains, Plasmids, and General Procedures.

The following yeast strains were used: TMY30 (MATα ura3-52 lys2-801 ade2-101 trpI-Δ63 his3-Δ 200 leu2-Δ1), TMY60 (TMY30 dbr1::neo$^r$), TMY497 [=TMY30 mutated to dbr1 (D180Y allele)], TMY498 [TMY30 mutated to dbr1 (G84A allele)], TMY499 [=TMY30 mutated to dbr1 (Y68S allele)}. TMY453, a dbr1IΔ::hisG version of sigma strain 10560-23C, was used for FLO8 RT-PCR experiments (sigma strain 10560-23C=MATalpha ura3-52 his3::hisG leu2::hisG). The dbr1Δ::hisG allele was created using pTM513, a DBR1 gene blaster plasmid containing dbr1 Δ::hisG-URA3-hisG, and targeted to replace DBR1 chromosomal sequences by digestion with PvuII.

The following *E. coli* strains were used: Rosetta DE3 [F$^-$ ompT hsdS$_B$(r$_B^-$ m$_B^-$) gal dcm (DE3) pLysSRARE (Cam$^R$)]; XL1 Blue [F'::Tn10 proA$^+$B$^+$ lacI$^q$ Δ(lacZ)M15/recA1 endA1 gyrA96 (Nal$^r$) thi hsdR17 (r$_k^-$ m$_k^+$) supE44 relA1 lac]; JM109 [F' traD36 lacI$^{q-}$ Δ(lacZ)M15 proA$^+$ B$^+$/e14$^-$ (McrA$^-$) Δ(lac-proAB) thi gyrA96 (Nal$^r$) endA1 hsdR17 (r$_k^-$ m$_k^+$) relA1 supE44 recA1], ES1301 [lacZ53 thyA36 rha-5 metB1 deoC IN(rrnD-rrnE) mutS201::Tn5]; and TOP10 (F-mcrA Δ (mrr-hsdRMS-mcrBC) φ80lacZ Δ M15 ΔlacX74 recA1 deoR araD139 D(ara-leu)7697 galU galK rpsL (Str$^R$) endA1 nupG).

The following plasmids were used for this study: pET16b-DBR1 was used to express Dbr1p in *E. coli*. pRS306 was used as a URA3 template for making a PCR fragment to create a dbr1Δ::URA3 allele at the DBR1 locus. YEp351 (LEU2) was used in co-transformations with the PCR fragment that resulted in the creation of a dbr1Δ::URA3 strain. This strain was an intermediate in the creation of dbr1 point mutants. pTM431, pTM432, and pTM435 were all created by random mutagenesis of pYES2/GS-DBR1 and encode Dbr1p D180Y, Dbr1p G84A, and Dbr1p Y68S, respectively. The DBR1 gene blaster plasmid pTM513 was created in three steps. First, the 3.8 kbp BamHI-BglII fragment from pNKY51, containing hisG-URA3-hisG, was ligated into the BamHI site of pBluescript to create pTM509. Second, the 5' UTR of DBR1 was amplified from genomic DNA using oligonucleotide primers 331 and 332, then the PCR product was trimmed with EcoRI and BamHI and ligated into EcoRI and BamHI sites of pTM509 to create pTM511. Third, the 3' UTR of DBR1 was amplified from genomic DNA using oligonucleotide primers 333 and 336, then the PCR product was trimmed with XbaI and NotI and ligated into XbaI and NotI sites of pTM511 to create pTM513.

When not specifically described, general molecular techniques (Ausubel et al. 2003) as well as standard yeast media and general procedures (Kaiser et al. 1994) were used. Oligonucleotides are listed in Tables 1 and 2.

RNA Extraction.

Yeast strains were grown to mid-logarithmic phase prior to isolating total cellular RNA. In some cases yeast cells were used directly for RNA preparation after cell growth was complete. In other cases, yeast cells were pelleted and flash frozen in a dry ice ethanol bath and stored at −80° C. prior to RNA preparation. No difference was found in results for RNAs prepared from cells processed in these two ways. Total yeast RNA was prepared by the hot acid phenol method (Ausubel et al. 2003) or by a column purification method (RNeasy kit, Qiagen) from small cultures (10 ml) grown to mid-logarithmic phase ($OD_{600}=\sim 1$). RNA samples were treated with RNase free DNase I to remove DNA contamination. RNA concentration was measured spectrophotometrically by reading $OD_{260}$. The $OD_{260}/OD_{280}$ ratio was used as an RNA quality assessment.

Preparation of Dbr1p Enzyme from *E. coli*.

The pET16b-DBR1 expression plasmid encodes yeast Dbr1p as an N-terminal 10x-histidine-tagged protein. Expression and purification of the histidine-tagged Dbr1p were performed as described in Martin et al. 2002. Rosetta DE3 *E. coli* cells were used for expression of Dbr1p instead of *E. coli* strain BL21-Codon Plus(DE3)RIL. Sonication of cells was performed on ice for 60 sec., in 1 sec. pulses, with a large probe at 50% power. Triton X-100 was added after sonication to a final concentration of 0.1%. The tagged Dbr1p was purified from *E. coli* extracts by binding to and eluting from Nickel-nitrilotriacetic acid-agarose columns and fractions were assessed by sodium dodecyl sulfate-polyacrylamide gel electrophoresis (SDS-PAGE). Peak fractions from the elution were dialyzed against debranching buffer (20 mM HEPES KOH, pH 7.9; 125 mM KCl; 0.5 mM $MgCl_2$; 1 mM DTT; 10% glycerol). In some cases, Dbr1p was concentrated by spinning through a Microcon YM-30 spin concentrator at 14,000×g for 40 min. at 4° C. in a Beckman Allegra 25R centrifuge (TA-15-1.5 rotor). The concentrations of Dbr1p preparations were 50-100 ng/μl. Mass spectrometry of purified Dbr1p was performed.

Enzymatic Treatments of RNA.

*Bacillus stearothermophilus* PNPase was acquired (Sigma, St. Louis, Mo.) and a stock of 3.5 units/ml was prepared by dissolving the protein in water, then adding Tris HCl, pH 8.5, to a final concentration of 50 mM. PNPase reactions were performed in PNPase buffer (50 mM Tris HCl, pH 8.5; 1 mM 2-mercaptoethanol; 1 mM EDTA; 20 mM KCl; 15 mM $MgCl_2$; 10 mM $Na_2HPO_4$, pH 8.3) on 20-1000 ng of total yeast RNA in 20 μl reactions for 1 h at 60° C., using 1 μl of the PNPase stock. Upon completion of reactions, samples were heated to 85° C. for 10 min, then either used directly in RT-PCRs or ethanol precipitated. Mock treatments were performed in the same way, minus PNPase.

Approximately 50-100 ng of yeast Dbr1p prepared from *E. coli* was used for in vitro debranching reactions of 20-200 ng of RNA. Reactions were performed at 30° C. for 45 min. in a 20 μl volume containing 1× debranching buffer (20 mM HEPES-KOH pH 7.9, 125 mM KCl, 0.5 mM $MgCl_2$, 1 mM DTT and 10% glycerol). Reactions were stopped by heating at 65° C. for 10 minutes (min.). Mock treatments were performed in the same way, minus Dbr1p.

For sequential enzymatic treatments, RNA samples were phenol/chloroform extracted and ethanol precipitated after the first treatment (PNPase or Dbr1p) then resuspended and treated with the second enzyme.

RT-PCR Methods.

RT-PCRs of lariat and linear RNAs were performed with QIAGEN one-step RT-PCR kit (Valencia, Calif.) under the following general conditions: 50° C., 30 min; 95° C., 15 min; 9 cycles of 94° C. for 30 sec, 54° C. for 30-60 sec [touchdown to 46° C. (−1° C. per cycle)], 72° C. for 30 sec; X cycles (see below) of 94° C. for 30 sec, 46° C. for 30 sec, 72° C. for 30-45 sec; 72° C. for 5-10 min; 4° C. hold. The number of cycles in the post-touchdown phase of different RT-PCRs (X cycles above) varied with the experiment and are reflected in the following reaction profile names: ACT1-1, 29 cycles, post-touchdown; ACT1-2, 24 cycles, post-touchdown; ACT1-3, 19 cycles, post-touchdown; ACT1-4, 15 cycles, post-touchdown; and ACT1-5, 11 cycles, post-touchdown. RNA amounts between 2 ng and 50 ng were used in RT-PCRs. RT-PCRs were analyzed by either PAGE or agarose gel electrophoresis.

Real-Time RT-PCR (qRT-PCR) of Lariat and Linear RNAs.

Primers and probes for qPCR were designed using Sequence Detection Systems software from Applied Biosystems (Carlsbad, Calif.) and are listed in Table 1. All probes and primers for qRT-PCR were purchased from Applied Biosystems. Validation experiments were performed that demonstrated that the efficiencies of target and reference PCRs are approximately equal.

TABLE 1

Primers and probes for qRT-PCR.

| SEQ ID NO: | Target and Primers Probe | Sequence | Position[a] |
|---|---|---|---|
| 28 | FWD primer | TCCCAAGATCGAAAATTTACTGAAT | −30 to 6 |
| 29 | REV primer | TTTACACATACCAGAACCGTTATCAT | 54 to 28 |

TABLE 1-continued

Primers and probes for qRT-PCR.

| SEQ ID NO: | Target and Primers Probe | Sequence | Position[a] |
|---|---|---|---|
| 30 | TaqMan probe ACT1 intron: | VIC - TGAATTAACAAGGTTGCTG CT - MGBNFQ | -4 to 26 |
| 31 | FWD primer | ATTTTTCACTCTCCCATAACCTCCT ATA | 94 to 121 |
| 32 | REV primer | TTTCAAGCCCCTATTTATTCCAAT | 173 to 150 |
| 33 | TaqMan probe RPP1B mRNA: | 6FAM - TGACTGATCTGTAATAAC CA - MGBNFQ | 123 to 142 |
| 34 | FWD primer | AGGCCGCTGGTGCTAATG | 89 to 106 |
| 35 | REV primer | TCCAAAGCCTTAGCGTAAACATC | 146 to 124 |
| 36 | TaqMan probe RPP1B intron: | VIC - CGACAACGTCTGGGC - MGBNFQ | 108 to 122 |
| 37 | FWD primer | AATGCAACCTAAAACGACTTTGTG | 12 to 35 |
| 38 | REV primer | TTTCTCGGGACGATTGTTGTC | 77 to 57 |
| 39 | TaqMan probe YRA1 mRNA: | 6FAM - ACTACGAAGAGAAAGAT T - MGBNFQ | 38 to 55 |
| 40 | FWD primer | AGGTTTGCCAAGGGACATTAAG | 249 to 270 |
| 41 | REV primer | ACACCACCTACTTGAGATGCAAAA | 314 to 291 |
| 42 | TaqMan probe YRA1 intron: | VIC - AGGATGCTGTAAGAGAA T - MGBNFQ | 272 to 289 |
| 43 | FWD primer | CGCATCGTCTCGTGTGGAT | 42 to 60 |
| 44 | REV primer | GATCAAAAGCGTGTGCCATATC | 107 to 86 |
| 45 | TaqMan probe | 6FAM - CGAGAAATATTCTTTGTA AGGAA - MGBNFQ | 62 to 84 |

[a]Relative to start of coding sequence for mRNA primers and probes. Relative to start of intron sequence for intron primers and probes.

For total RNA samples (untreated or treated with Dbr1p/PNPase, as described above), 20-1000 ng of RNA was reverse transcribed into cDNA using random hexamers in a 100 µl reaction at 45° C. for 60 min.

PCR MasterMix reagents from Applied Biosystems were used for qPCR reactions, which were performed in triplicate for each sample. Reactions were prepared and run according to a standard protocol established by Applied Biosystems on an ABI 7500 real-time PCR machine. Briefly, reactions contained 2×PCR MasterMix, 900 nM forward primer, 900 nM reverse primer, 250 nM TaqMan probe, and cDNA (~20 ng). Reactions were incubated for 2 minutes at 50° C. and then 10 minutes at 95° C. and before proceeding through 40 cycles of a 30 second (sec) incubation at 95° C. and a 60 second incubation at 60° C. Completed reactions were held at 4° C.

Relative quantification (RQ) of results was performed using the comparative CT method ($\Delta\Delta C_T$) (Schmittgen and Livak 2008). The amplification of each target intron sequence was compared to amplification of the corresponding mRNA sequence and a $\Delta C_T$ was determined. To compare the different samples to each other, the wild-type sample was used as the calibrator sample. Therefore, the $\Delta C_T$ of the wild-type sample was subtracted from the $\Delta C_T$ for each sample to determine $-\Delta\Delta C_T$ values. In FIG. 7, RQ $2^{-\Delta\Delta C_T}$ for each $-\Delta\Delta C_T$ and represents the fold-difference in intron levels between a given sample and the wild-type sample (DBR1).

In Vitro Debranching Time Course.

Glyceraldehyde-3-phosphate dehydrogenase (GAPDH) cDNA, the exogenous control for qPCR in these experiments, was generated by reverse transcribing 600 ng of human RNA at 45° C. for 1 hour (hr) using the reverse transcriptase (RT) kit from Applied Biosystems. A debranching reaction mix was set up on ice and contained 5600 ng of total RNA from TMY60 (dbr1) cells, about 6 ng GAPDH cDNA, 140 µl of purified Dbr1p, and 350 µl 2× debranching buffer in a final volume of 700 µl. Seven 100 µl aliquots of this mix were distributed to 0.2 mL PCR tubes. The debranching reaction was directly inactivated in one tube (0 min reaction time) by raising the temperature to 95° C., followed by phenol/chloroform extraction and ethanol precipitation. The remaining six tubes were incubated at 30° C. and individual reactions were stopped after 2.5 min, 5 min, 10 min, 15 min, 30 min, and 60 min. Reactions were stopped by raising the temperature to 95° C., followed by phenol/chloroform extraction and ethanol precipitation. RNAs were then treated with PNPase, as described above, to degrade intron lariats linearized by Dbr1p. Reverse transcription of the RNAs remaining from the different debranching reactions was performed using the RT kit from Applied Biosystems and random hexamer primers. qPCRs using these cDNAs were performed as described above, amplifying a volume of cDNA roughly corresponding to about 20 ng of starting total RNA, using primers and probes for yeast ACT1, YRA1, and RPP1B introns as well as human GAPDH. GAPDH cDNA was the exogenous control because it is insensitive to PNPase and remained at a constant level in each reaction.

Creation of Dbr1 Point Mutant Strains.

Mutants were created using modifications of the delitto perfetto method (Storici et al. 2001) and the site specific genomic (SSG) method (Gray et al. 2004). Initially, a dbr1Δ::URA3 strain was created to facilitate the introduction of point mutant alleles of dbr1 into the DBR1 locus. Yeast strain TMY490, containing a URA3-marked deletion of 1090 bp of the 1215 bp DBR1 coding sequence (nts 71-1160 deleted), was constructed by transformation of TMY30 with a PCR fragment containing the URA3 gene from pRS306 flanked by ends corresponding to 5' and 3' segments of the DBR1 coding region.

The fragment used for making the dbr1Δ::URA3 allele was created by PCR of pRS306 with oligonucleotides 443 and 444, the 3' 20 nucleotide (nt) of which anneal to the ends of the URA3 gene on pRS306 and the 5' 40 nt of which correspond to DBR1 sequences (see Table 2).

TABLE 2

Oligonucleotides.

| SEQ ID NO: | Primer | Sequence | Position[a] |
|---|---|---|---|
| 1 | 146 | cactctcccataacctccta | ACT1 intron nt 100-119 |
| 2 | 215 | ctcaaaccaagaagaaaaagaa | ACT1 nt -128 to -107 |
| 3 | 216 | tgataccttggtgtcttggtct | ACT1 nt 130 to 109 |
| 4 | 331 | aggatgtttccgtctttagaa | -761 to -741 upstream of DBR1 ORF |
| 5 | 332 | gaggatcctgataaatgtctgcccatctt | -10 to -30 upstream of DBR1 ORF; EcoRI site added at 5' end |
| 6 | 333 | gctctagaacgaatgcagacggaattaga | 16 to 30 after of DBR1 stop codon; XbaI site added at 5' end |
| 7 | 336 | ataagaatgcggccgcaaagggatccaatgtggtga | 779 to 760 after of DBR1 stop codon; NotI site added at 5' end |
| 8 | 363 | gcaagcgctagaacatacttag | ACT1 intron nt 18-1, 265-262 |
| 9 | 372 | agtgaatagttcgtatccagattc | FLO8 nt 12-35 |
| 10 | 373 | catacaaaaagccttgaggtg | FLO8 nt 418-398 |
| 11 | 374 | ggtagcaaatattctgggacatct | FLO8 nt 422-445 |
| 12 | 375 | attctgggttggccctacattt | FLO8 nt 837-816 |
| 13 | 376 | agtcaaaacgttactggctgg | FLO8 nt 841-861 |
| 14 | 377 | tgcttgattgcggaagttag | FLO8 nt 1260-1241 |
| 15 | 378 | ttggcgaggaagatatttattc | FLO8 nt 1268-1289 |
| 16 | 379 | aagataatggactggatacagccg | FLO8 nt 1675-1652 |
| 17 | 380 | ttcgatccagaaagtggcaa | FLO8 nt 1693-1712 |
| 18 | 381 | ttttcctctggagtagataatgtg | FLO8 nt 2036-2013 |
| 19 | 382 | atcaaggatatgattttgacgc | FLO8 nt 2054-2075 |
| 20 | 383 | cagccttcccaattaataaaattg | FLO8 nt 2399-2376 |
| 21 | 408 | taaatagcttggcagcaacagg | URA3 nt 67-46 |
| 22 | 417 | ttgcgaattgctgtacaagg | DBR1 nt 10-29 |
| 23 | 418 | caagtcatgaatttagagataaatgc | DBR1 nt 1217-1192 |
| 24 | 443 | gctgtcatggtcagctaaaccaaatttataaagaagtgt . . . | 5' 40 nt = DBR1 nt 31-70 |
| 25 | 443cont | . . . taactatgcggcatcagagc | 3' 20 nt = URA3 flank in pRS306 |
| 26 | 444 | gataaatgctttagtttgtcgtacttcatctttctgaata . . . | 5' 40 nt = DBR1 nt 1200-1161 |
| 27 | 444cont | . . . cctgatgcggtattttctcc | 3' 20 nt = URA3 flank in pRS306 |

[a]For the ACT1, FLO8, URA3 and DBR1 genes, the nucleotide positions are relative to the first nucleotide of the coding sequence, except for the ACT1 intron, where positions are relative to the first nucleotide of the intron.

The dbr1Δ::URA3 disruption on yeast chromosome XI was created by homologous recombination between the DBR1 locus and the dbr1Δ::URA3 PCR fragment. Briefly, TMY30 was transformed with the dbr1Δ::URA3 PCR fragment and transformants were selected on SD-Uracil plates. Transformants were screened by PCR with primer pairs 401/402, which anneal within the DBR1 sequences that are deleted in the dbr1Δ::URA3 allele, and 417/418, which anneal outside the DBR1 sequences that are deleted in the dbr1Δ:: URA3 allele. Transformants containing the dbr1Δ:: URA3 allele template a 417/418 PCR product but not a 401/402 PCR product. DNA sequencing of PCR products was performed to verify the presence of the dbr1Δ:: URA3 allele.

Replacement of the chromosomal dbr1Δ:: URA3 allele with dbr1 point mutations was accomplished by transformation. TMY490 (dbr1Δ:: URA3 strain) was co-transformed with YEp351(LEU2) and PCR fragments of dbr1 point mutants. The PCR fragments were generated from plasmids pTM431, pTM432, and pTM435 with PCR primer pairs 417/418. Transformants (with YEp351) were selected in SD-leucine liquid media during a 48 hr incubation period at 30° C. (with shaking). After this selection period, cells were spread onto 5-fluoroorotic acid plates to select for cells that lost function of the URA3 gene within the DBR1 locus. Recombinants within the FOA$^r$ population that have replaced the dbr1Δ:: URA3 allele with a dbr1 point mutant allele were identified by PCR screening. Positive clones were identified as those that template a 417/418 PCR product but not a 417/408 PCR product (specific for the dbr1Δ:: URA3 allele). DNA sequencing of PCR products was performed to verify the presence of a dbr1 point mutant allele.

Example 2: RT-PCR Detection of Lariat RNAs

Figure 1B:
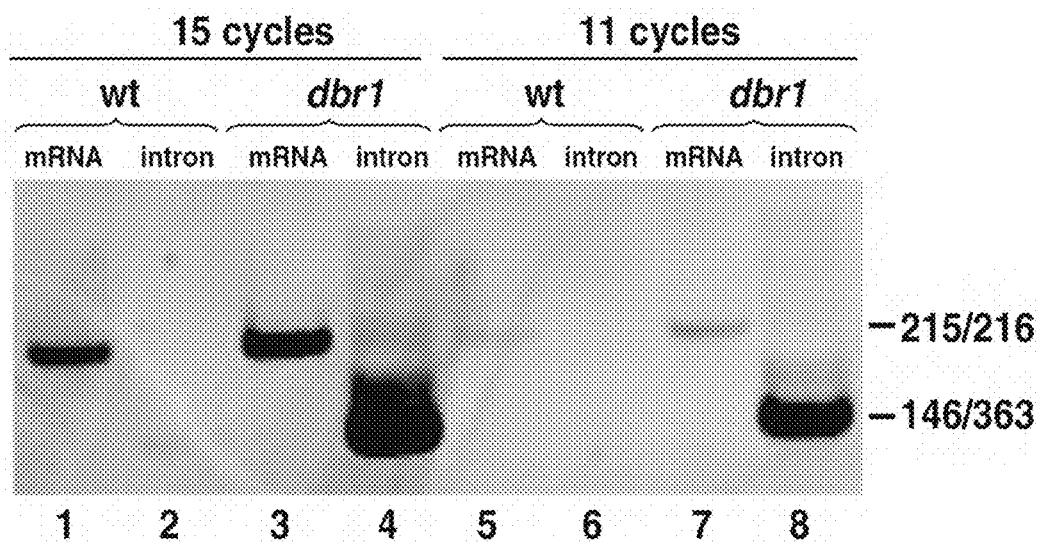
FIG. 1B shows an agarose gel analysis of RT-PCRs for ACT1 RNA detected using the primers illustrated in FIG. 1A (mRNA=oligos 215/216; intron=oligos 146/363). Lanes 1-4 contain reactions run 15 cycles after the touchdown phase of polymerase chain reaction (PCR); lanes 5-8 contain reactions run 11 cycles after the touchdown phase of PCR; Lanes 1, 2, 5, and 6 contain reactions using wild type (DBR1) RNA samples; and, lanes 3, 4, 7, and 8 contain reactions using dbr1 mutant RNA samples. The different numbers of cycles were run to show the linearity of the PCRs.

S. cerevisiae ACT1, which encodes actin, is a robustly expressed gene that contains an intron of 308 nt. The first example of a spliceosomal intron discovered in yeast, the ACT1 intron contains all the canonical features of yeast introns and is efficiently spliced from pre-mRNA, producing an excised lariat with a 265 nt circle. This well-characterized gene was chosen to assess intron levels as tools were developed and tested for detecting and enriching excised intron lariats. Primers were designed for use in RT-PCR to detect the lariat form of the ACT1 intron RNA and, as a control, ACT1 mRNA (FIG. 1A). RT-PCR of total yeast RNA using primers that flank the ACT1 exon-exon junction (primers 215 and 216) amplifies a 285 bp product from ACT1 mRNA. Primer 363 spans the ACT1 intron lariat branch point and is used in combination with primer 146, which anneals to sequences complementary to the ACT1 intron upstream of the lariat branch point, in an RT-PCR that amplifies a 184 bp product from the lariat form of the ACT1 intron RNA. As expected, when RT-PCRs are performed using total RNA samples from wild-type (TMY30) and dbr1 mutant yeast cells (TMY60), the amounts of ACT1 mRNA products are similar when using equivalent amounts of RNA from the two cell types (FIG. 1B, lanes 1 and 3 as well as lanes 5 and 7). However, the ACT1 intron RNA lariat product is much more readily produced from dbr1 cells (FIG. 1B, lane 4 vs. 2 and lane 8 vs. 6). These data clearly show that a dbr1 mutant strain or, where appropriate, a Dbr1p knock-down strain contains a rich source of expressed intron sequences. It is also evident that the use of intron-specific RT-PCR could be used to detect excised introns from genes expressed at very low levels. For studies on alternative splicing, the use of RT-PCR on RNA from Dbr1p-deficient cells can allow detection of rare splice variants.

A previous report described the use of radiolabeled primers spanning intron RNA branch points for analyzing intron populations by primer extension (Spingola et al. 1999). The RT-PCR method we describe could be modified to survey intron lariats containing specific sequences at intron 5' ends and branch points. RT-PCR has added utility because the products can be cloned and sequenced to identify the individual introns represented in a lariat population.

Example 3: Insensitivity of Lariat RNAs to the 3' Exonuclease PNPase

Figure 2A:
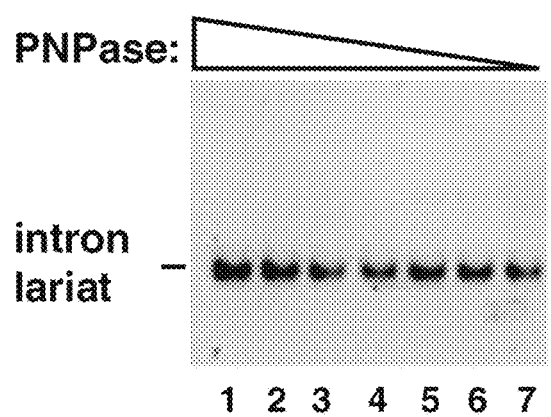
FIG. 2A,B illustrates selective degradation of linear RNAs and not lariat RNAs.
Figure 2B:
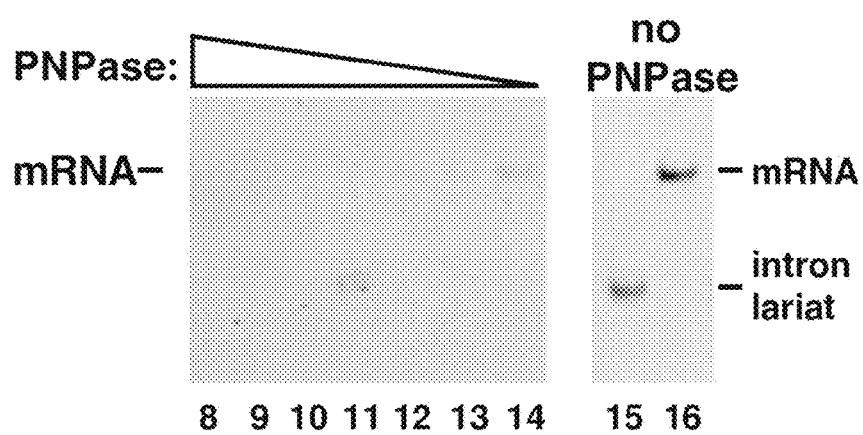
FIG. 2B shows an agarose gel analysis of RT-PCRs for ACT1 linear mRNA from the same series of enzyme treatments of FIG. 2A. Lanes 15 and 16 contain ACT1 intron lariat and ACT1 linear mRNA RT-PCRs, respectively, of RNA samples that did not undergo PNPase treatment. The products in these lanes serve as size markers for the intron lariat and mRNA products in lanes 1-14. RT-PCRs for ACT1 mRNA were performed with primers 215 and 216 (see FIG. 1A) and run for 24 cycles after the touchdown phase of the reaction.

Linear and lariat RNAs have different sensitivities to 3' exonucleases, including PNPase, a component of bacterial RNA degradation systems. PNPase degrades linear RNAs but does not proceed past the 2' branch present in intron RNA lariats. Therefore, treatment of RNA samples with an enzyme like PNPase should result in a vast enrichment of excised intron lariats in the RNA that remains intact after treatment. This difference should be evident in the results of the RT-PCR assay described above when amplifying PNPase-treated RNA samples. Since RNA secondary structures reduce the efficiency of PNPases, reactions were performed at elevated temperature (60° C.) using PNPase from Bacillus strearothermophilus to circumvent this problem. Total RNA samples from a dbr1 mutant strain (TMY60) were treated with a range of PNPase concentrations and then subjected to RT-PCR to detect ACT1 intron RNA lariats as well as the linear mRNA (FIG. 2). Results are consistent with expectations that the use of PNPase selectively preserves RNA lariats.

Figure 3A:
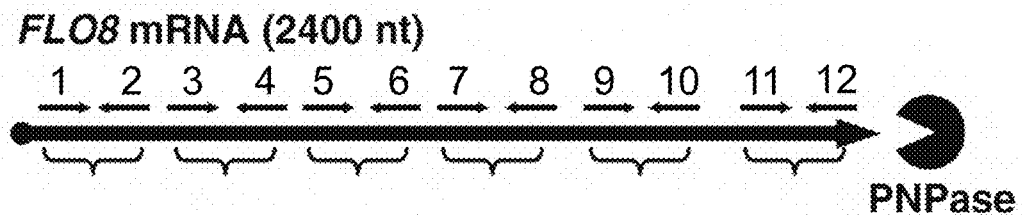
FIG. 3A-C illustrates processivity of PNPase on FLO8 mRNA.
Figure 3B:
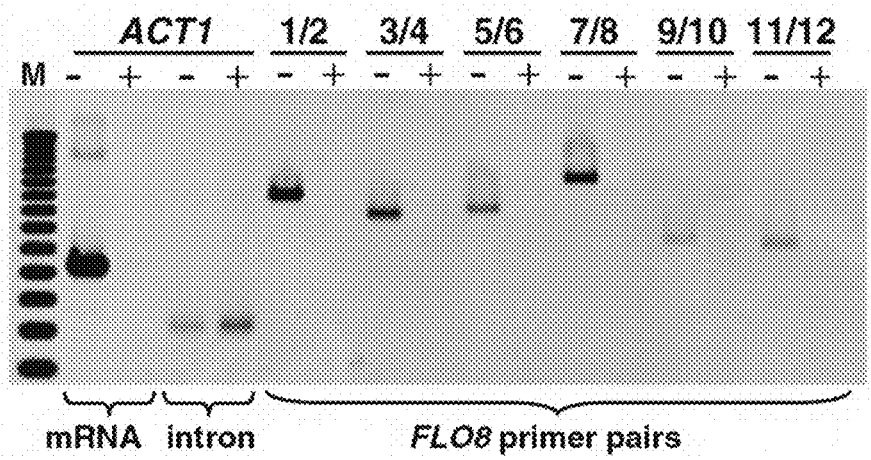
Figure 3C:
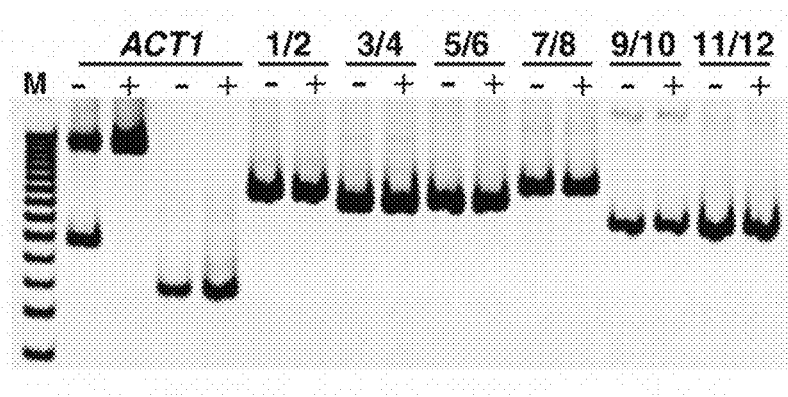

The high temperature reaction using PNPase from a thermophile appears to be much more efficient than the reported reaction with the E. coli PNPase at 37° C. In order to eliminate the RT-PCR product from the ACT1 mRNA, PNPase must degrade, at the very least, the RNA corresponding to the binding site for the downstream primer (oligonucleotide 216). To accomplish this, PNPase must degrade all the RNA that lies to the 3' side of the oligonucleotide 216 binding site, which includes 998 nt of the ACT1 coding sequence plus the 3' UTR and the polyA tail. To further examine the processivity of Bacillus strearothermophilus PNPase, the degradation of FLO8 mRNA was assessed. FLO8 mRNA is >2.4 kb in length. Primer pairs were designed to amplify different portions of this mRNA along its length (FIG. 3A). Total nucleic acid samples and RNA samples (DNased total nucleic acid samples) were treated with PNPase and subjected to RT-PCR to detect the various segments of FLO8. As shown in FIG. 3B, PNPase readily degrades every segment of FLO8 mRNA assayed. As expected, PNPase has no effect on FLO8 DNA present in the total nucleic acid samples (FIG. 3C). Other enzymes that worked as well as Bacillus strearothermophilus PNPase in our studies are Thermus thermophilus PNPase at 65° C. and Escherichia coli RNase Rat 37° C.

Example 4: Sensitivity of Lariat RNAs to Dbr1p

Linear and lariat RNAs also have different sensitivities to RNA debranching enzyme, which can be exploited to confirm that an RNA species have a lariat conformation. The RT-PCR strategy employing a primer that spans a lariat branch point, as described above for the ACT1 intron, can be used to demonstrate the cleavage of the 2'-5' bond. This is due to the fact that after Dbr1p treatment the binding site for the primer that spans the ACT1 intron branch point (oligonucleotide 363) is split into two non-contiguous sections, with the section that anneals to the 3' end of the primer being only 3 base pairs (bp) in length. After debranching of the lariat, the critical 3' end of the primer will not effectively anneal to the intron RNA to prime RT-PCR. Dbr1p treatment has no effect on ACT1 mRNA, which should still be readily detected by RT-PCR.

Figure 4A:
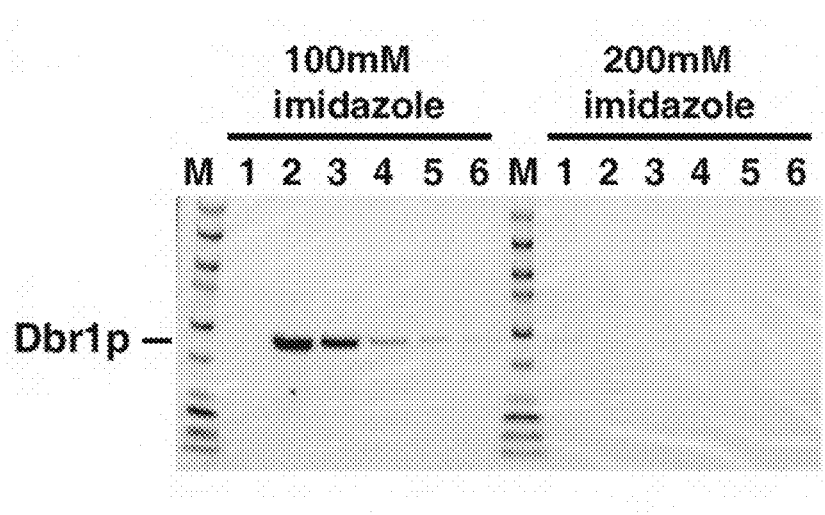
FIG. 4A-C illustrates the purification of Dbr1p.
Figure 4B:
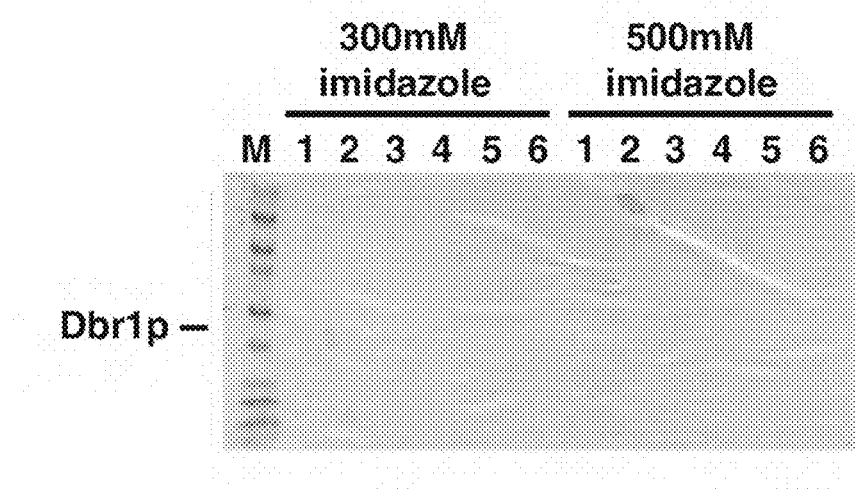
Figure 4C:
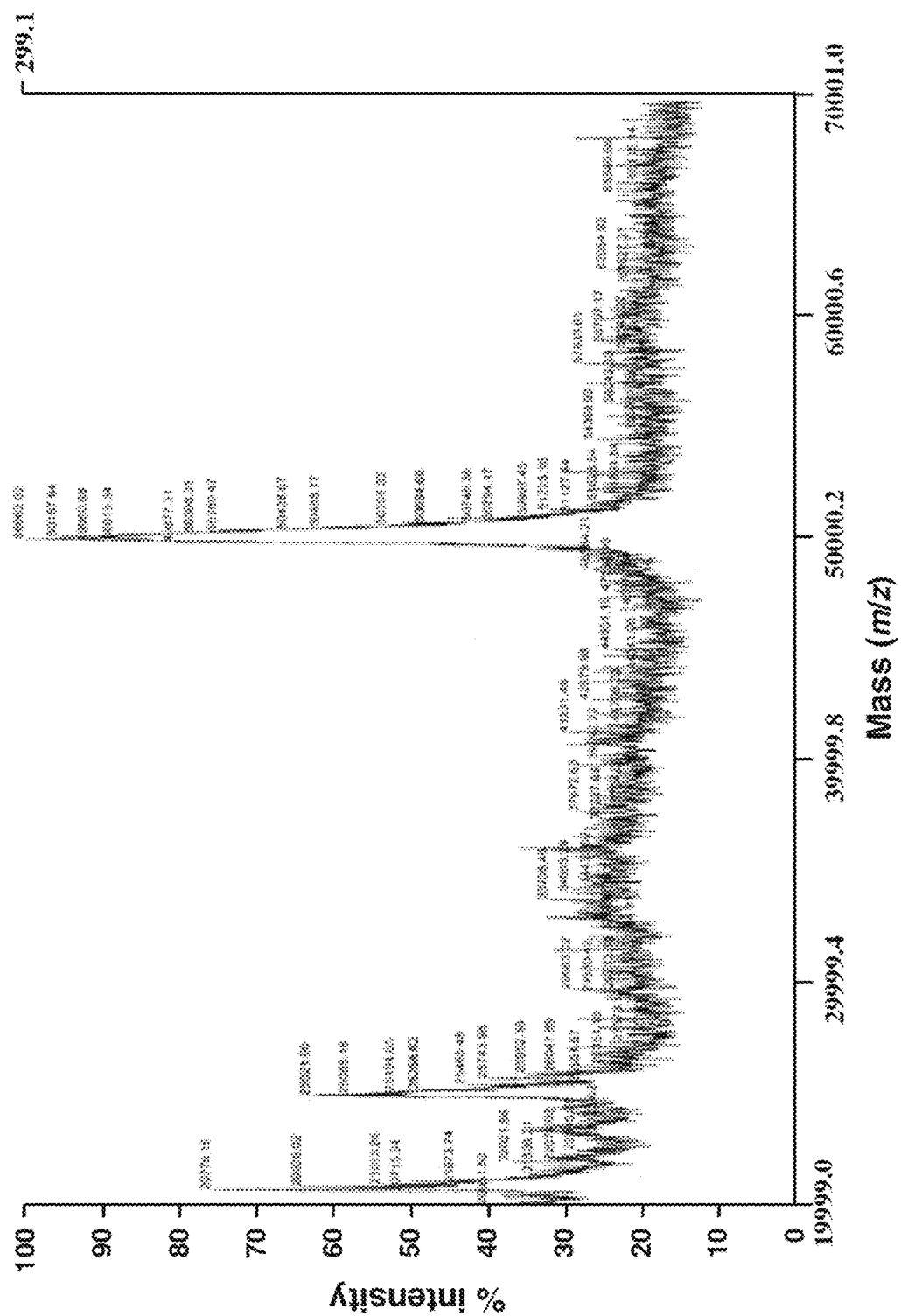

In order to perform Dbr1p treatments, S. cerevisiae Dbr1p was expressed in E. coli and purified by metal affinity chromatography (FIGS. 4A and 4B). Although histidine-tagged Dbr1p is expected to have a mass of about 50 kilo-dalton (kDa), the mobility of the main product in SDS-PAGE is about 45 kDa. Others have observed this anomalous mobility for histidine-tagged Dbr1p and have speculated that the protein may undergo limited proteolysis in E. coli. However, mass spectrometric analysis of the main band in the stained gel shows it to be the expected molecular mass of the histidine-tagged Dbr1p (50062 Dalton (Da)) (FIG. 4C), indicating that the protein is intact and must run anomalously in SDS-PAGE because of its physical properties.

Figure 5:
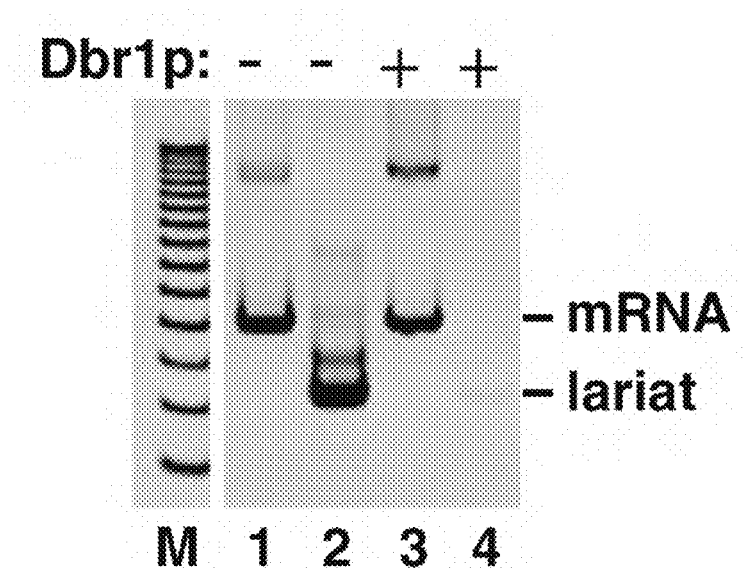
FIG. 5 illustrates an in vitro debranching reaction. Specifically.

Using the Dbr1p enzyme preparation, debranching reactions were carried out on total RNA samples from a dbr1 mutant strain. RT-PCR analysis reflects the differential sensitivity of linear and lariat RNAs to Dbr1p. After Dbr1p treatment, RT-PCR detection of ACT1 RNA lariat is greatly decreased (FIG. 5, lane 4 vs. 2). On the other hand, the product indicative of ACT1 linear mRNA is still readily detectable after Dbr1p treatment (FIG. 5, lane 3 vs. 1).

Example 5: Combinations of PNPase and Dbr1p Treatments

Figure 6A:
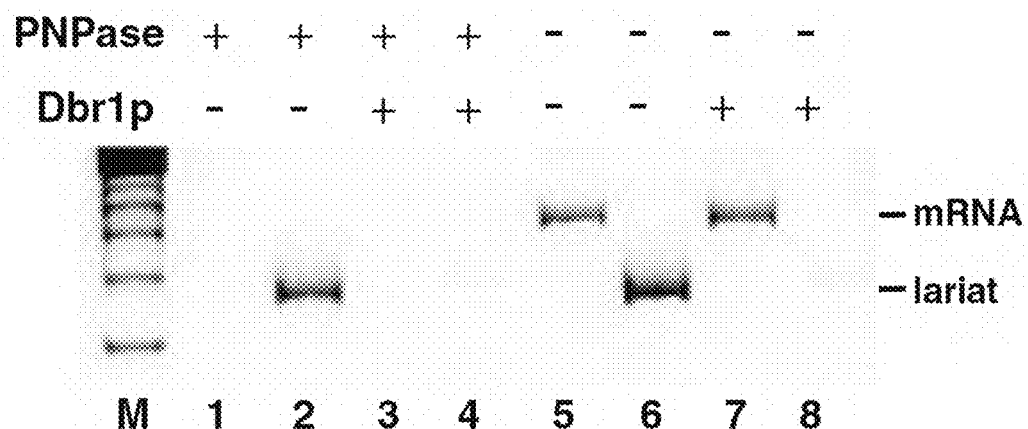
FIG. 6A,B shows combinations of PNPase and Dbr1p enzyme treatments.
Figure 6B:
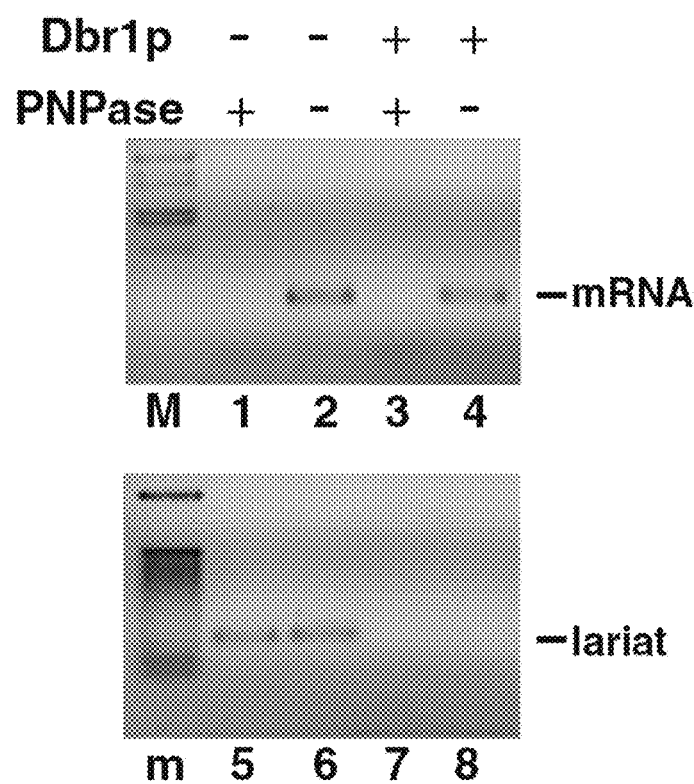
FIG. 6B shows an agarose gel analysis of RT-PCRs for ACT1 RNAs following treatment of a total cellular RNA sample from a dbr1 strain with Dbr1p and PNPase as well as mock treatment. In this experiment, Dbr1p treatment preceded PNPase treatment for samples that were treated with both enzymes. Lanes 1-4 contain RT-PCRs for ACT1 mRNA of a total cellular RNA sample. Lanes 5-8 contain parallel RT-PCRs for ACT1 intron lariat RNA. For both FIGS. 6A and 6B, RT-PCRs for ACT1 intron lariat RNA were run for 19 cycles after the touchdown phase of the reaction and RT-PCRs for ACT1 mRNA were run for 24 cycles after the touchdown phase of the reaction. The lanes marked "M" and "m" contain DNA molecular weight standards ("M"=λ phage DNA cut with HinDIII+EcoRI; "m"=50 bp ladder).

PNPase and Dbr1p treatments can be used in combination when exploring the properties of a particular RNA species. Sequential enzymatic treatments can also be used to enrich for RNA lariats and then linearize them for further manipulations. To demonstrate this, ACT1 RNA species present within a total RNA sample from a dbr1 mutant strain were analyzed by RT-PCR following sequential PNPase and Dbr1p treatments. As shown in FIG. 6A (lanes 1-4), initial treatment of the RNA sample with PNPase degrades the linear mRNA (lanes I and 3), but leaves lariat RNA intact (lane 2). Subsequent treatment with Dbr1p shows that the resistant RNA is a lariat (lane 4). As shown in FIG. 6A (lanes 5-8), skipping the initial PNPase treatment leaves the linear mRNA intact (lanes 5 and 7) as well as the lariat RNA (lane 6). The lariat RNA is then distinguished by its sensitivity to cutting with Dbr1p (lane 8). The order of the PNPase and Dbr1p reactions can be switched to generate a complementary set of predictable results (FIG. 6B).

Example 6: Real-Time RT-PCR Measurement of Lariat RNA Levels

A real-time RT-PCR method (qRT-PCR), using the TaqMan detection system (Applied Biosystems), was developed to quantitatively compare the intron RNA lariat levels of different samples. The study included not only the ACT1 intron but also the YRA1 and RPP1B introns to investigate the generality of the methods. YRA1 encodes an RNA binding protein involved in mRNA export from the nucleus and is moderately expressed, although less than ACT1. The YRA1 intron is 765 nt in length, which is larger than the 300 nt average for yeast introns, and contains a non-canonical branch point sequence. Furthermore, the intron is inefficiently spliced from pre-mRNA, which is important for the auto-regulation of Yra1p protein levels. RPP1B encodes a ribosomal protein and is even more highly expressed than ACT1. The RPP1B intron is typical for yeast, 301 nt in length, with canonical sequences.

Figure 7A:
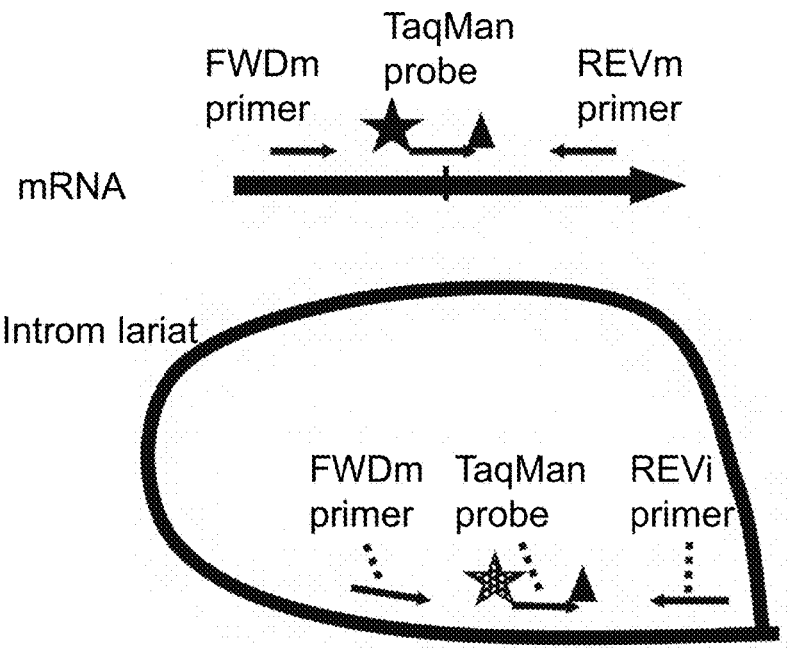
FIG. 7A-D shows real-time quantitative RT-PCR (qRT-PCR) measurement of lariat RNA levels.
Figure 7B:
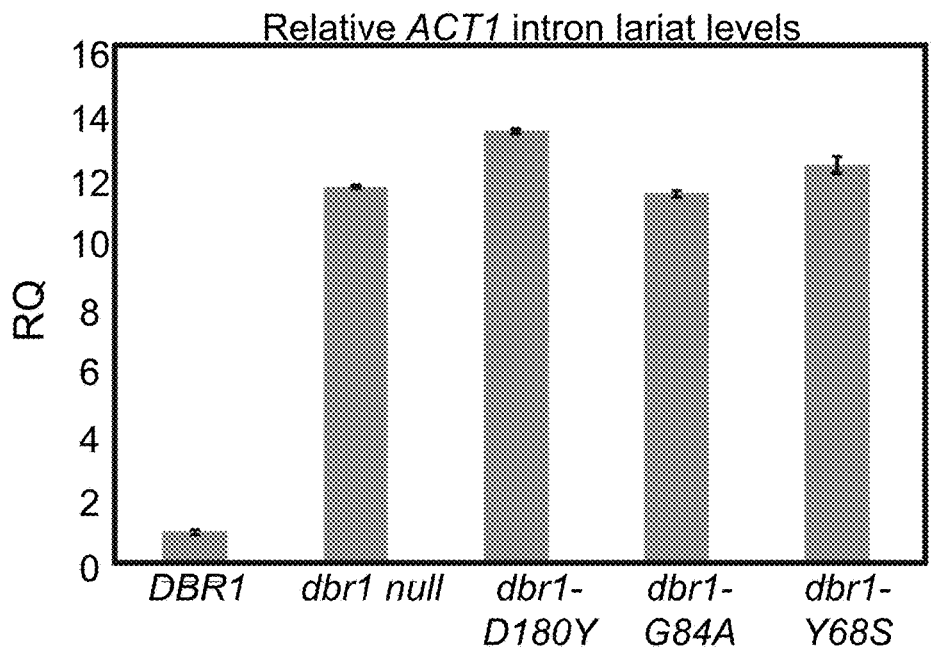
Figure 7C:
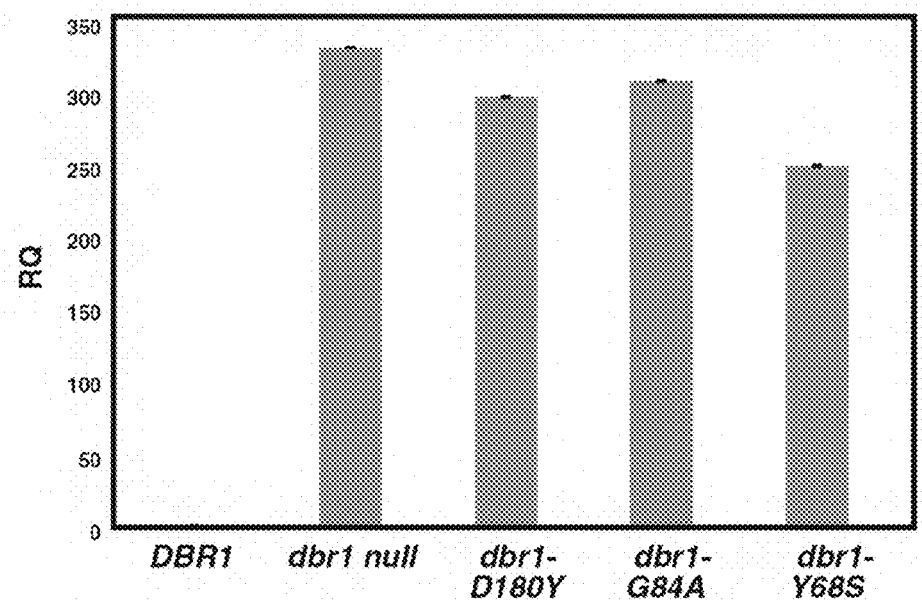
Figure 7D:
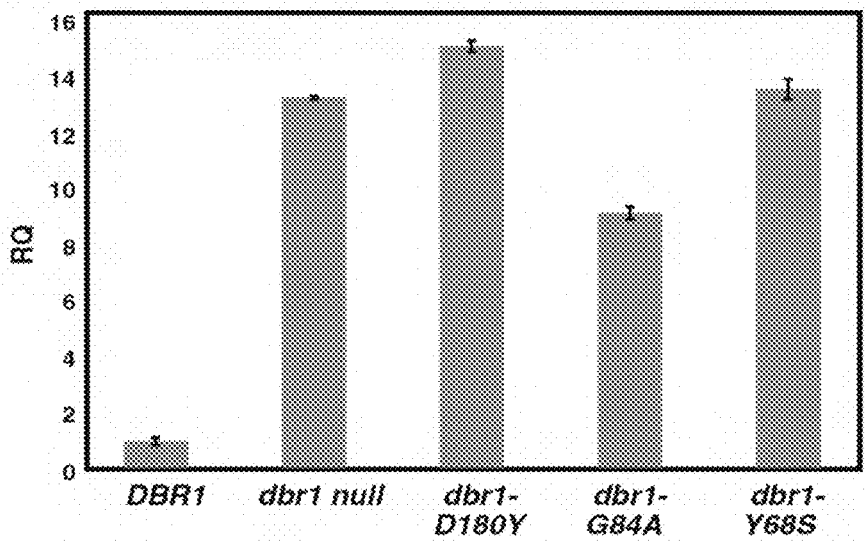

Initially, a strategy similar to the one used for RT-PCR of ACT1 intron lariats described above, with one primer spanning the lariat branch point and serving as both the RT primer and the reverse primer for PCR was used. However, a different strategy using random primers for the RT step was also used to allow amplification of the different target sequences from a common pool of cDNA. Consequently, both PCR primers anneal upstream of the branch point for each target gene, with a TaqMan probe annealing between them (FIG. 7A). Since these types of primers will also prime amplification of genomic DNA we ran control PCRs for each sample without a prior RT step to ensure that DNA contamination was not contributing to the PCR product. The mRNA for each target gene served as the endogenous control for qRT-PCR (FIG. 7A, top). Using this strategy, intron sequences for ACT1, RPP1B, and YRA1 were amplified from dbr1 and wild-type yeast strains (TMY60 and TMY30). As shown in FIGS. 7B, 7C and 7D [DBR1 (wild type) vs. dbr1 null mutant), the real-time method generated the expected results: the different intron RNAs accumulate at higher levels in the dbr1 null mutant strain than in wild type.

qRT-PCR was also us subject. ed to analyze mutant variants of Dbr1p. Previously, a set of point mutants had been created by random PCR mutagenesis and analyzed for intron RNA levels by an RNase protection assay. In these experiments, the dbr1 mutant alleles were under the control of a strong, inducible promoter (pGAL1) and carried on a high copy plasmid. The yeast strain carried a dbr1Δ mutation [open reading frame (ORF) deletion] at the DBR1 locus so the plasmid-borne dbr1 mutant alleles were the only sources of Dbr1p. For the current study, three dbr1 point mutants (D180Y, G84A, and Y68S) were analyzed by qRT-PCR to determine their levels of intron lariat RNA relative to wild-type (DBR1) and dbr1Δ. To make the analysis more biologically relevant, each of the dbr1 mutant alleles was placed at the DBR1 locus, replacing the wild-type allele, and was under the control of the native DBR1 promoter. After log-phase growth of cells, RNA samples from wild-type and mutant strains were harvested and subjected to qRT-PCR to amplify intron and messenger RNA sequences from ACT1, RPP1B, and YRA1. The three dbr1 alleles tested show strong intron RNA accumulation phenotypes, comparable to the dbr1Δ knockout allele (FIGS. 7B, 7C, and 7D).

Example 7: qRT-PCR Analysis of a Debranching Time Course

Figure 8:
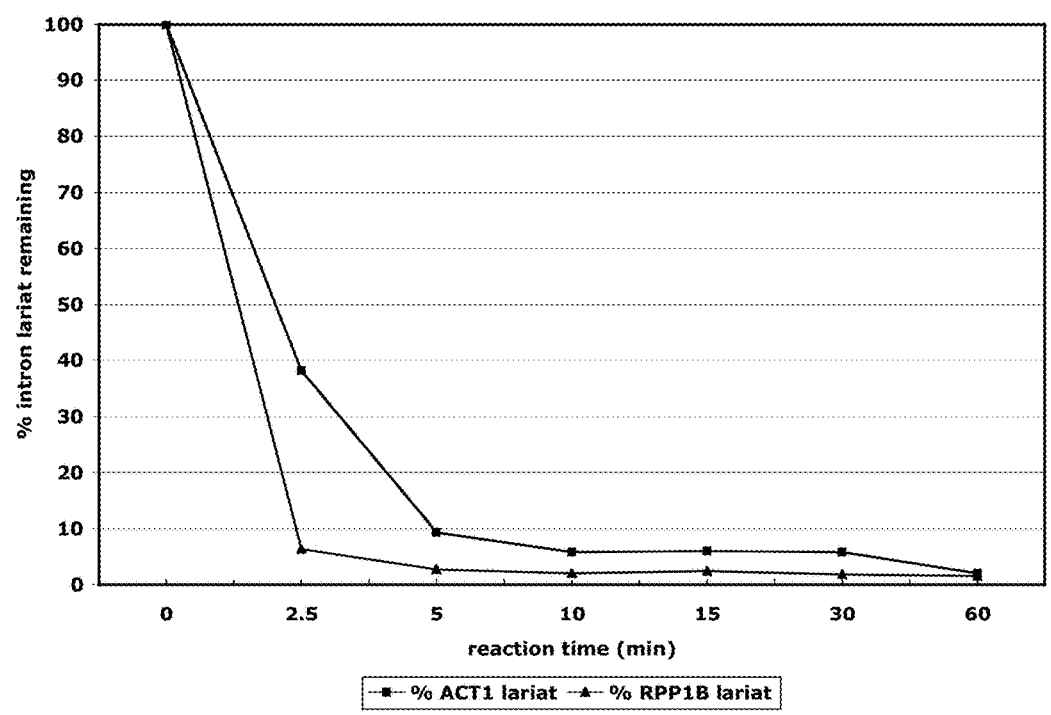
FIG. 8 graphically illustrates a time course of in vitro debranching reaction.

Using a combination of Dbr1p and PNPase treatments, in vitro debranching reactions of total cellular RNA from a dbr1 strain were followed over time courses of thirty minutes. Debranching reactions were stopped at different times and the reaction products were treated with PNPase to degrade linearized intron RNAs. The remaining intron lariats were detected by qRT-PCR as described herein. Because the PNPase treatment step degrades all linear RNAs, human GAPDH cDNA was added to the yeast RNA samples as an exogenous control. The GAPDH cDNA is insensitive to both Dbr1p and PNPase, remaining at the same level in the various samples. Debranching of the ACT1 and RPP1B intron lariats was almost complete within the first 5 minutes of the reactions (FIG. 8). However, the debranching rate of the ACT1 intron lariat appeared to be only two-thirds the initial rate of the RPP1B intron lariat.

The results observed from using qRT-PCR to follow in vitro debranching, show that the debranching rates can vary from one intron lariat to another. The ACT1 intron is debranched at only two-thirds the initial rate at which the RPP1B intron lariat is debranched. These data suggest that different intron lariats are debranched at different rates in vivo, which may be of functional significance. Slower rates of debranching may occur for introns that contain snoRNAs or mirtrons, reflecting the binding of additional factors to intron sequences or specific folding properties of the RNA. Thus, the rate of the debranching of introns can be used to predict which introns may contain additional information. Relative debranching rates can be inferred from quantitative analysis of intron RNA levels relative to mature mRNA levels for a given gene compared to a standard, rapidly debranching intron RNA. For these types of experiments, RNA samples could be taken from a wild-type strain (DBR1), where lariat RNAs are not stabilized. Inefficient splicing would have to be ruled out before further study of candidate slow debranchers. As described above, YRA1 is an example of a gene that uses splicing inefficiency to regulate protein levels.

Quantitative RT-PCR of lariat RNAs can be used to determine the relative rates of transcription for different intron-containing genes. The use of intron RNA lariats as a novel data source for estimating relative levels of transcription for pre-mRNAs limits the utility to intron-containing genes, a notable limitation for *S. cerevisiae*. Furthermore, a Dbr1p-deficient strain would have to be used for intron lariats to be a stable record of transcription. Work with yeast dbr1 mutants over the years has not found any significant perturbation of cellular physiology other than the accumulation of intron RNA lariats. In the experiments shown in FIG. 7B-D, the level of RPP1B intron RNA in a dbr1 strain relative to the level in wild type is much greater (about 330-fold) than the corresponding levels of ACT1 and YRA1 intron RNAs (about 13-fold). These data indicate that the transcription rate for RPP1B is almost 30-fold greater than the rates for ACT1 and YRA1 (summarized in Table 3). These relative transcription rates are very different from estimates based on nuclear run-on assays, mRNA steady state levels plus half-lives, and DTA (Table 3).

TABLE 3

ACT1, YRA1, and RPP1B mRNA expression.

| Gene | Transcriptional frequency[a] | DTA[b] | | Relative intron levels[c] |
|---|---|---|---|---|
| ACT1 (YFL039C) | 45.5 [d] (1) | 7.2 [e] (1) | 63.2 (1) | 1.0 |
| YRA1 (YDR381W) | 16.2 [d] (0.4) | 80.6 [e] (11.2) | 88.9 (1.4) | 1.1 |
| RPP1B (YDL130W) | 120.0 [d] (2.6) | 23.0 [e] (3.2) | 192.7 (3) | 28.1 |

[a] mRNAs/cell/hr; numbers in parentheses are levels normalized to ACT1 level;
[b] DTA = dynamic transcriptome analysis, measured as mRNAs/cell/cell cycle time (150 min); numbers in parentheses are levels normalized to ACT1 level;
[c] Derived from data in FIG. 7 for the dbr1 null strain versus wild type for each gene and normalized to ACT1 level;
[d] Estimated from RNA expression levels and mRNA half-lives;
[e] Estimated from genomic run on experiments.

An area where the utility of excised introns is clearer is in determining relative rates of alternative splicing for a particular gene. Variable stabilities of different mRNAs confound estimates of their rate of synthesis, whether the synthesis that produces the mRNAs in question is transcription or alternative splicing. The use of a Dbr1p-deficient strain, which stabilizes the alternatively excised intron lariats equivalently, results in intron RNA lariat levels that directly reflect the rate of alternative splicing.

The methods described herein can also be applied to genome-wide analysis of introns themselves and are an improvement on previous analyses that also directly analyzed intron RNA lariats. RNA-seq of intron RNA lariat populations prepared using PNPase can provide complementary information to RNA-seq of whole transcriptomes and may reveal new lariat sequences not evident from transcriptome analysis alone. Intron RNA lariat levels can be greatly enhanced by blocking the RNA debranching reaction, which increases the likelihood of detecting even rare splicing events. Because cells defective for RNA debranching activity accumulate excised introns in their lariat forms, with shorted 3' tails, information on the 3' intron-exon junction is not obtainable from intron lariat RNA sequences. Nevertheless, lariat sequences provide information about branch points that is not obtainable from whole transcriptome sequencing. Such information is especially useful for studies of introns in organisms whose branch point sequences are not as highly conserved as those in *S. cerevisiae* [e.g. humans]. Finally, the absence of known intron sequences from an RNA population enriched-for RNA lariats can indicate that a gene is not expressed under the growth regimen employed. However, if an intron-containing gene is known to be expressed during the experiment, absence of intron sequences from the RNA lariat population could be an indication that the intron is removed by the hydrolytic splicing pathway observed for self splicing group II introns rather than the predominant branching pathway. High-throughput sequencing of enriched lariat RNAs from human cells is useful for much more detailed analysis of human branch point sequences.

Example 8: Amino Acid Conservation Among RNA Debranching Enzymes

Dbr1 is an RNA lariat debranching enzyme that hydrolyzes 2'-5' phosphodiester bonds at the branch points of excised intron lariats. The alignment model shown in FIG. 14 represents the N-terminal metallophosphatase domain of Dbr1. This domain belongs to the metallophosphatase (MPP) superfamily. MPPs are functionally diverse, but all share a conserved domain with an active site consisting of two metal ions (usually manganese, iron, or zinc) coordinated with octahedral geometry by a cage of histidine, aspartate, and asparagine residues. The MPP superfamily includes: Mre11/SbcD-like exonucleases, Dbr1-like RNA lariat debranching enzymes, YfcE-like phosphodiesterases, purple acid phosphatases (PAPs), YbbF-like UDP-2,3-diacylglucosamine hydrolases, and acid sphingomyelinases (ASMases). The conserved domain is a double beta-sheet sandwich with a di-metal active site made up of residues located at the C-terminal side of the sheets. This domain allows for productive metal coordination.

Example 9: Creation of an RNA Sample that is Highly Enriched for RNA Lariats

Figure 9:
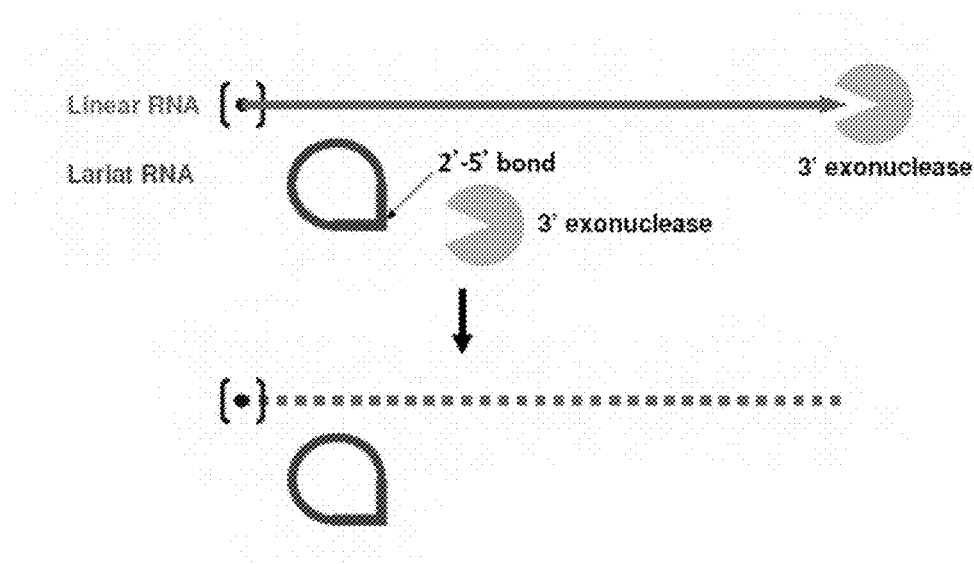
FIG. 9 illustrates the RNA lariat enrichment following treatment of an RNA sample with a 3' exonuclease. The parentheses at the left end of the linear RNA mean that these RNAs include both 5' capped and 5' uncapped species. The circular dot within the parentheses represents the cap. The arrow on the right side of the linear RNA represents the 3'end. Dashed lines represent degradation.
Figure 10:
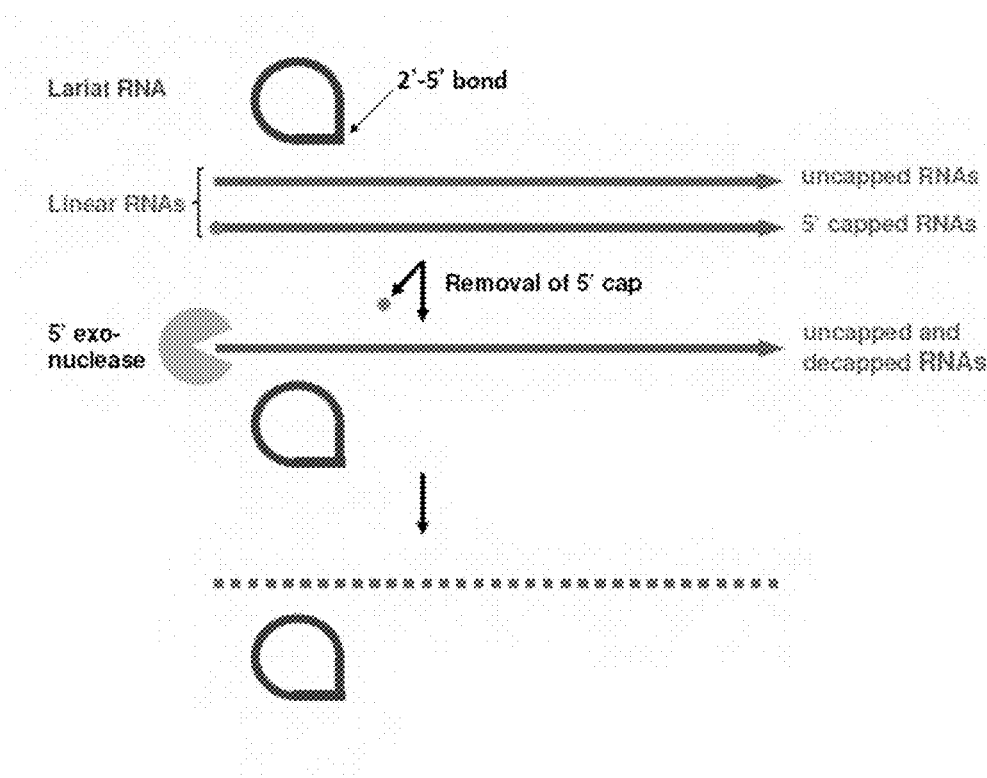
FIG. 10 illustrates the RNA lariat enrichment following treatment of a decapped RNA sample with a 5' exonuclease. Linear RNAs at the top, below the lariat RNA, are a mixture of 5' capped and 5' uncapped species. The circular dot at the left of the 5' capped RNA represents the cap. The arrows on the right side of the linear RNAs represent the 3' ends. Dashed lines represent degradation.

Linear and lariat RNAs have different sensitivities to exonucleolytic enzymes. Almost all linear RNAs are susceptible to complete or nearly complete degradation by enzymes that have 3' exonucleolytic activity. The key is to use an enzyme that is blocked by the lariat branch point and cannot degrade past the branch point. Such enzymes leave the lariat loop intact. Since lariat RNAs lack a 5' end, they are insensitive to 5' exonucleolytic activity; however, many linear RNAs are also sensitive to 5' exonucleolytic activity. Linear RNAs with 5' cap structures, which protect RNAs from 5' exonucleolytic activity, are made sensitive to 5' exonucleolytic activity by removing their caps. Cap removal treatments do not make lariat RNAs sensitive to exonucleases with 5' exonucleolytic activity. FIG. 9 and FIG. 10 illustrate the 3' and 5' exonucleolytic strategies, respectively, to create an RNA population that is highly enriched for RNA lariats.

Several methods may be employed to create an RNA population that is highly enriched for RNA lariats. Such methods include: 1) treat the RNA sample with a nuclease that has 3' exonucleolytic activity, a combination of nucleases with 3' exonucleolytic activity can also be used; 2) treat the RNA sample to remove the 5' cap structure from mRNAs, then treat with a nuclease that has 5' exonucleolytic activity, a combination of nucleases with 5' exonucleolytic activity can also be used; 3) treat the RNA sample with a nuclease that has both 5' and 3' exonucleolytic activity, with or without prior treatment to remove the 5' cap structure from mRNAs, a combination of nucleases, one or more with 5' exonucleolytic activity plus one or more with 3' exonucleolytic activity, can also be used.

To increase the proportion of lariat RNAs in the RNA population, RNA samples can be obtained from cells in which RNA debranching enzyme activity has been lowered or eliminated. Because the enhancement of RNA lariat levels in these cells is so dramatic, the resulting sample is useful for identifying RNA lariat species that are normally present at very low levels (i.e. in cells that have wild-type levels of RNA debranching enzyme activity). Another method that can be employed to increase the proportion of lariat RNAs in the RNA population being studied is to selectively remove rRNA species from the RNA sample prior to lariat RNA enrichment.

A control RNA sample that is depleted of lariat RNAs can be created and processed in parallel to the exonuclease-treated RNA sample to identify which RNAs are lariats in the exonuclease-resistant RNA population. The lariat depleted RNA sample is created by treatment of an RNA sample with RNA debranching enzyme prior to the exonucleolytic treatment protocol.

Following acquisition and treatment of RNA samples as outlined above, RNAs are processed for high-throughput sequencing. Although different platforms for high-throughput sequencing have been developed and continue to be developed, all of platforms involve parallel sequencing of large numbers of DNA fragments. All of these platforms are used for RNA sequencing by incorporating cDNA production protocols. The lariat-seq technique requires conversion of lariat-enriched RNA samples into cDNA populations, which are then processed for high-throughput sequencing according to the methods developed for the individual high-throughput sequencing platforms.

To aid in determining which cDNA sequences represent lariat RNAs, sequencing data resulting from experimental and control RNA samples are compared. RNAs originally in a lariat conformation will be represented at lower levels (proportionally and absolutely) in the control sample, resulting in a proportional (and absolute) reduction in the number of their corresponding cDNA sequences relative to the experimental sample. Some RNAs that are not in a lariat conformation in samples extracted from cells will survive the treatments to create an RNA population enriched for RNA lariats, for example RNAs with covalent modifications, other than a 2'-5' branch, that block the exonuclease used to create the experimental sample. These RNAs will be represented approximately equally (in absolute terms) in experimental and control samples. Selective removal of rRNA species from the RNA sample prior to lariat RNA enrichment, as stated above, will remove many RNAs that contain non-lariat covalent modifications that block the exonuclease.

Further evidence that a nuclease-resistant RNA identified by lariat-seq has a lariat conformation comes from signature cDNA products unique to lariat RNAs. Reverse transcriptase (RT) used for creating cDNA for sequencing is blocked by the presence of a 2' branch in an RNA substrate. However, when traveling along the branch segment itself, RT will read across the 2'-5' bond, creating cDNAs that juxtapose sequences that are not contiguous in the reference genome. Furthermore, when RT reads across the 2'-5' bond it inserts a nucleotide that is not expected according to Watson-Crick base pairing rules. Typically, for an intron lariat branch point, RT inserts an A opposite the branch point A instead of a T. Sequence reads that contain discontinuous genome segments with an unexpected nucleotide at the junction of the two segments are evidence that the cDNA was created from a lariat RNA.

Figure 11:
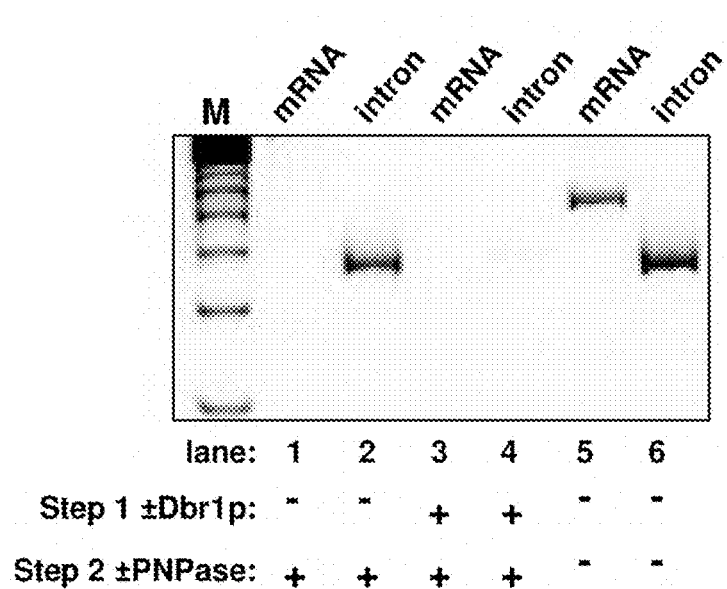
FIG. 11 illustrates RT-PCR detection of ACT1 mRNA (linear RNA) and intron (lariat RNA) in a total RNA sample from *Saccharomyces cerevisiae* cells following treatment with the 3' exonuclease polynucleotide phosphorylase (PNPase) (lanes 1 and 2), debranching enzyme (Dbr1p) followed by PNPase (lanes 3 and 4), and no treatment (lanes 5 and 6).

The different sensitivities of linear and lariat RNAs to the 3' exonuclease polynucleotide phosphorylase (PNPase) are shown in FIG. 11. Using RT-PCR to measure RNA levels, it is apparent that exonuclease treatment degrades a linear RNA down to the limit of detection while a lariat RNA remains virtually untouched (comparing lanes 1 and 2 (PNPase treatment) to lanes 5 and 6 (untreated)).

Figure 12:
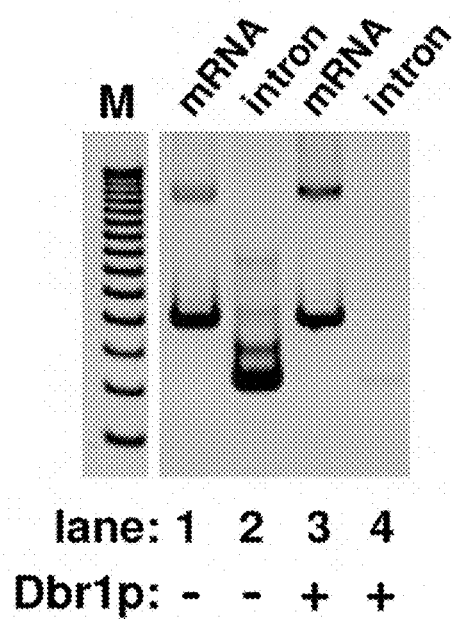
FIG. 12 illustrates the RT-PCR detection of ACT1 mRNA (linear RNA) and intron (lariat RNA) in total RNA samples from dbr1 mutant yeast cells following Dbr1p treatment (lanes 3 and 4) or no treatment (lanes 1 and 2).

Linear and lariat RNAs also have different sensitivities to RNA debranching enzyme, which can be exploited to confirm that an RNA species has a lariat conformation. In vitro cleavage of intron RNA lariats with purified S. cerevisiae Dbr1p is readily detectable with an RT-PCR assay, as shown in FIG. 12, lanes 3 and 4 (Dbr1p treatment) versus lanes 1 and 2 (untreated). For the RT-PCR in FIG. 12, a primer that spans the branch point was used for RT-PCR, which is why the intron signal is reduced upon Dbr1p treatment.

The use of sequential Dbr1p and PNPase treatments to explore the properties of a particular RNA species (control described above) is depicted in FIG. 11. As shown in FIG. 11, lanes 3 and 4 show the loss of a known lariat RNA when Dbr1p treatment precedes PNPase treatment. Compare to lanes 1 and 2 (PNPase treatment only) as well as lanes 5 and 6 (no treatment).

Figure 13A:
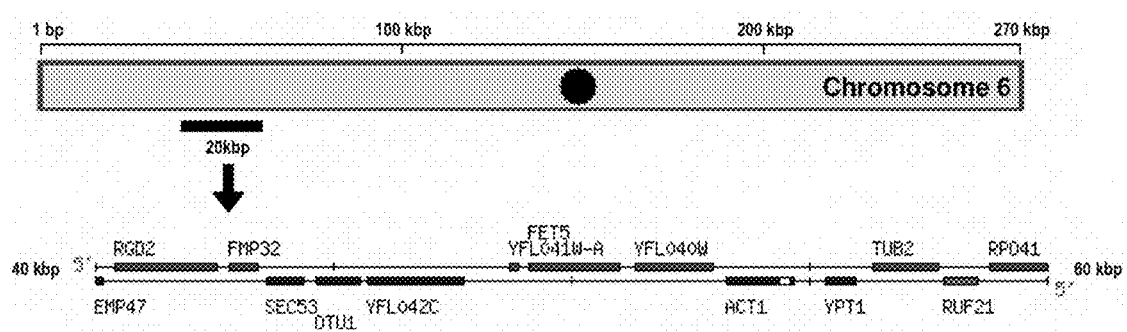
FIG. 13A,B illustrates the high-throughput sequencing of cDNAs representing PNPase-treated *S. cerevisiae* RNA.
Figure 13B:
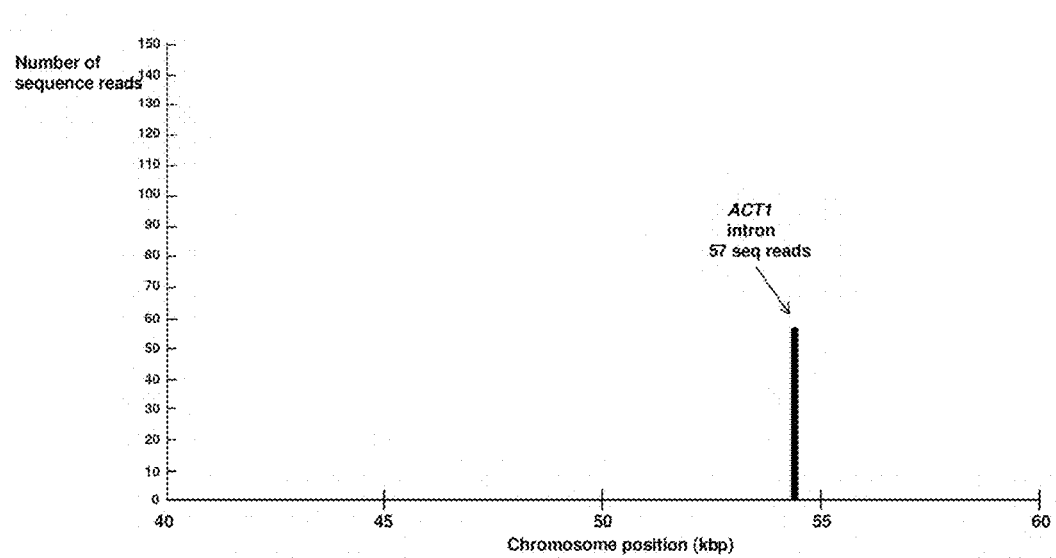
FIG. 13B graphically illustrates the number of sequence reads that map within the 20 kbp segment. The ACT1 gene is the only gene in this 20 kbp segment that contains an intron, which is depicted as a white box within the blue ACT1 ORF.

Data from high-throughput sequencing of cDNAs created from PNPase-treated RNA samples support the feasibility and operability of lariat-seq. Total S. cerevisiae RNA from a strain lacking a functioning RNA debranching enzyme was converted into cDNA after PNPase treatment and subjected to a high-throughput sequencing protocol (Illumina platform). An example of a small portion of the results obtained is depicted in FIG. 13, which shows the sequence reads that match to a segment of chromosome 6 (FIG. 13A). What is striking about the results is that the only sequence reads that map to this 20 kbp segment of the S. cerevisiae genome are from cDNAs that represent the intron region of the ACT1 gene (FIG. 13B). Furthermore, all these reads map within the sequences corresponding to the lariat loop of the intron; none of the sequence reads represent the 43 by that lie within the intron downstream of the lariat branch point. The fact that no sequence reads mapped to the ACT1 coding region or any other gene in the 20 kbp segment depicted in FIG. 13 indicates how efficiently the 3' exonuclease degraded the linear RNAs in the sample.

Example 10: RNA Lariat Enrichment Kit

The components necessary for RNA lariat enrichment can be provided in a kit for ease of use. An example of such a kit is described below. Variations of the kit are also contemplated.

Components of RNA lariat purification and analysis kit include the following: *Bacillus stearothermophilus* polynucleotide phosphorylase (BsPNPase); 2× BsPNPase reaction buffer: 100 mM Tris HCl, pH 8.5; 2 mM 2-mercaptoethanol; 2 mM EDTA; 40 mM KCl; 3 mM $MgCl_2$; 20 mM $Na_2HPO_4$, pH 8.3; *Saccharomyces cerevisiae* RNA debranching enzyme (ScDbr1); 10× ScDbr1 reaction buffer: 200 mM HEPES KOH (pH 7.9), 1.25 M KCl, 5 mM $MgCl_2$, 10 mM dithiothreitol; siRNAs (or siRNA sources) targeting mRNA for RNA debranching enzyme (different siRNA resources are packaged, depending on the organism for which the kit is specified); *Saccharomyces cerevisiae* total RNA samples (from dbr1 mutant and wild-type cells) for control RT-PCRs to assess lariat purification; primers for control RT-PCRs [to amplify ACT1 mRNA (linear RNA) and the ACT1 intron lariat RNA from *Saccharomyces cerevisiae* total RNA samples]; and, primers for control RT-PCRs for the organism for which the kit is specified [to amplify a known linear RNA and a known lariat RNA].

The kit also includes instructions of use. An example of such instructions includes the following:

1. Grow cells for RNA preparation. Two growth conditions can be used, one in which expression of endogenous RNA debranching enzyme is reduced, causing intron lariats to accumulate, and one in which the endogenous RNA debranching enzyme expression is unperturbed. If applicable, deploy the supplied siRNA resources to create cells with enhanced RNA lariat levels.
2. Harvest cells and purify total cellular RNA. Alternatively, store cells after harvesting for future RNA purification.
3. Treat 1 nanogram-10 micrograms of total RNA with 10 units of BsPNPase in 1× BsPNPase reaction buffer for 60 minutes at 60° C.
4. Incubate completed BsPNPase reactions at 85° C. for 10 minutes to inactivate the enzyme.
5. Phenol/chloroform extract RNA samples and ethanol precipitate them.
6. BsPNPase-treated RNA samples can be used for RT-PCRs of specific target RNAs (e.g. known linear and lariat RNAs) or for creation of cDNA libraries for Lariat-seq.

The kit may also include a control sample that is not enriched for RNA lariats. A control RNA sample that reflects the total RNA sample purified from cells is created by performing the above procedure but without BsPNPase in step 3.

The kit may also include a control sample that contains debranched RNA lariats. True lariat RNAs present in the BsPNPase-resistant RNA population will be sensitive to BsPNPase in RNA samples pretreated with ScDbr1.

1. Treat 1 nanogram-10 micrograms of total RNA with 10 units of ScDbr1 in 1× ScDbr1 reaction buffer in a 20 microliter reaction volume for 45 minutes at 30° C.
2. Incubate completed ScDbr1 reactions at 65° C. for 10 minutes to inactivate the enzyme.
3. Phenol/chloroform extract RNA samples and ethanol precipitate them. Resuspend RNAs in 1× BsPNPase reaction buffer.
4. Continue with BsPNPase treatment as described in steps 3-6 above (Procedure for creating purified RNA lariats).

In order to Confirm the enrichment of RNA lariats, control RT-PCRs for known linear and lariat RNAs are performed on treated RNA samples (both the samples enriched for RNA lariats and the control samples). Primers are provided for use with *Saccharomyces cerevisiae* RNA as well as for the organism for which the kit is specified.

Following treatment of RNA samples as outlined above (and confirmation of lariat-enrichment), RNAs are processed for high-throughput sequencing. The next step is to create a cDNA library from each treated RNA sample using procedures established for the high-throughput sequencing platform to be used (Illumina, SOLiD, etc). Materials for creating cDNA libraries are available from several different manufacturers.

*Bacillus stearothermophilus* polynucleotide phosphorylase (BsPNPase) storage buffer: 50% glycerol, 50 mM Tris-HCl (pH 8.5), 100 mM NaCl, 0.1 mM EDTA, 0.1% Triton X-100 and 1 mM dithiothreitol.

*Saccharomyces cerevisiae* RNA debranching enzyme (ScDbr1) storage buffer: 50% glycerol, 20 mM HEPES KOH (pH 7.9), 125 mM KCl, 0.5 mM MgCl2, 1 mM dithiothreitol.

One unit of BsPNPase activity is defined as the amount of PNPase that forms 1 μmol of ADP per hour at 60° C. by depolymerizing of Poly A.

One unit of ScDbr1 activity is defined as the amount of ScDbr1 that debranches 50% of the ACT1 intron present in 1 microgram of a total *Saccharomyces cerevisiae* RNA preparation (from mid-log phase cells) from a dbr1 mutant strain per hour at 30° C.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

Unless otherwise defined, all technical and scientific terms used herein have the same meaning as commonly understood by one of ordinary skill in the art. All publications, patent applications, patents, and other references mentioned herein are incorporated by reference in their entirety.

What is claimed is:

1. A method of enriching an RNA population for lariat RNA comprising:
   a. providing an RNA population isolated from a population of cells; and,
   b. contacting the RNA population with (i) a 5' cap removing enzyme followed by a 5' exonuclease, (ii) a 3' exonuclease and a 5' exonuclease with or without prior contact with a 5' cap removing enzyme, or (iii) a 5'/3' exonuclease with or without prior contact with a 5' cap removing enzyme to form a lariat RNA enriched population.

2. The method of claim 1, further comprising inhibiting a debranching enzyme in the population of cells prior to step (a).

3. The method of claim 2, wherein the debranching enzyme comprises an amino acid sequence having at least 35% sequence identity to a sequence selected from the group consisting of SEQ ID NO: 46-66.

4. The method of claim 3, wherein the sequence identity is selected from the group consisting of about 40, 45, 50, 55, 60, 65, 70, 75, 80, 81, 82, 83, 84, 85, 86, 87, 88, 89, 90, 91, 92, 93, 94, 95, 96, 97, 98 or 99%.

5. The method of claim 3, wherein the amino acid sequence has at least 75% sequence identity to the metallophosphatase domain of a sequence selected from the group consisting of SEQ ID NO: 46-66.

6. The method of claim 5, wherein the sequence identity is selected from the group consisting of about 40, 45, 50, 55, 60, 65, 70, 75, 80, 81, 82, 83, 84, 85, 86, 87, 88, 89, 90, 91, 92, 93, 94, 95, 96, 97, 98 or 99%.

7. A method of analyzing lariat RNA in an RNA sample comprising the steps of:
   a. providing an RNA population isolated from a population of cells;
   b. contacting the RNA population with (i) a 5' cap removing enzyme followed by a 5' exonuclease, (ii) a 3' exonuclease and a 5' exonuclease with or without prior contact with a 5' cap removing enzyme, or (iii) a 5'/3' exonuclease with or without prior contact with a 5' cap removing enzyme to form a lariat RNA enriched population; and,
   c. creating a cDNA library from the lariat RNA enriched population.

8. The method of claim 7, further comprising inhibiting a debranching enzyme in the population of cells prior to step (a).

9. The method of claim 8, wherein the debranching enzyme comprises an amino acid sequence having at least 35% sequence identity to a sequence selected from the group consisting of SEQ ID NO: 46-66.

10. The method of claim 9, wherein the sequence identity is selected from the group consisting of about 40, 45, 50, 55, 60, 65, 70, 75, 80, 81, 82, 83, 84, 85, 86, 87, 88, 89, 90, 91, 92, 93, 94, 95, 96, 97, 98 or 99%.

11. The method of claim 9, wherein the amino acid sequence has at least 75% sequence identity to the metallophosphatase domain of a sequence selected from the group consisting of SEQ ID NO: 46-66.

12. The method of claim 11, wherein the sequence identity is selected from the group consisting of about 40, 45, 50, 55, 60, 65, 70, 75, 80, 81, 82, 83, 84, 85, 86, 87, 88, 89, 90, 91, 92, 93, 94, 95, 96, 97, 98 or 99%.

13. The method of claim 7, further comprising sequencing the cDNA library.

* * * * *

SEQUENCE LISTING

<160> NUMBER OF SEQ ID NOS: 67

<210> SEQ ID NO 1
<211> LENGTH: 20
<212> TYPE: DNA
<213> ORGANISM: Artificial Sequence
<220> FEATURE:
<223> OTHER INFORMATION: PCR Primer, ACT1 intron nt 100-119

<400> SEQUENCE: 1

```
cactctccca taacctccta                                                    20

<210> SEQ ID NO 2
<211> LENGTH: 22
<212> TYPE: DNA
<213> ORGANISM: Artificial Sequence
<220> FEATURE:
<223> OTHER INFORMATION: PCR Primer, ACT1 nt -128 - -107

<400> SEQUENCE: 2
ctcaaaccaa gaagaaaaag aa                                                 22

<210> SEQ ID NO 3
<211> LENGTH: 22
<212> TYPE: DNA
<213> ORGANISM: Artificial Sequence
<220> FEATURE:
<223> OTHER INFORMATION: PCR Primer, ACT1 nt 130-109

<400> SEQUENCE: 3
tgataccttg gtgtcttggt ct                                                 22

<210> SEQ ID NO 4
<211> LENGTH: 21
<212> TYPE: DNA
<213> ORGANISM: Artificial Sequence
<220> FEATURE:
<223> OTHER INFORMATION: PCR Primer, -761 - -741 upstream of DBR1 ORF

<400> SEQUENCE: 4
aggatgtttc cgtctttaga a                                                  21

<210> SEQ ID NO 5
<211> LENGTH: 29
<212> TYPE: DNA
<213> ORGANISM: Artificial Sequence
<220> FEATURE:
<223> OTHER INFORMATION: PCR Primer, -10 - -30 upstream of DBR1 ORF,
      EcoRI site added at 5' end

<400> SEQUENCE: 5
gaggatcctg ataaatgtct gcccatctt                                          29

<210> SEQ ID NO 6
<211> LENGTH: 29
<212> TYPE: DNA
<213> ORGANISM: Artificial Sequence
<220> FEATURE:
<223> OTHER INFORMATION: PCR Primer, 16-30 after of DBR1 stop codon,
      XbaI site added at 5' end

<400> SEQUENCE: 6
gctctagaac gaatgcagac ggaattaga                                          29

<210> SEQ ID NO 7
<211> LENGTH: 36
<212> TYPE: DNA
<213> ORGANISM: Artificial Sequence
<220> FEATURE:
<223> OTHER INFORMATION: PCR Primer, 779-760 after of DBR1 stop codon,
      NotI site added at 5' end

<400> SEQUENCE: 7
ataagaatgc ggccgcaaag ggatccaatg tggtga                                  36
```

-continued

```
<210> SEQ ID NO 8
<211> LENGTH: 22
<212> TYPE: DNA
<213> ORGANISM: Artificial Sequence
<220> FEATURE:
<223> OTHER INFORMATION: PCR Primer, ACT1 intron nt 18-1, 265-262

<400> SEQUENCE: 8
gcaagcgcta gaacatactt ag                                              22

<210> SEQ ID NO 9
<211> LENGTH: 24
<212> TYPE: DNA
<213> ORGANISM: Artificial Sequence
<220> FEATURE:
<223> OTHER INFORMATION: PCR Primer, FLO8 nt 12-35

<400> SEQUENCE: 9
agtgaatagt tcgtatccag attc                                            24

<210> SEQ ID NO 10
<211> LENGTH: 21
<212> TYPE: DNA
<213> ORGANISM: Artificial Sequence
<220> FEATURE:
<223> OTHER INFORMATION: PCR Primer, FLO8 nt 418-398

<400> SEQUENCE: 10
catacaaaaa gccttgaggt g                                               21

<210> SEQ ID NO 11
<211> LENGTH: 24
<212> TYPE: DNA
<213> ORGANISM: Artificial Sequence
<220> FEATURE:
<223> OTHER INFORMATION: PCR Primer, FLO8 nt 422-445

<400> SEQUENCE: 11
ggtagcaaat attctgggac atct                                            24

<210> SEQ ID NO 12
<211> LENGTH: 22
<212> TYPE: DNA
<213> ORGANISM: Artificial Sequence
<220> FEATURE:
<223> OTHER INFORMATION: PCR Primer, FLO8 nt 837-816

<400> SEQUENCE: 12
attctgggtt ggccctacat tt                                              22

<210> SEQ ID NO 13
<211> LENGTH: 21
<212> TYPE: DNA
<213> ORGANISM: Artificial Sequence
<220> FEATURE:
<223> OTHER INFORMATION: PCR Primer, FLO8 nt 841-861

<400> SEQUENCE: 13
agtcaaaacg ttactggctg g                                               21

<210> SEQ ID NO 14
<211> LENGTH: 20
<212> TYPE: DNA
<213> ORGANISM: Artificial Sequence
<220> FEATURE:
<223> OTHER INFORMATION: PCR Primer, FLO8 nt 1260-1241
```

<400> SEQUENCE: 14
tgcttgattg cggaagttag                                               20

<210> SEQ ID NO 15
<211> LENGTH: 22
<212> TYPE: DNA
<213> ORGANISM: Artificial Sequence
<220> FEATURE:
<223> OTHER INFORMATION: PCR Primers, FLO8 nt 1268-1289

<400> SEQUENCE: 15
ttggcgagga agatatttat tc                                            22

<210> SEQ ID NO 16
<211> LENGTH: 25
<212> TYPE: DNA
<213> ORGANISM: Artificial Sequence
<220> FEATURE:
<223> OTHER INFORMATION: PCR Primers, FLO8 nt 1675-1652

<400> SEQUENCE: 16
aagataatgg actggataca gcscg                                         25

<210> SEQ ID NO 17
<211> LENGTH: 20
<212> TYPE: DNA
<213> ORGANISM: Artificial Sequence
<220> FEATURE:
<223> OTHER INFORMATION: PCR Primers, FLO8 nt 1693-1712

<400> SEQUENCE: 17
ttcgatccag aaagtggcaa                                               20

<210> SEQ ID NO 18
<211> LENGTH: 24
<212> TYPE: DNA
<213> ORGANISM: Artificial Sequence
<220> FEATURE:
<223> OTHER INFORMATION: PCR Primers, FLO8 nt 2036-2013

<400> SEQUENCE: 18
ttttcctctg gagtagataa tgtg                                          24

<210> SEQ ID NO 19
<211> LENGTH: 22
<212> TYPE: DNA
<213> ORGANISM: Artificial Sequence
<220> FEATURE:
<223> OTHER INFORMATION: PCR Primers, FLO8 nt 2054-2075

<400> SEQUENCE: 19
atcaaggata tgattttgac gc                                            22

<210> SEQ ID NO 20
<211> LENGTH: 24
<212> TYPE: DNA
<213> ORGANISM: Artificial Sequence
<220> FEATURE:
<223> OTHER INFORMATION: PCR Primers, FLO8 nt 2399-2376

<400> SEQUENCE: 20
cagccttccc aattaataaa attg                                          24

<210> SEQ ID NO 21
<211> LENGTH: 22

```
<212> TYPE: DNA
<213> ORGANISM: Artificial Sequence
<220> FEATURE:
<223> OTHER INFORMATION: PCR Primers, URA3 nt 67-46

<400> SEQUENCE: 21
taaatagctt ggcagcaaca gg                                         22

<210> SEQ ID NO 22
<211> LENGTH: 20
<212> TYPE: DNA
<213> ORGANISM: Artificial Sequence
<220> FEATURE:
<223> OTHER INFORMATION: PCR Primers, DBR1 nt 10-29

<400> SEQUENCE: 22
ttgcgaattg ctgtacaagg                                            20

<210> SEQ ID NO 23
<211> LENGTH: 26
<212> TYPE: DNA
<213> ORGANISM: Artificial Sequence
<220> FEATURE:
<223> OTHER INFORMATION: PCR Primers, DBR1 nt 1217-1192

<400> SEQUENCE: 23
caagtcatga atttagagat aaatgc                                     26

<210> SEQ ID NO 24
<211> LENGTH: 40
<212> TYPE: DNA
<213> ORGANISM: Artificial Sequence
<220> FEATURE:
<223> OTHER INFORMATION: PCR Primers, 5' 40 nt = DBR1 nt 31-70

<400> SEQUENCE: 24
tgctgtcatg gtcagctaaa ccaaatttat aaagaagtgt                      40

<210> SEQ ID NO 25
<211> LENGTH: 20
<212> TYPE: DNA
<213> ORGANISM: Artificial Sequence
<220> FEATURE:
<223> OTHER INFORMATION: PCR Primers, 3' 20 nt = URA3 flank in pRS306

<400> SEQUENCE: 25
taactatgcg gcatcagagc                                            20

<210> SEQ ID NO 26
<211> LENGTH: 40
<212> TYPE: DNA
<213> ORGANISM: Artificial Sequence
<220> FEATURE:
<223> OTHER INFORMATION: PCR Primers, 5' 40 nt = DBR1 nt 1200-1161

<400> SEQUENCE: 26
gataaatgct ttagtttgtc gtacttcatc tttctgaata                      40

<210> SEQ ID NO 27
<211> LENGTH: 20
<212> TYPE: DNA
<213> ORGANISM: Artificial Sequence
<220> FEATURE:
<223> OTHER INFORMATION: PCR Primers, 3' 20 nt = URA3 flank in pRS306

<400> SEQUENCE: 27
```
cctgatgcgg tattttctcc                                              20

<210> SEQ ID NO 28
<211> LENGTH: 25
<212> TYPE: DNA
<213> ORGANISM: Artificial Sequence
<220> FEATURE:
<223> OTHER INFORMATION: qRT-PCR Primers, FWD Primer

<400> SEQUENCE: 28
tcccaagatc gaaaatttac tgaat                                        25

<210> SEQ ID NO 29
<211> LENGTH: 27
<212> TYPE: DNA
<213> ORGANISM: Artificial Sequence
<220> FEATURE:
<223> OTHER INFORMATION: qRT-PCR Primers, Reverse primer at position
      54-28

<400> SEQUENCE: 29
tttacacata ccagaaccgt tatcaat                                      27

<210> SEQ ID NO 30
<211> LENGTH: 21
<212> TYPE: DNA
<213> ORGANISM: Artificial Sequence
<220> FEATURE:
<223> OTHER INFORMATION: qRT-PCR Probe, TaqMan probe at position -4 to
      26

<400> SEQUENCE: 30
tgaattaaca aggttgctgc t                                            21

<210> SEQ ID NO 31
<211> LENGTH: 28
<212> TYPE: DNA
<213> ORGANISM: Artificial Sequence
<220> FEATURE:
<223> OTHER INFORMATION: qRT-PCR Primers, FWD Primer at position 94-121

<400> SEQUENCE: 31 attttttcact ctcccataac ctcctata                                    28

<210> SEQ ID NO 32
<211> LENGTH: 24
<212> TYPE: DNA
<213> ORGANISM: Artificial Sequence
<220> FEATURE:
<223> OTHER INFORMATION: qRT-PCR Primers, Reverse primer at position
      173-150

<400> SEQUENCE: 32
tttcaagccc ctatttattc caat                                         24

<210> SEQ ID NO 33
<211> LENGTH: 20
<212> TYPE: DNA
<213> ORGANISM: Artificial Sequence
<220> FEATURE:
<223> OTHER INFORMATION: qRT-PCR Probe, TaqMan probe at position 123-142

<400> SEQUENCE: 33
tgactgatct gtaataacca                                              20

<210> SEQ ID NO 34

-continued

```
<211> LENGTH: 18
<212> TYPE: DNA
<213> ORGANISM: Artificial Sequence
<220> FEATURE:
<223> OTHER INFORMATION: qRT-PCR Primers, FWD Primer at position 89-106

<400> SEQUENCE: 34
aggccgctgg tgctaatg                                                     18

<210> SEQ ID NO 35
<211> LENGTH: 23
<212> TYPE: DNA
<213> ORGANISM: Artificial Sequence
<220> FEATURE:
<223> OTHER INFORMATION: qRT-PCR Primers, Reverse primer at position
      146-124

<400> SEQUENCE: 35
tccaaagcct tagcgtaaac atc                                               23

<210> SEQ ID NO 36
<211> LENGTH: 15
<212> TYPE: DNA
<213> ORGANISM: Artificial Sequence
<220> FEATURE:
<223> OTHER INFORMATION: qRT-PCR Probe, TaqMan probe at position 108-122

<400> SEQUENCE: 36
cgacaacgtc tgggc                                                        15

<210> SEQ ID NO 37
<211> LENGTH: 24
<212> TYPE: DNA
<213> ORGANISM: Artificial Sequence
<220> FEATURE:
<223> OTHER INFORMATION: qRT-PCR Primers, FWD Primer at position 12-35

<400> SEQUENCE: 37
aatgcaacct aaaacgactt tgtg                                              24

<210> SEQ ID NO 38
<211> LENGTH: 21
<212> TYPE: DNA
<213> ORGANISM: Artificial Sequence
<220> FEATURE:
<223> OTHER INFORMATION: qRT-PCR Primers, Reverse primer at position
      77-57

<400> SEQUENCE: 38
tttctcggga cgattgttgt c                                                 21

<210> SEQ ID NO 39
<211> LENGTH: 18
<212> TYPE: DNA
<213> ORGANISM: Artificial Sequence
<220> FEATURE:
<223> OTHER INFORMATION: qRT-PCT Primer, TaqMan probe at position 38-55

<400> SEQUENCE: 39
actacgaaga gaaagatt                                                     18

<210> SEQ ID NO 40
<211> LENGTH: 22
<212> TYPE: DNA
<213> ORGANISM: Artificial Sequence
<220> FEATURE:
<223> OTHER INFORMATION: qRT-PCR Primers, FWD Primer at position 249-270
```

-continued

<400> SEQUENCE: 40
aggtttgcca agggacatta ag                                              22

<210> SEQ ID NO 41
<211> LENGTH: 24
<212> TYPE: DNA
<213> ORGANISM: Artificial Sequence
<220> FEATURE:
<223> OTHER INFORMATION: qRT-PCR Primers, Reverse primer at position
      314-291

<400> SEQUENCE: 41
acaccaccta cttgagatgc aaaa                                            24

<210> SEQ ID NO 42
<211> LENGTH: 18
<212> TYPE: DNA
<213> ORGANISM: Artificial Sequence
<220> FEATURE:
<223> OTHER INFORMATION: qRT-PCT Primer, TaqMan probe at position
      272-289

<400> SEQUENCE: 42
aggatgctgt aagagaat                                                   18

<210> SEQ ID NO 43
<211> LENGTH: 19
<212> TYPE: DNA
<213> ORGANISM: Artificial Sequence
<220> FEATURE:
<223> OTHER INFORMATION: qRT-PCR Primers, FWD Primer at position 42-60

<400> SEQUENCE: 43
cgcatcgtct cgtgtggat                                                  19

<210> SEQ ID NO 44
<211> LENGTH: 22
<212> TYPE: DNA
<213> ORGANISM: Artificial Sequence
<220> FEATURE:
<223> OTHER INFORMATION: qRT-PCR Primers, Reverse primer at position
      107-86

<400> SEQUENCE: 44
gatcaaaagc gtgtgccata tc                                              22

<210> SEQ ID NO 45
<211> LENGTH: 23
<212> TYPE: DNA
<213> ORGANISM: Artificial Sequence
<220> FEATURE:
<223> OTHER INFORMATION: qRT-PCT Primer, TaqMan probe at position 62-84

<400> SEQUENCE: 45
cgagaaatat tctttgtaag gaa                                             23

<210> SEQ ID NO 46
<211> LENGTH: 544
<212> TYPE: PRT
<213> ORGANISM: Homo sapiens

<400> SEQUENCE: 46

Met Arg Val Ala Val Ala Gly Cys Cys His Gly Glu Leu Asp Lys Ile
1               5                   10                  15

```
Tyr Glu Thr Leu Ala Leu Ala Glu Arg Arg Gly Pro Gly Pro Val Asp
             20                  25                  30

Leu Leu Leu Cys Cys Gly Asp Phe Gln Ala Val Arg Asn Glu Ala Asp
         35                  40                  45

Leu Arg Cys Met Ala Val Pro Pro Lys Tyr Arg His Met Gln Thr Phe
     50                  55                  60

Tyr Arg Tyr Tyr Ser Gly Glu Lys Lys Ala Pro Val Leu Thr Leu Phe
 65                  70                  75                  80

Ile Gly Gly Asn His Glu Ala Ser Asn His Leu Gln Glu Leu Pro Tyr
                 85                  90                  95

Gly Gly Trp Val Ala Pro Asn Ile Tyr Tyr Leu Gly Leu Ala Gly Val
                100                 105                 110

Val Lys Tyr Arg Gly Val Arg Ile Gly Gly Ile Ser Gly Ile Phe Lys
         115                 120                 125

Ser His Asp Tyr Arg Lys Gly His Phe Glu Cys Pro Pro Tyr Asn Ser
    130                 135                 140

Ser Thr Ile Arg Ser Ile Tyr His Val Arg Asn Ile Glu Val Tyr Lys
145                 150                 155                 160

Leu Lys Gln Leu Lys Gln Pro Ile Asp Ile Phe Leu Ser His Asp Trp
                165                 170                 175

Pro Arg Ser Ile Tyr His Tyr Gly Asn Lys Lys Gln Leu Leu Lys Thr
            180                 185                 190

Lys Ser Phe Phe Arg Gln Glu Val Glu Asn Asn Thr Leu Gly Ser Pro
        195                 200                 205

Ala Ala Ser Glu Leu Leu Glu His Leu Lys Pro Thr Tyr Trp Phe Ser
210                 215                 220

Ala His Leu His Val Lys Phe Ala Ala Leu Met Gln His Gln Ala Lys
225                 230                 235                 240

Asp Lys Gly Gln Thr Ala Arg Ala Thr Lys Phe Leu Ala Leu Asp Lys
                245                 250                 255

Cys Leu Pro His Arg Asp Phe Leu Gln Ile Leu Glu Ile Glu His Asp
            260                 265                 270

Pro Ser Ala Pro Asp Tyr Leu Glu Tyr Asp Ile Glu Trp Leu Thr Ile
        275                 280                 285

Leu Arg Ala Thr Asp Asp Leu Ile Asn Val Thr Gly Arg Leu Trp Asn
290                 295                 300

Met Pro Glu Asn Asn Gly Leu His Ala Arg Trp Asp Tyr Ser Ala Thr
305                 310                 315                 320

Glu Glu Gly Met Lys Glu Val Leu Glu Lys Leu Asn His Asp Leu Lys
                325                 330                 335

Val Pro Cys Asn Phe Ser Val Thr Ala Ala Cys Tyr Asp Pro Ser Lys
            340                 345                 350

Pro Gln Thr Gln Met Gln Leu Ile His Arg Ile Asn Pro Gln Thr Thr
        355                 360                 365

Glu Phe Cys Ala Gln Leu Gly Ile Ile Asp Ile Asn Val Arg Leu Gln
    370                 375                 380

Lys Ser Lys Glu Glu His His Val Cys Gly Glu Tyr Glu Glu Gln Asp
385                 390                 395                 400

Asp Val Glu Ser Asn Asp Ser Gly Glu Asp Gln Ser Glu Tyr Asn Thr
                405                 410                 415

Asp Thr Ser Ala Leu Ser Ser Ile Asn Pro Asp Glu Ile Met Leu Asp
            420                 425                 430

Glu Glu Glu Asp Glu Asp Ser Ile Val Ser Ala His Ser Gly Met Asn
```

```
                  435                 440                 445
Thr Thr Ile Gly Arg Ser Leu Leu Ile Lys Leu Leu Ser Phe Cys Ser
    450                 455                 460

Phe Ser Asp Val Arg Ile Leu Pro Gly Ser Met Ile Val Ser Ser Asp
465                 470                 475                 480

Asp Thr Val Asp Ser Thr Ile Asp Arg Glu Gly Lys Pro Gly Gly Leu
                    485                 490                 495

Val Glu Ser Gly Asn Gly Glu Asp Leu Thr Lys Val Pro Leu Lys Arg
                500                 505                 510

Leu Ser Asp Glu His Glu Pro Glu Gln Arg Lys Lys Ile Lys Arg Arg
            515                 520                 525

Asn Gln Ala Ile Tyr Ala Ala Val Asp Asp Asp Asp Ala Ala
        530                 535                 540

<210> SEQ ID NO 47
<211> LENGTH: 405
<212> TYPE: PRT
<213> ORGANISM: Saccharomyces cerevisiae

<400> SEQUENCE: 47

Met Thr Lys Leu Arg Ile Ala Val Gln Gly Cys Cys His Gly Gln Leu
1               5                   10                  15

Asn Gln Ile Tyr Lys Glu Val Ser Arg Ile His Ala Lys Thr Pro Ile
                20                  25                  30

Asp Leu Leu Ile Ile Leu Gly Asp Phe Gln Ser Ile Arg Asp Gly Gln
                35                  40                  45

Asp Phe Lys Ser Ile Ala Ile Pro Pro Lys Tyr Gln Arg Leu Gly Asp
        50                  55                  60

Phe Ile Ser Tyr Tyr Asn Asn Glu Ile Glu Ala Pro Val Pro Thr Ile
65                  70                  75                  80

Phe Ile Gly Gly Asn His Glu Ser Met Arg His Leu Met Leu Leu Pro
                85                  90                  95

His Gly Gly Tyr Val Ala Lys Asn Ile Phe Tyr Met Gly Tyr Ser Asn
                100                 105                 110

Val Ile Trp Phe Lys Gly Ile Arg Ile Gly Ser Leu Ser Gly Ile Trp
            115                 120                 125

Lys Glu Trp Asp Phe Asn Lys Gln Arg Pro Asp Trp Asn Asp Leu Glu
130                 135                 140

Asn Asn Asn Trp Lys Ala Asn Ile Arg Asn Leu Tyr His Val Arg Ile
145                 150                 155                 160

Ser Asp Ile Ala Pro Leu Phe Met Ile Lys His Arg Ile Asp Ile Met
                165                 170                 175

Leu Ser His Asp Trp Pro Asn Gly Val Val Tyr His Gly Asp Thr Lys
            180                 185                 190

His Leu Leu Lys Leu Lys Pro Phe Phe Glu Gln Asp Ile Lys Glu Gly
        195                 200                 205

Lys Leu Gly Ser Pro Val Thr Trp Gln Leu Leu Arg Asp Leu Arg Pro
    210                 215                 220

Gln Trp Trp Leu Ser Ala His Leu His Val Arg Phe Met Ala Ser Ile
225                 230                 235                 240

Lys His Asn Lys Arg Ser His Glu Pro Pro Asn Lys Ser Thr Ser Lys
                245                 250                 255

Thr Lys Lys Asn Asn Asn Glu Ile Asp Leu Asp Leu Ser Ser Asp Glu
                260                 265                 270
```

-continued

```
Asp Glu Arg Ser Gly Ile Met Asn Cys Gln Glu Asn Glu Tyr Asp
            275                 280                 285
Ser Lys Tyr Gly Glu Thr Arg Phe Leu Ala Leu Asp Lys Cys Leu Pro
290                 295                 300
Arg Arg Arg Trp Leu Glu Ile Leu Glu Ile Glu Pro Asp Thr Ser His
305                 310                 315                 320
Ala Ser Trp Lys Asp Glu Asn His Arg Met Phe Trp Asp Pro Glu Phe
                325                 330                 335
Ile Asn Asn Leu Val Ile Cys Gln Lys Asn Lys Asn Leu Leu Ser Asn
            340                 345                 350
Lys Pro Phe Asn Ser Val Asn Trp Ile Glu Leu Ser Gln Ser Asn Arg
        355                 360                 365
Glu Glu Gly Arg Asp Ile Asp Trp Glu Asn Tyr Ala Ile Pro Ala Tyr
370                 375                 380
Thr Leu Asp Ile Gln Lys Asp Glu Val Arg Gln Thr Lys Ala Phe Ile
385                 390                 395                 400
Ser Lys Phe Met Thr
                405

<210> SEQ ID NO 48
<211> LENGTH: 479
<212> TYPE: PRT
<213> ORGANISM: Candida albicans

<400> SEQUENCE: 48

Met Arg Asn Thr Ile Tyr Lys His Ser Ser Ile Val Thr Ala Met Ser
1               5                   10                  15
Asn Thr Leu Lys Ile Ala Ile Glu Gly Cys Cys His Gly Glu Leu Asn
            20                  25                  30
Asp Ile Tyr Asn Ser Ile Pro Asp Ile Glu Ser Leu Asp Leu Leu
            35                  40                  45
Ile Cys Gly Asp Phe Gln Ser Leu Arg Asn Lys Cys Asp Leu Gln Ser
    50                  55                  60
Leu Asn Val Pro Leu Lys Tyr Gln Arg Met Ala Asp Phe His Glu Tyr
65                  70                  75                  80
Tyr Ser Gly Lys Arg Lys Ala Pro Val Leu Thr Ile Phe Ile Gly Gly
                85                  90                  95
Asn His Glu Cys Ser Ser Tyr Leu Gln Glu Leu Lys Tyr Gly Gly Trp
            100                 105                 110
Val Ala Pro Asn Ile Tyr Tyr Leu Gly Glu Phe Gly Ser Ile Trp Tyr
        115                 120                 125
Lys Gly Leu Gln Ile Thr Gly Trp Ser Gly Ile Phe Asn Tyr His Thr
    130                 135                 140
Phe Ile Ala Asn Asn Ile Glu Met Glu Lys Leu Pro Phe Asp Ser Arg
145                 150                 155                 160
Thr Ile Arg Ser Val Tyr His Gln Lys Leu Ala Asn Phe Leu Lys Met
                165                 170                 175
Tyr Met Met Asn His Asp Met Asp Ile Val Leu Ser His Asp Trp Pro
            180                 185                 190
Val Gly Ile Glu Lys Tyr Gly Asn Val Lys Arg Leu Leu Lys Leu Lys
        195                 200                 205
Pro Phe Phe Arg Asp Asp Ile Gln Arg Gly Gln Leu Gly Ser Pro Leu
    210                 215                 220
Asn Lys Phe Leu Ile His Tyr Leu Arg Pro Arg Tyr Trp Phe Ser Gly
225                 230                 235                 240
```

His Leu His Val Lys Phe Glu Ala Arg Ile Val Asp Leu Val Arg Ser
                245                 250                 255

Thr Asp Lys Lys Lys Ser Ala Thr Thr Val Asp Leu Ile Thr Glu Ser
            260                 265                 270

Asn Lys Glu Glu Ile Ser Leu Asp Met Asp Glu Glu Glu Glu
        275                 280                 285

Gly Gly Asn Val Arg Glu Val Ser Phe Glu Glu Lys Phe Tyr Phe Lys
    290                 295                 300

Gln His Ser Asn Pro Ala Lys Arg Pro Lys Asn Asp Leu Thr Pro Glu
305                 310                 315                 320

Arg Asp Val Cys Glu His Ala Thr Glu Phe Leu Ala Leu Asp Lys Cys
                325                 330                 335

Gly Lys Arg Arg Gln Phe Leu Asp Ile Lys Thr Ile Glu Val His Asn
            340                 345                 350

Thr Ser His Pro Ser Phe Ile Asn Ala Gly Lys Leu Tyr Tyr Ser Lys
        355                 360                 365

Arg Ser Ile Ala Ile Asn Lys Val Val Glu Lys Tyr Leu Asn Asp Asn
370                 375                 380

Arg Gln Asp Phe Thr Glu Leu Asn Thr Lys Gln Ile Leu Ser Asn Pro
385                 390                 395                 400

Gln Gln Phe Pro Leu Val Asn Glu Leu Met Pro Ile Ile Glu Asn Asp
                405                 410                 415

Phe Lys Ser Met Gln Lys Asn Ile Thr Asp Glu Asp Phe Phe Met Val
            420                 425                 430

Pro Glu Asn Phe Gln Thr Ile Ala Pro Thr Asp Glu His Thr Glu
        435                 440                 445

Ser Lys Leu Lys Tyr Tyr Pro Asn Asn Gln Thr Ser Glu Tyr Cys Glu
    450                 455                 460

Lys Phe Gly Ile Pro Lys Leu Val Leu Ser Lys Glu Ser Asp Gln
465                 470                 475

<210> SEQ ID NO 49
<211> LENGTH: 405
<212> TYPE: PRT
<213> ORGANISM: Candida glabrata

<400> SEQUENCE: 49

Met Asn Glu Arg Lys Leu Arg Ile Ala Val Gln Gly Cys Cys His Gly
1               5                   10                  15

Glu Leu Asn Lys Val Phe Ala Thr Val Ala Asp Met His Lys Arg Thr
            20                  25                  30

Pro Ile Asp Leu Leu Ile Ile Leu Gly Asp Phe Gln Ser Ile Arg Asp
        35                  40                  45

Asn Ser Asp Phe Gln Ser Ile Ser Ile Pro Pro Lys Tyr Gln Lys Leu
    50                  55                  60

Gly Asp Phe His Ala Tyr Tyr Glu Asn Asp Tyr Tyr Arg Ala Pro Val
65                  70                  75                  80

Phe Thr Ile Val Ile Gly Gly Asn His Glu Ser Met Arg His Leu Met
                85                  90                  95

Gln Leu Pro Tyr Gly Gly Tyr Leu Ala Asn Asn Ile Tyr Met Gly
            100                 105                 110

Tyr Ser Gly Val Val Trp Phe Lys Gly Phe Arg Ile Ala Ala Leu Ser
        115                 120                 125

Gly Ile Trp Lys Glu Trp Asp Phe Glu Lys Lys Arg Pro Ser Trp Lys

-continued

```
                130                 135                 140
    Phe Leu Glu Glu Asn Asn Lys Trp Lys Asp Ser Val Arg Gln Leu Tyr
    145                 150                 155                 160

His Ile Arg Lys Asp Asp Val Ala Pro Leu Phe Ala Leu Ser Asp Asn
                    165                 170                 175

Ile Asp Ile Cys Leu Ser His Asp Trp Pro Ser Gly Val Val His Tyr
                180                 185                 190

Gly Asn Val Lys Gln Leu Leu Lys Tyr Lys Pro Phe Phe Glu Lys Asp
                    195                 200                 205

Ile Lys Ser Gly Lys Leu Gly Asn Pro Ile Ala Trp Lys Leu Leu Thr
    210                 215                 220

Asn Leu Lys Pro Arg Trp Trp Phe Ser Ala His Leu His Val Lys Tyr
    225                 230                 235                 240

Glu Ala Glu Ile Thr His Asn Lys Arg Arg Leu Ala Asp Ser Lys Gly
                    245                 250                 255

Ala Lys Lys Leu Lys Ser Asn Ser Asp Glu Ile Glu Leu Asn Leu Asp
                260                 265                 270

Asp Glu Ser Ser Leu Asp Leu Ser Cys His Asp Ser Leu Asp Ser
    275                 280                 285

Ala Glu His Thr Arg Phe Leu Ser Leu Asp Lys Cys Met Pro Arg Arg
    290                 295                 300

Lys Trp Leu Glu Ile Val Glu Ile Glu Lys Arg Tyr Asp Ser Ile Pro
    305                 310                 315                 320

Gln Gly Leu Asp Cys Asp Lys Met Tyr Trp Asp Pro Ser Tyr Ile Ile
                    325                 330                 335

Ala Leu Gln Asn Leu Glu Lys Gln Ser Arg Leu Val Ala Asp Thr Pro
                340                 345                 350

Phe Asn Glu Ile Ile Trp Ser Arg Phe Ser Ser Gly His Ile Asp Asp
                    355                 360                 365

Ile Asn Trp His Lys Tyr Glu Ile Pro Lys Tyr Glu Ser Gly Leu Gln
                370                 375                 380

Arg Asp Glu Ala Ser Gln Thr Asn Tyr Phe Leu Ser Lys His Met Leu
    385                 390                 395                 400

Ser Lys Gly Ser Arg
                    405

<210> SEQ ID NO 50
<211> LENGTH: 417
<212> TYPE: PRT
<213> ORGANISM: Candida parapsilosis

<400> SEQUENCE: 50

Met Lys Thr Leu Lys Val Ala Ile Glu Gly Cys Cys His Gly Asp Leu
    1               5                   10                  15

Asn Lys Ile Tyr Lys Gly Ile Pro Ser Ser Thr Glu Leu Leu Leu Ile
                    20                  25                  30

Cys Gly Asp Phe Gln Ala Leu Arg Asn Thr Ser Asp Tyr Gln Ala Leu
                35                  40                  45

Ser Val Pro Glu Lys Tyr Arg Arg Leu Gly Asp Phe Gln Ser Tyr Tyr
            50                  55                  60

Thr Ser Lys Lys Lys Ala Pro Val Leu Thr Ile Phe Ile Gly Gly Asn
    65                  70                  75                  80

His Glu Ser Ser Ser Tyr Leu Gln Glu Leu Lys Tyr Gly Gly Trp Val
                    85                  90                  95
```

Ala Pro Asn Ile Tyr Tyr Leu Gly Glu Phe Gly Ser Val His Tyr Lys
            100                 105                 110

Gly Leu Ser Ile Cys Gly Trp Ser Gly Ile Tyr Asn Pro His Thr Tyr
        115                 120                 125

Met Asn Lys Ser Phe Asn Val Glu Arg Leu Pro Phe Asp Ser Asn Ser
    130                 135                 140

Ile Arg Ser Val Tyr His Gln Lys Leu Ser Asn Phe Leu Lys Met Tyr
145                 150                 155                 160

Leu Gln Arg Asp Met Asp Ile Val Leu Ser His Asp Trp Pro Val Gly
                165                 170                 175

Ile Glu Lys Phe Gly Asp Lys Tyr Arg Leu Leu Lys Gln Lys Pro Phe
            180                 185                 190

Phe Thr Gln Asp Ile Lys Lys Gly Gln Leu Gly Ser Pro Leu Asn Asn
        195                 200                 205

Val Leu Leu His His Leu Lys Pro Arg Tyr Trp Phe Ser Gly His Leu
    210                 215                 220

His Val Lys Phe Lys Ala Asn Val Asn His Asn Ile Ser Lys Pro Lys
225                 230                 235                 240

Gln Val Lys Asn Ala Asn Glu Ile Leu Leu Asp Met Glu Ser Ser Asp
                245                 250                 255

Glu Ala Ser Asp Gly Glu Asn Gln Pro Gln Lys Lys Met Lys Pro Asn
            260                 265                 270

Gly His Val Val His Asp Thr Gln Phe Leu Ala Leu Asp Lys Tyr Gly
        275                 280                 285

Pro Arg Arg Ser Tyr Phe Glu Val Ile Asn Ile Pro Ile Leu Glu Asn
    290                 295                 300

Asn His Pro Ser Val His Asp Gly Leu Tyr Tyr Asp Lys Arg Ala
305                 310                 315                 320

Ile Ala Ile Asn Arg Val Val Glu Lys Tyr Arg Ile Asp Gln Lys Thr
                325                 330                 335

Glu Phe Glu Ser Met Ser Pro Arg Glu Ile Leu Arg Asp Pro Arg Lys
            340                 345                 350

Leu Glu Lys Phe Ile Pro Leu Val Ala Lys Glu Ser Glu Glu Ile Asn
        355                 360                 365

Gln Ile Asp Asp Asn Gln Phe Val Ile Pro Lys Asn Phe Glu Val Val
    370                 375                 380

Ala Pro Ala Asp Tyr Asp Gly Glu Leu Lys Tyr Tyr Pro Asn Ala Gln
385                 390                 395                 400

Thr Glu Glu Tyr Cys Arg Lys Phe Gly Ile Pro Gln Gln Asp Tyr Gln
                405                 410                 415

Leu

<210> SEQ ID NO 51
<211> LENGTH: 746
<212> TYPE: PRT
<213> ORGANISM: Histoplasma capsulatum

<400> SEQUENCE: 51

Met Gln His Ile Pro Ala Ser Pro Ser Arg Asn Leu Arg Val Ala Leu
1               5                   10                  15

Glu Gly Cys Lys Tyr Lys Gln Ile Gly Asp Phe His Glu Tyr Tyr Ser
                20                  25                  30

Gly Ala Arg Val Ala Pro Tyr Leu Thr Ile Phe Val Gly Gly Asn His
            35                  40                  45

-continued

```
Glu Ala Ser Asn His Leu Phe Glu Leu Tyr Tyr Gly Gly Trp Val Ala
 50                  55                  60
Pro Asn Ile Tyr Tyr Leu Gly Ala Ala Asn Val Ile Arg Cys Gly Pro
 65                  70                  75                  80
Leu Arg Ile Ala Gly Ile Ser Gly Ile Trp Lys Gly Tyr Asp Tyr Arg
                 85                  90                  95
Lys Ser His Phe Glu Arg Leu Pro Tyr Asn Arg Ala Asp Met Gln Ser
            100                 105                 110
Ile Tyr His Val Arg Glu Leu Asp Val Arg Lys Leu Leu Gln Ile Arg
            115                 120                 125
Thr Gln Val Asp Leu Gly Leu Ser His Asp Trp Pro Gln Gly Ile Glu
130                 135                 140
Trp His Gly Asp Phe Gln Lys Leu Phe Gln Lys Lys Pro Leu Phe Glu
145                 150                 155                 160
Pro Asp Ala Asn Ser Gly Arg Leu Gly Ser Val Ala Ala Arg Tyr Ile
                165                 170                 175
Met Asp Arg Leu Arg Pro Ala Phe Trp Phe Ser Ala His Leu His Cys
            180                 185                 190
Lys Tyr Ala Ala Ser Leu Thr His Gly Asp Tyr Lys Pro Ala Glu Leu
            195                 200                 205
Lys Asn Arg Phe Asn Pro Asn Pro Gln Pro His His Gln Pro Gln Gln
210                 215                 220
Pro Ser Leu Gly Asp Asp Val Leu Ser Ser Pro Ser Leu Val Thr Asn
225                 230                 235                 240
Glu Gln Pro Glu Val Pro Gly Ser Thr Asn Glu Gly Val Thr Ala Thr
                245                 250                 255
Arg Ser Val Glu Val Gly Ser Asp Ala Ala His Ile Ser Ser Lys Glu
            260                 265                 270
Val Ser Thr Thr Ile Val Asp Thr Ala Met Ser Glu Glu Ile Ile Met
            275                 280                 285
Ser Thr Leu Gly Gly Asp Asp Glu Ala Thr Thr Arg Ala Ala Glu Ser
290                 295                 300
Ala Lys Asn Ala Pro Gln Pro Gln Pro Ala Gln Gly Ala Glu Arg Asp
305                 310                 315                 320
Arg Ala Gln Leu Ser Ala Trp Gln Asn Phe His Ser Val Ala Thr Lys
                325                 330                 335
Asn Asp Ala Glu Glu Asn Val Arg Leu Met Lys Glu Ala Ala Glu Tyr
            340                 345                 350
Glu Lys Gln Ile Glu Ala Gly Leu Ile Ser Arg Pro Glu Val Asn Tyr
            355                 360                 365
Gln Leu Thr Trp Lys Lys Val Ala Val Lys Asp Asp Asn Leu Gly Arg
370                 375                 380
Glu Ile Ala Gly Val Ala Lys Ile Gly Tyr Asn Ala Gln Gln Glu Leu
385                 390                 395                 400
Arg Glu Ile Thr Glu Gln Glu Ile Arg Asp Gly Gly Thr Glu Val Lys
                405                 410                 415
Asn Pro Asp Glu Ile Asp Ile Cys Leu Asp Ser Ser Ser Asp Thr Ser
            420                 425                 430
Glu Lys Leu Glu Gln Lys Asp Thr Ile Ser Thr Lys Thr Arg Ser Thr
            435                 440                 445
Asp Lys Met Glu Ile Glu His Ser Ile Ser Ser Gly Lys Ala Glu Lys
450                 455                 460
Thr Ala Thr Ala Ala Val Asp Ala Ala Glu Ala Ser Gln Ser Gly Asp
```

-continued 465 470 475 480

Ile Pro Lys Glu Ile Arg Asp Gln Leu Pro Ala Ser Phe Arg Lys Pro
485 490 495

Glu Thr Ile Leu Asp Asp Ala Pro Val Phe Glu Ser Thr Leu Pro Glu
500 505 510

Ala Ile Ser Asn Thr Glu Thr Asn Phe Leu Ala Leu Asp Lys Cys Asp
515 520 525

Arg His Arg Gln Phe Ile Glu Leu Val Glu Tyr Pro Ala Ile Ser Ser
530 535 540

Pro Glu Glu Gly Glu Thr Gly Glu Glu Ser Arg Pro Tyr Gln Leu Lys
545 550 555 560

Tyr Asp Lys Glu Trp Leu Ala Ile Thr Arg Ala Phe Ala Asp Glu Leu
565 570 575

Thr Leu Gly Asp Pro Asn Ala Ser Val Pro Thr Asn Lys Gly Asp Ala
580 585 590

Arg Tyr Lys Pro Ser Ile Leu Ala Ala Glu Gln Trp Val Glu Glu Asn
595 600 605

Val Val Lys Pro Gly Arg Met Thr Ile Pro His Asn Phe Ser Ile Thr
610 615 620

Ala Pro Val Tyr Asp Pro Ala Val Pro Ile Thr Thr Thr Glu Met Pro
625 630 635 640

Pro Glu Tyr Thr Asn Pro Gln Thr Ala Gln Phe Cys Asp Leu Ile Gly
645 650 655

Ile Glu Asn Lys Phe His Ala Ser Asp Glu Glu Arg Phe Ala Arg Ala
660 665 670

Asp Ala Gly Pro His Pro Glu Pro Leu Gln Gln Arg His Gly Gln Arg
675 680 685

Phe Arg Gly His Gln Asp Arg Ser Phe Asn Ser Leu Gly Arg Gly Arg
690 695 700

Gly Arg Gly Phe Gly Arg Asp Gly Gly Arg Trp Gln Gly Gly Arg Gly
705 710 715 720

Gly Arg Gly Gly Gly Gly Arg Asn Arg Ala Gly Arg Gly Gly Arg Gly
725 730 735

Gly Arg Gly Glu Tyr Tyr Gly Ala Pro Ile
740 745

<210> SEQ ID NO 52
<211> LENGTH: 795
<212> TYPE: PRT
<213> ORGANISM: Blastomyces dermatitidis

<400> SEQUENCE: 52

Met Gln His Ile Pro Thr Pro Pro Ser Arg Ser Leu Arg Val Ala Leu
1 5 10 15

Glu Gly Cys Gly His Gly Lys Leu Asn Asp Ile Tyr Thr Ser Val Thr
20 25 30

Arg Ala Ala Glu Ile Lys Gly Trp Asp Gly Val Asp Leu Leu Ile Ile
35 40 45

Gly Gly Asp Phe Gln Ala Val Arg Asn Ser Tyr Asp Leu Ser Cys Met
50 55 60

Ser Val Pro Gln Lys Tyr Arg Gln Ile Gly Asp Phe His Glu Tyr Tyr
65 70 75 80

Ser Gly Ala Arg Val Ala Pro Tyr Leu Thr Ile Phe Val Gly Gly Asn
85 90 95

```
His Glu Ala Ser Asn His Leu Phe Glu Leu Tyr Tyr Gly Gly Trp Val
                100                 105                 110

Ala Pro Asn Ile Tyr Tyr Leu Gly Ala Ala Asn Val Ile Arg Cys Gly
            115                 120                 125

Pro Leu Arg Ile Ala Gly Ile Ser Gly Ile Trp Lys Gly Tyr Asp Tyr
        130                 135                 140

Arg Lys Pro His Phe Glu Arg Leu Pro Tyr Asn Arg Ser Asp Ile Gln
145                 150                 155                 160

Ser Ile Tyr His Val Arg Glu Leu Asp Val Arg Lys Leu Leu Gln Ile
                165                 170                 175

Arg Thr Gln Val Asp Leu Gly Leu Ser His Asp Trp Pro Gln Gly Ile
            180                 185                 190

Glu Trp His Gly Asp Phe Gln Lys Leu Phe Gln Lys Pro Leu Phe
        195                 200                 205

Glu Pro Asp Ala Asn Ser Gly Arg Leu Gly Ser Val Ala Ala Arg Tyr
210                 215                 220

Val Leu Asp Arg Leu Arg Pro Pro Tyr Trp Phe Ser Ala His Leu His
225                 230                 235                 240

Cys Lys Tyr Thr Ala Asn Leu Ile His Gly Asp Tyr Lys Pro Ala Gly
                245                 250                 255

Leu Lys Asp Arg Phe Ala Ser Asn Gln Gln Pro His Gln Pro Gln Leu
            260                 265                 270

Gly Gly Asp Ala Gly Ala Ser Pro Ser Ile Ile Ala Asp Glu Pro Ala
        275                 280                 285

Glu Val Ser Gly Ser Thr Asn Glu Gly Ile Arg Ser Thr Pro Val Val
        290                 295                 300

Glu Glu Val Ser Asn Ala Leu Arg Ile Ser Pro Asn Glu Pro Ser Thr
305                 310                 315                 320

Thr Ile Thr Gly Thr Ala Met Arg Glu Glu Thr Ile Leu Ser Thr Pro
                325                 330                 335

Gly Gly Glu Thr Glu Pro Thr Thr Leu Ser Thr Glu Gly Ile Glu Ser
            340                 345                 350

Ile Pro Gln Gln Gln Asn Pro Thr Gln Arg Ala Glu Arg Glu Arg Ala
        355                 360                 365

Gln Leu Ser Ala Trp Gln Asn Phe His Ser Val Ala Thr Lys Asn Asp
370                 375                 380

Ala Glu Glu Gly Ala Arg Leu Met Glu Glu Ala Ala Asp Tyr Glu Lys
385                 390                 395                 400

Gln Val Glu Ala Gly Phe Ile Ser Arg Pro Glu Val Asn Tyr Gln Leu
                405                 410                 415

Thr Trp Lys Lys Ile Gly Val Lys Asp Asp Gly Leu Gln Arg Glu Ile
            420                 425                 430

Glu Asp Val Ala Lys Ile Gly Tyr Asp Ser Gln Glu Pro Gly Lys Val
        435                 440                 445

Thr Glu Gln Glu Glu Arg Gly Gly Val Thr Thr Val Arg Asn Thr Asp
        450                 455                 460

Glu Ile Asp Ile Ser Leu Asp Ser Ser Ser Glu Thr Ser Glu Lys Leu
465                 470                 475                 480

Glu Gln Glu Asp Thr Thr Ser Ala Ile Pro Lys Asn Thr Asp Val Met
                485                 490                 495

Glu Ile Asp Ser Gly Thr Ser Phe Glu Lys Ala Glu Val Ala His Ile
            500                 505                 510

Gln Thr Pro Thr Ala Thr Ala Asn Ala Thr Gly Ala Leu Gln Leu Asp
```

```
                515                 520                 525
Asp Ile Pro Ala Asp Ile Leu Asp Gln Leu Pro Ala Ser Phe Arg Lys
530                 535                 540

Pro Gln Pro Val Pro Gly His Thr Pro Ile Phe Glu Pro Thr Leu Pro
545                 550                 555                 560

Glu Ala Ile Lys Asn Thr Val Thr Glu Phe Leu Ala Leu Asp Lys Cys
                565                 570                 575

Glu Thr Arg Arg Gln Phe Ile Glu Leu Val Glu Tyr Ser Ala Ile Ser
                580                 585                 590

Ser Pro Glu Glu Glu Ile Gly Glu Ser Arg Pro Tyr Gln Leu
                595                 600                 605

Lys Tyr Asp Lys Glu Trp Leu Ala Ile Thr Arg Ala Phe Ala Asp Glu
610                 615                 620

Leu Ile Leu Gly Asp Pro Asn Ala Ser Val Pro Pro Asn Lys Gly Asp
625                 630                 635                 640

Ala Gly Tyr Lys Pro Asp Ile Leu Ala Ala Gln Trp Val Glu Glu
                645                 650                 655

Asn Ile Val Lys Pro Gly Arg Met Thr Ile Pro His Asn Phe Ser Ile
                660                 665                 670

Thr Ala Pro Val Tyr Asp Pro Ala Ile Ser Ile Met Thr Thr Glu Met
                675                 680                 685

Pro Pro Glu Cys Thr Asn Pro Gln Thr Ala Arg Phe Cys Glu Leu Val
690                 695                 700

Gly Ile Glu Asn Lys Phe His Ala Ser Asp Glu Glu Arg Phe Ala Arg
705                 710                 715                 720

Ala Asp Ala Gly Pro Arg Pro Glu Pro Pro Gln Ser Arg Tyr Gly Gln
                725                 730                 735

Arg Ser Arg Gly His Gln Asp Gly Ser Val His Ser Phe Gly Arg Gly
                740                 745                 750

Glu Gly Glu Gly Glu Gly Gly Gly Arg Val Gly Val Gly Lys
                755                 760                 765

Val Val Val Glu Gly Gly Glu Val Ala Gly Glu Gly Val Glu Gly
                770                 775                 780

Glu Val Ala Asn Trp Asp Cys Val Leu Arg Phe
785                 790                 795

<210> SEQ ID NO 53
<211> LENGTH: 785
<212> TYPE: PRT
<213> ORGANISM: Aspergillus fumigatus

<400> SEQUENCE: 53

Met Glu Val Ser Ala Ala Asn Pro Ala Ser Leu Arg Val Ala Phe Glu
1               5                   10                  15

Gly Cys Gly His Gly Arg Leu Asp Asp Ile Tyr Asp Ser Val Thr Arg
                20                  25                  30

Ser Ala Thr Arg Arg Gly Trp Asp Gly Val Asp Leu Val Ile Gly
                35                  40                  45

Gly Asp Phe Gln Ala Val Arg Asn Ser Asn Asp Leu Ala Cys Met Ser
                50                  55                  60

Val Pro Gln Lys Tyr Lys Ala Ile Gly Asp Phe His Glu Tyr Tyr Ser
65                  70                  75                  80

Gly Lys Lys Thr Ala Pro Tyr Leu Thr Ile Phe Ile Gly Gly Asn His
                85                  90                  95
```

```
Glu Ala Ser Asn Tyr Leu Phe Glu Leu Tyr Gly Gly Trp Val Ala
                100             105             110

Pro Asn Ile Tyr Tyr Leu Gly Ala Ala Asn Val Ile Arg Cys Gly Pro
            115                 120             125

Leu Arg Ile Ala Gly Leu Ser Gly Ile Trp Lys Gly Tyr Asp Tyr Arg
        130                 135             140

Lys Pro His Phe Glu Arg Leu Pro Tyr Asn Asn Asp Val Gln Ser
145             150              155             160

Ile Tyr His Val Arg Glu Leu Asp Val Arg Lys Leu Leu Gln Ile Arg
                165             170             175

Thr Gln Val Asp Leu Gly Leu Ser His Asp Trp Pro Asn Arg Val Glu
        180                 185             190

Leu Cys Gly Asp His Glu Thr Leu Phe Ala Lys Lys His Gly Phe Arg
    195                 200             205

Glu Asp Ser Asn Asn Gly Arg Leu Gly Ser Ile Ala Ala Arg Phe Val
        210                 215             220

Leu Asp Arg Leu Arg Pro Ala Phe Trp Phe Ser Ala His Leu His Val
225             230             235                 240

Lys Phe Asn Ala Val Val Gln His Gly Asp Asn Leu Gln Pro Asp Ser
                245             250             255

Leu Gly Pro Thr Arg His Ile Ala Ser Ser Gln Arg Thr Ser Ser Asn
            260             265             270

Ala Ser Thr Leu Thr Thr Ser Phe Gly Met Asp Gly Ala Ala Val Thr
        275             280             285

Ser Leu Val Leu Gly Asp Glu Asp Met Pro Thr Glu Gln Ala Gln Val
    290             295             300

Pro His Asn Phe Ser Glu Asn Lys Gly His Ala Ala Asn Thr Leu Gly
305             310             315             320

Glu Asp Glu Arg Leu Glu Glu Pro Pro Arg Glu Leu Pro Thr Ala Gln
                325             330             335

Ala Thr Gln Gln Ser Asn Leu Val Gly Leu Ala Arg Thr Ser Ser Pro
        340                 345             350

Leu Lys Arg Val His Asp Asp Asn Gln Ser Arg Ile Ser Ala Trp Asn
    355             360             365

Asn Phe His Ala Val Ala Ala Arg Asp Glu Ala Ala Glu Asn Ala Pro
    370             375             380

Arg Leu Glu Glu Ser Gln Asp Asn Ser Ala Ser Gln Leu Pro His Ser
385             390             395             400

Leu Thr Trp Arg Lys Ile Ser Val Asp Glu Asp Pro Val Arg Lys
                405             410             415

Val Thr Thr Val Glu Lys Pro Ala Asp Glu Asn Glu Ser Glu Thr Lys
            420             425             430

Lys Gln Lys Thr Gly His Ala Val Ser Ala Thr Lys Asn Ser Asp Glu
        435             440             445

Ile Pro Leu Asp Leu Asp Ser Asp Ser Asp Gly Ile Ser Thr Thr
    450             455             460

Ala Glu Thr Gln Gly Ala Thr Gln Lys Gln Asn Ala Val Val Thr Gln
465             470             475             480

Pro Ala Ala Pro Asp Val Thr Gly Glu Ser Lys Leu Ser Gly Thr Thr
            485             490             495

Gln Gln Asp Lys Pro Gln Val Arg Ser Leu Asp Ser Gln Asp Val Arg
        500             505             510

Asn Leu Leu Pro Thr Ser Phe Ser Gln Pro Glu Ser Phe Val Ser Gln
```

```
            515                 520                 525
Asp Val Arg Asn Gln Leu Pro Ala Ser Phe Ser Arg Val Asp Cys Pro
    530                 535                 540

Val Ser Gln Asp Val Arg Asn Gln Leu Pro Ser Ser Phe Ser Arg Pro
545                 550                 555                 560

Gln Ala Thr Pro Lys Leu Asp Pro Ser Val Ser Glu Pro Val Pro Glu
                565                 570                 575

Thr Ile Thr Asn Lys Thr Thr Arg Phe Leu Ala Leu Asp Lys Cys Glu
                580                 585                 590

Pro Lys Arg His Phe Leu Glu Leu Leu Glu Ile Pro Ile Val Ser Glu
                595                 600                 605

Gln Asn Gly Ser Gln Arg Thr Arg Pro Phe Arg Leu Glu Tyr Asp Lys
    610                 615                 620

Glu Trp Leu Ala Ile Thr Arg Val Phe Ala Asp Glu Leu Gln Leu Gly
625                 630                 635                 640

Asp Leu Ala Val Gln Met Gln Pro Asp Arg Gly Gln Ala Phe Tyr Lys
                645                 650                 655

Pro Leu Ile Glu Glu Ala Glu Gln Trp Val Glu Glu Asn Val Val Lys
                660                 665                 670

Ala Gly Lys Met Met Val Pro Glu Asn Phe Thr Pro Thr Ala Pro Phe
            675                 680                 685

Phe Asp Pro Ala Val Pro Ile Thr Thr Asp Glu Leu Pro Pro Glu Phe
    690                 695                 700

Thr Asn Pro Gln Thr Ala Gln Phe Cys Glu Leu Ile Gly Ile Glu Asn
705                 710                 715                 720

Lys Phe His Leu Ser Asp Glu Glu Arg Gln Ala Arg Val Glu Ala Gly
                725                 730                 735

Pro Arg Pro Asn Lys Pro Lys Pro Glu Gly Gly Trp Asn Arg Gly Arg
            740                 745                 750

Arg Arg Asn Tyr Asn Asn Asn Arg Gly Gly Ser Gln Trp Trp
            755                 760                 765

Gly Arg Gly Ala Gly Arg Asp Arg Gly Arg Ser Gly Gly Asn Gln Arg
    770                 775                 780

Trp
785

<210> SEQ ID NO 54
<211> LENGTH: 606
<212> TYPE: PRT
<213> ORGANISM: Cryptococcus neoformans

<400> SEQUENCE: 54

Met Arg Ile Ala Ile Gln Gly Cys Ser His Gly Ser Leu Ala Gln Ile
1               5                   10                  15

Tyr Asp Val Val Asn Tyr Tyr Ser Ser Gln Thr Lys Asn Pro Ile Asp
                20                  25                  30

Leu Leu Leu Leu Cys Gly Asp Phe Gln Ala Leu Arg Ser Lys His Asp
            35                  40                  45

Tyr Ala Ser Leu Ala Val Pro Ala Lys Phe Lys Gln Leu Gly Ser Phe
    50                  55                  60

His Gln Tyr Tyr Ser Gly Glu Arg Val Ala Pro Val Leu Thr Ile Val
65                  70                  75                  80

Ile Gly Gly Asn His Glu Ala Ser Asn Tyr Met Trp Glu Leu Tyr His
                85                  90                  95
```

```
Gly Gly Trp Leu Ala Pro Ser Ile Tyr Tyr Leu Gly Ala Ala Gly Ser
            100                 105                 110

Val Tyr Val Asn Gly Leu Arg Ile Val Gly Ala Ser Gly Ile Tyr Lys
        115                 120                 125

Gly Phe Asp Tyr Arg Lys Gly His Phe Glu Lys Val Pro Tyr Asn Asp
    130                 135                 140

Lys Glu Leu Arg Ser Ile Tyr His Ile Arg Glu Tyr Asp Val Glu Lys
145                 150                 155                 160

Leu Met His Leu Thr Pro Ser Pro Ser Thr Ile Phe Leu Ser His Asp
                165                 170                 175

Trp Pro Thr Thr Ile Ala His His Gly Asn Lys Asn Ala Leu Leu Lys
            180                 185                 190

Arg Lys Pro Phe Phe Arg Asp Glu Ile Glu Lys Asn Thr Leu Gly Ser
        195                 200                 205

Pro Pro Leu Leu Arg Leu Met Asn His Phe Gln Pro Ser Tyr Trp Phe
    210                 215                 220

Ser Ala His Leu His Val Lys Phe Ala Ala Leu Tyr Glu His Gln Ala
225                 230                 235                 240

Pro Ser His Gly Pro Asp Val Asp Gly Gly Ala Pro Leu Pro Leu Pro
                245                 250                 255

Ala Met Ser Thr Ala Ile Ala Gln Thr Gly Asn Asn Pro Asp Glu Ile
            260                 265                 270

Gln Ile Asp Glu Glu Met Asp Glu Gly Asn Pro Asp Glu Ile Ile Val
        275                 280                 285

Glu Asp Glu Gly Glu Glu Ile Ile Val Arg Pro Arg Gln Val Asn Pro
    290                 295                 300

Asp Glu Ile Val Met Asp Asp Glu Glu Phe Asp Asp Pro Pro Pro Ala
305                 310                 315                 320

Val Pro Gln Pro Leu Pro Ile Thr Thr Ser Ser Val Val Asn Pro Glu
                325                 330                 335

Glu Ile Thr Ile Ser Asp Glu Glu Phe Asp Ala Pro Met Ala Val Ser
            340                 345                 350

Gln Ser Pro Gln Pro Leu Pro Pro Thr Arg Ala Asn Ala Ser Asn Pro
        355                 360                 365

Glu Glu Ile Ala Ile Ser Asp Asp Glu Phe Asp Pro Ala Pro Val
    370                 375                 380

Ala Gln Pro Leu Thr Ala Ile Asp Glu Ser Thr Asp Leu Ile Ala Gln
385                 390                 395                 400

Ser Arg Ser Asn Pro Ser His Pro His Val Ala Gly Thr Ile Ala Pro
                405                 410                 415

Pro Ala Ser Asp Ser Thr Ala Pro Arg Val Met Gln Glu Ala Arg Gln
            420                 425                 430

Glu Gln Gln Lys Trp Glu Leu His Gly Gly Lys Gly Met Glu Gly Val
        435                 440                 445

Thr Lys Phe Leu Ala Leu Asp Lys Cys Gly Pro Gly Lys Asp His Met
450                 455                 460

Gln Phe Leu Glu Ile Pro Asp Pro Ser Pro Ala Ile Pro Gly Pro
465                 470                 475                 480

Pro Arg Leu Thr Tyr Asp Pro Glu Trp Leu Ala Ile Ser Arg Ala Phe
                485                 490                 495

His Pro Tyr Leu Ser Thr Ser Tyr Gln Pro Ile Pro Leu Pro Ser Pro
            500                 505                 510

Asp Val Leu Glu Gln Met Val Lys Asp Glu Val Thr Arg Ile Lys Glu
```

```
            515                 520                 525
Glu Gly Leu Leu Val Pro Ala Val Pro Glu Lys Gly Ala Val Glu Gly
        530                 535                 540

Gln Glu Gly Leu Val Trp Glu Lys Gly Lys Val Asp Val Gly Arg Val
545                 550                 555                 560

Gln Arg Phe Trp Trp Thr Ala Pro Pro Glu Gly His Pro Gly Gly Asn
            565                 570                 575

Asp Ala Ala Trp Tyr Thr Asn Pro Gln Thr Glu Ala Phe Cys Gly Met
        580                 585                 590

Leu Gly Val Gln Asn Lys Ile Asn Pro Pro Val Asn Arg Ser
            595                 600                 605

<210> SEQ ID NO 55
<211> LENGTH: 340
<212> TYPE: PRT
<213> ORGANISM: Rhizopus delemar

<400> SEQUENCE: 55

Met Met His Gln Lys Ile Ala Ile Glu Gly Cys Cys His Gly Glu Leu
1               5                   10                  15

Asp Lys Ile Tyr Asn Ala Val Arg Glu Glu Ala Arg Tyr Gly Gln
            20                  25                  30

Lys Val Asp Leu Val Leu Ile Cys Gly Asp Phe Gln Ala Leu Arg Asn
        35                  40                  45

Glu Ser Asp Leu Ala Cys Met Ala Val Pro Asp Lys Phe Lys Thr Met
50                  55                  60

Gly Thr Phe Trp Lys Tyr Tyr Ser Gly Gln Ala Arg Ala Pro Tyr Pro
65                  70                  75                  80

Thr Ile Phe Ile Gly Gly Asn His Glu Ala Ser Asn Tyr Leu Trp Glu
            85                  90                  95

Leu Tyr His Gly Gly Trp Val Cys Asp Asn Ile Tyr Tyr Leu Gly Cys
        100                 105                 110

Ala Gly Val Ile Asn Phe Gly Gly Leu Arg Ile Gly Gly Leu Ser Gly
        115                 120                 125

Ile Tyr Lys Gln Asn Asp Tyr His Ile Gly His Glu Thr Val Pro
        130                 135                 140

Tyr Asn Ser Ser Glu Met Arg Ser Ile Tyr His Val Arg Glu Tyr Asp
145                 150                 155                 160

Val Arg Lys Leu Leu Gln Val Gln Glu Pro Ile Asp Ile Phe Leu Ser
            165                 170                 175

His Asp Trp Pro Arg Gly Ile Glu Arg Tyr Gly Asp Val Leu Ser Asn
        180                 185                 190

Ser Leu Gly Ser Ser Pro Asn Glu Val Leu Leu Tyr Asn Leu Lys Pro
        195                 200                 205

Ala Arg Trp Phe Ala Ala His Leu His Val Arg Tyr Glu Ala Glu Ile
        210                 215                 220

Asn His Glu Lys Lys Asp Glu Tyr Ser Val Ser Ala Arg Glu Leu Leu
225                 230                 235                 240

Gly Arg Lys Gly Ala Asn Lys Ile Arg Asn Ser Asp Glu Ile Gln Ile
            245                 250                 255

Asp Asp Asp Ser Glu Asp Ile Asn Ala Val Ser Ser Ser Pro Thr
        260                 265                 270

Asn Asp Val Asp Asn Ser Lys Val Val Ser Lys Thr Thr Lys Phe Leu
        275                 280                 285
```

```
Ser Leu Asp Lys Cys Leu Pro Arg Arg Gln Phe Leu Glu Glu Gln Arg
    290                 295                 300

Lys Cys Gly Ile Leu Asp Leu Lys Ile Pro His Asn Phe Glu Pro Thr
305                 310                 315                 320

Ala Pro Val Tyr Ile Pro Lys Lys Gln Lys Gly Arg His Ile Phe Lys
                325                 330                 335

Gln Pro Arg Met
            340

<210> SEQ ID NO 56
<211> LENGTH: 706
<212> TYPE: PRT
<213> ORGANISM: Coccidioides immitis

<400> SEQUENCE: 56

Met Ala Ser Asp Leu Pro Thr Gln Lys Gly Phe Arg Leu Ala Ile Glu
1               5                   10                  15

Gly Cys Gly His Gly Lys Leu His Glu Ile Tyr Asp Ser Val Lys Lys
                20                  25                  30

Ser Ala Glu Ala Lys Gly Trp Asp Gly Val Asp Leu Val Ile Ile Gly
            35                  40                  45

Gly Asp Phe Gln Ala Val Arg Asn Ser Asn Asp Met Ala Cys Met Ala
        50                  55                  60

Val Pro Ala Lys Tyr Lys Lys Ile Gly Asp Phe His Glu Tyr Tyr Ser
65                  70                  75                  80

Gly Ala Arg Val Ala Pro Tyr Leu Thr Ile Phe Val Gly Gly Asn His
                85                  90                  95

Glu Ala Ser Asn His Leu Phe Glu Leu Tyr Tyr Gly Gly Trp Val Ala
                100                 105                 110

Pro Asn Ile Tyr Tyr Leu Gly Ala Ala Asn Val Ile Arg Cys Gly Pro
            115                 120                 125

Leu Arg Ile Ala Gly Met Ser Gly Ile Trp Lys Gly Tyr Asp Tyr Arg
130                 135                 140

Arg Gln His Phe Glu Arg Leu Pro Tyr Gly Asp Asp Ala Leu Arg Ser
145                 150                 155                 160

Ile Tyr His Val Arg Glu Ile Asp Val Arg Lys Leu Leu Gln Val Arg
                165                 170                 175

Thr Gln Val Asp Ile Gly Ile Ser His Asp Trp Pro Gln Ala Ile Glu
            180                 185                 190

Trp Thr Gly Asp Val Asp Asp Leu Phe Arg Arg Lys Pro His Phe Val
        195                 200                 205

Lys Asp Ala Glu Ser Gly Lys Leu Gly Ser Pro Ala Val Arg Tyr Val
210                 215                 220

Leu Asp Arg Leu Arg Pro Ala His Trp Phe Ser Ala His Leu His Val
225                 230                 235                 240

Lys Tyr Thr Ser Thr Leu Glu His Lys Ala Tyr Ser Pro Pro Arg Ala
                245                 250                 255

Val Asn Ala His Asn Ile Asp Thr Lys Ser Gln Gln Ser Arg Met Lys
            260                 265                 270

Asp Pro Ala Lys Asp Pro Glu Pro Glu Glu Val Met Ala Lys Pro Met
        275                 280                 285

Gln Ala Cys Val Arg Arg Pro Gln Met Met Thr Pro Gly Ala Ala Ala
    290                 295                 300

Tyr Ser Asp Arg Arg Pro Val Thr Tyr Asn Thr Gln Leu Gln Ser Ser
305                 310                 315                 320
```

Glu Gln Asp Arg Ile Asn Ala Trp Arg Gly Phe Tyr Glu Val Ala Ser
                325                 330                 335

Lys Arg Glu Ala Glu Asn Ala Glu Tyr Leu Lys Ala Ala Asp Glu
        340                 345                 350

Phe Arg Arg Arg Val Asp Ala Gly Glu Ile Glu Lys Pro Lys Ser Asn
        355                 360                 365

Ile Asp Tyr Gln Val Thr Trp Lys Lys Val Val Thr Asp Asp Gly Leu
        370                 375                 380

Ser Arg Glu Val Ser Asp Val Val Arg Thr Lys Ala Glu Asp Glu Ile
385                 390                 395                 400

Asn Gln Val Gln Lys Glu Thr Ala Pro Ser Pro Val Lys Asn Ala Asp
                405                 410                 415

Glu Ile Asp Leu Glu Met Glu Ser Ala Ser Glu Thr Ala Glu Thr Pro
                420                 425                 430

Asn Glu Ala Leu Asp Ala Ser Ile Thr Lys Gln Ser Phe Ser Thr Gln
                435                 440                 445

Leu Glu Thr Thr Ala Thr Met Pro Met Pro Pro Ala Gln Phe Asp Gly
                450                 455                 460

Val Ser Asp Glu Leu Arg Glu Gln Leu Pro Ala Ser Phe Gln Lys Arg
465                 470                 475                 480

Asp Lys Thr Gln Asp Lys Ala Ile Ala Glu Glu Leu Pro Gly Gly
                485                 490                 495

Ile Thr Asn Lys Ala Thr Gln Phe Leu Ala Leu Asp Lys Cys Glu Pro
                500                 505                 510

His Arg Lys Phe Leu Glu Leu Leu Glu Ile Phe Pro Val Ser Glu Ser
                515                 520                 525

Asp His Thr Asp Glu Gln Arg Pro Tyr Gln Leu Lys Tyr Asp Lys Glu
                530                 535                 540

Trp Leu Ala Ile Thr Arg Val Phe Ala Glu Gly Phe Val Val Gly Lys
545                 550                 555                 560

Lys Ser Gln Val Leu Ile Asp Lys Gly Ser Ala Phe Tyr Lys Pro Lys
                565                 570                 575

Ile Ile Asp Ala Glu Ala Trp Val Glu Glu Asn Ile Val Lys Glu Gly
                580                 585                 590

Lys Met Val Val Pro His Asn Phe Thr Ile Thr Ala Pro Val Tyr Glu
                595                 600                 605

Pro Ser Val Pro Val Thr Thr Pro Glu Gln Pro Phe Glu Tyr Leu Asn
                610                 615                 620

Pro Gln Thr Thr Arg Phe Cys Glu Met Leu Gly Ile Ala Asn Pro Phe
625                 630                 635                 640

Glu Gln Ser Glu Glu Glu Arg Ala Glu Gln Glu Ala Ala Ile Arg Gln
                645                 650                 655

Ala Asn Asp Arg Arg Lys Ser Glu Pro Ala His Ser Gly Arg Arg Gly
                660                 665                 670

Gly Phe Arg Gly Gly Arg Gly Gly Trp Gly Arg Gly Asn Gly Gly
                675                 680                 685

Tyr Gly Gly Arg Gly Gly Trp Gln Gly Gly Arg Gly Arg Gly Arg Gly
        690                 695                 700

Gly Pro
705

<210> SEQ ID NO 57
<211> LENGTH: 569

<212> TYPE: PRT
<213> ORGANISM: Ustilago maydis

<400> SEQUENCE: 57

```
Met Lys Leu Ala Ile Gln Gly Cys Ser His Gly Glu Leu Asp Ala Ile
1               5                   10                  15

Tyr Ala Ser Leu Leu Arg Thr Glu Arg Gln Ser Leu His Ile Asp
            20                  25                  30

Ala Leu Leu Leu Cys Gly Asp Phe Gln Ala Ile Arg Asn His Ser Asp
        35                  40                  45

Leu His Ala Leu Ala Val Pro Gln Lys Tyr Arg Gln Leu Gly Asp Phe
    50                  55                  60

His Ser Tyr Tyr Ser Gly Glu Lys Ile Ala Pro Ile Leu Thr Leu Val
65                  70                  75                  80

Ile Gly Gly Asn His Glu Ala Ser Asn Tyr Met His Glu Leu Tyr His
                85                  90                  95

Gly Gly Trp Leu Ala Pro Asn Ile Tyr Phe Leu Gly Ala Ala Gly Val
            100                 105                 110

Ile Glu Leu Asn Gly Ile Val Val Ala Gly Ile Ser Gly Ile Tyr Lys
        115                 120                 125

Glu Lys Asp Tyr Arg Lys Gly Arg Phe Glu Lys Leu Pro Tyr Asp Ala
130                 135                 140

Gly Ser Ile Arg Ser Cys Tyr His Thr Arg Glu Phe Asp Val Val Arg
145                 150                 155                 160

Leu Lys Ala Leu Lys Asp Gly Gln Val Glu Ile Val Met Ser His Asp
                165                 170                 175

Trp Pro Asn Thr Ile Glu Gln Trp Gly Asn Thr Gln Ala Leu Ile Arg
            180                 185                 190

Lys Lys Pro Phe Phe Lys Glu Ile Glu Ser Arg Thr Leu Gly Ser
        195                 200                 205

Pro Pro Leu Met Glu Leu Leu Gln Cys Leu Lys Pro Ala Phe Trp Phe
210                 215                 220

Ser Ala His Leu His Val Lys Phe Ala Ala Leu Phe Arg His Gly Gln
225                 230                 235                 240

Met Asp Pro Ala Ile Glu Pro Ser Ser Thr Thr Ala Ala Asn Thr Asn
                245                 250                 255

Pro Glu Ala Leu Asp Ile Ser Leu Asp Ser Asp Asp Leu Pro Glu
            260                 265                 270

Ser Pro Lys Pro Ala Pro Ser Ala Asp Ile Ala Val Asp Gly Thr Val
        275                 280                 285

Thr Lys Ser Ala Thr Ala Thr Arg Phe Leu Ala Leu His Lys Cys Leu
290                 295                 300

Pro Gln Thr Gln Phe Leu Gln Ile Ile Asn Leu Pro Ser Pro Gln Asp
305                 310                 315                 320

Ala Glu Leu Glu Ser Arg Lys Ala Ser Leu Gly Tyr Thr Gln Arg Ile
                325                 330                 335

Pro Pro Ser Leu Arg Tyr Asn Gln Arg Trp Leu Ala Ile Thr Arg Ala
            340                 345                 350

Phe His Ser His Phe Ser Leu Gln Tyr Arg Gln Pro Asp Leu Pro Asp
        355                 360                 365

Pro Phe Ser Ala Ser Leu Leu Ala Arg Ile Glu Glu Glu Arg Trp
370                 375                 380

Ile Glu Gln Asn Leu Val Ser Pro Phe Thr Thr Arg Asn Ser Gly Lys
385                 390                 395                 400
```

```
Arg Lys Gln Asp Glu Arg Gly Ser Arg Ala Cys Thr Pro Gln Asp
            405                 410                 415

Glu Arg Glu Thr Glu Gly Val Gly Leu Asp Val His Arg Val Gln Gln
                420                 425                 430

Phe Val Arg Thr Ala Pro Ala Pro Phe Glu Pro Gly Gly Leu Ser Gln
            435                 440                 445

Ala Pro Pro Ala Trp Tyr Thr Asn Pro Gln Thr Glu Ala Phe Cys Arg
450                 455                 460

Phe Leu Gly Ile Glu Asn Lys Ile Asn Pro Arg Pro Asp Ala Phe Gly
465                 470                 475                 480

Gly Ala Ser Cys Tyr Pro His Pro Gln Glu His Leu Ala Ala Ser Phe
            485                 490                 495

His Pro Ala Thr Pro Thr Gly Asp Arg Asp Pro Ser Gln Val His Ser
            500                 505                 510

Glu Ala Val Ser Asp Pro Asn Ala Leu Ala Ile Asp Met Asp Asp Leu
            515                 520                 525

Asp Ser Asp Cys Ser Asp Ala His Ala Asn Gly Asp Gly Phe Lys His
530                 535                 540

Asp Gly Ser Arg Arg Asp Val Leu Thr Leu Ser Asp Asp Asp Glu Leu
545                 550                 555                 560

His Ala Arg Trp Lys Glu Gly Thr Gly
            565

<210> SEQ ID NO 58
<211> LENGTH: 649
<212> TYPE: PRT
<213> ORGANISM: Magnaporthe oryzae

<400> SEQUENCE: 58

Met Gly Asp Ala Gln Thr Gln Thr Phe Thr Ser Pro Asp Gly Leu Arg
1               5                   10                  15

Val Ala Val His Gly Cys Gly His Gly Val Leu Asn Ala Ile Tyr Ala
                20                  25                  30

Ala Val Ala Ile Ser Cys Lys Glu Arg Gly Trp Asp Thr Val Asp Leu
            35                  40                  45

Leu Ile Ile Gly Gly Asp Phe Gln Ala Val Arg Asn Ala Ala Asp Leu
        50                  55                  60

Ser Val Met Ser Cys Pro Val Lys Tyr Arg Thr Ile Gly Asp Phe His
65                  70                  75                  80

Glu Tyr Tyr Ser Gly Ser Arg Thr Ala Pro Tyr Leu Thr Ile Phe Ala
                85                  90                  95

Gly Gly Asn His Glu Ala Ala Ser His Ser Trp Glu Leu Phe Tyr Gly
            100                 105                 110

Gly Trp Val Ala Pro Asn Ile Tyr Tyr Leu Gly Pro Ala Asn Val Val
        115                 120                 125

Arg Leu Gly Pro Leu Arg Ile Ala Ala Leu Gly Gly Ile Trp Ala Gly
    130                 135                 140

Tyr Asp Tyr Arg Lys Pro His His Glu Arg Leu Pro Phe Ser Glu Ser
145                 150                 155                 160

Asn Ile Lys Ser Phe Tyr His Val Arg Glu Met Asp Val Arg Lys Leu
                165                 170                 175

Leu Gln Ile Arg Thr Gln Val Asp Ile Gly Leu Ser His Asp Trp Pro
            180                 185                 190

Arg Ala Val Glu Arg His Gly Asp Glu Gly Ala Leu Phe Arg Lys Lys
```

```
                195                 200                 205
Pro Phe Leu Arg Asp Glu Ser Lys Ala Gly Thr Leu Gly Asn Pro Ala
210                 215                 220
Ala Thr Tyr Val Met Asp Arg Leu Arg Pro Ala Tyr Trp Phe Ala Ser
225                 230                 235                 240
His Met His Cys Lys Phe Ala Ala Leu Lys Val Tyr Thr Asp Glu Pro
                245                 250                 255
Pro Thr Glu Asp Asp Gly Val Glu Ala His Lys Ile Asp His Gly Pro
                260                 265                 270
Val Ala Gln Ala Lys Asp Leu Thr Ala Glu Ala Ser Ala Pro Thr Ile
            275                 280                 285
Glu Asn Pro Asp Glu Ile Asp Leu Asp Met Asp Asp Asn Asp Asp Ala
290                 295                 300
Ala Gly Ala Gly Ala Ala Ala Ala Ser Thr Ser Thr Asn Gly Glu
305                 310                 315                 320
Thr Ala Ala Ala Lys Asp Val Val Ser Glu Asn Thr Ser Asn Gly Lys
                325                 330                 335
Val Val Asn Pro Asp Ala Ile Asp Leu Asp Leu Asp Asp Glu Ala
                340                 345                 350
Gln Asp Thr Ala Pro Gly Ala Pro Gly Gly Gln Pro Glu Glu Asp Gly
            355                 360                 365
Glu Gly Lys Ala Lys Pro Leu Ser Thr Glu Lys Ala Thr Asn Glu Asn
370                 375                 380
Asn Thr Thr Thr Thr Ala Ala Ser Ser Phe Ile Ser Gln Asp Ile Arg
385                 390                 395                 400
Asn Gln Leu Pro Ala Ser Phe Ala Pro Pro Gln Gln Ala Pro Thr
                405                 410                 415
Glu Ser Arg Ala Lys Arg Thr Pro Gly Gln Pro Val Pro Glu Gly Ile
            420                 425                 430
Thr Asn Lys Glu Val Arg Phe Leu Ala Leu Ser Lys Cys Leu Pro Gly
            435                 440                 445
His Asp Phe Leu Gln Leu Cys Asp Ile Ser Pro Leu Asp Arg Ser Ser
            450                 455                 460
Thr Gly Ser Ser Asn Asp Thr Pro Pro Lys Tyr Arg Leu Glu Tyr Asp
465                 470                 475                 480
Pro Glu Trp Leu Ala Ile Thr Arg Val Phe Ala Ser Glu Leu Ile Ile
                485                 490                 495
Gly Asp Ser Asn Ala Thr Ala Thr Thr Asp Leu Gly Glu Glu His Tyr
                500                 505                 510
Lys Pro Leu Ile Gln Ala Glu Arg Thr Trp Val Glu Asn Ile Val
            515                 520                 525
Ala Lys Asp Lys Leu Ala Ile Pro Glu Asn Phe Val Ile Thr Ala Pro
            530                 535                 540
Pro His Ile Pro Gly Gln Pro Glu Gly Val Pro Glu Gln Pro Asp Glu
545                 550                 555                 560
Tyr Thr Asn Pro Gln Thr Ser Ala Phe Cys Glu Leu Leu Gly Val Lys
                565                 570                 575
Asn Leu Trp Asn Ala Thr Asp Glu Glu Arg Leu Glu Arg Lys Asn Gln
                580                 585                 590
Gly Pro Pro Pro Asp Gln Gly Gly Phe Arg Gly Gly Arg Gly Gly
            595                 600                 605
Ser Gly Gly Gly Arg Gly Gly Arg Gly Gly Phe Gly Gly Arg Gly Arg
            610                 615                 620
```

```
Gly Gly Arg Gly Gly Gln Gly Gly Gly Gly Arg Gly Arg Gly Phe Arg
625                 630                 635                 640

Gly Gly His Gly Gly Arg Gly Arg Tyr
                645

<210> SEQ ID NO 59
<211> LENGTH: 546
<212> TYPE: PRT
<213> ORGANISM: Fusarium graminearum

<400> SEQUENCE: 59

Met Thr Thr Asn Ala Phe Glu Ala Gln Gly Val Arg Val Ala Ile Glu
1               5                   10                  15

Gly Cys Thr Gln Gly His Gly Thr Leu Asp Ala Ile Tyr Ala Ser Val
            20                  25                  30

Glu Glu Ser Cys Lys Gln Arg Gly Trp Asp Gly Val Asp Ile Leu Ile
        35                  40                  45

Ile Gly Gly Asp Phe Gln Ser Val Arg Asn Ala Glu Asp Leu Ser Ile
    50                  55                  60

Met Ser Cys Pro Val Lys Tyr Arg His Leu Gly Asp Phe Pro Lys Tyr
65                  70                  75                  80

Tyr Ser Gly Glu Arg Lys Ala Pro Tyr Leu Thr Ile Phe Ile Ala Gly
                85                  90                  95

Asn His Glu Ala Ser Ser His Leu Trp Glu Leu Tyr Tyr Gly Gly Trp
            100                 105                 110

Val Ala Pro Asn Ile Tyr Tyr Met Gly Ala Ala Asn Ile Leu Arg Phe
        115                 120                 125

Gly Pro Leu Arg Ile Ala Gly Leu Ser Gly Ile Trp Lys Gly Phe Asp
    130                 135                 140

Tyr Arg Lys Pro His His Glu Arg Leu Pro Phe Ser Gly Gly Asp Val
145                 150                 155                 160

Lys Ser Trp Tyr His Val Arg Glu Ile Asp Val Arg Lys Leu Leu Gln
                165                 170                 175

Val Gln Thr Gln Val Asp Val Gly Leu Ser His Asp Trp Pro Arg Ala
            180                 185                 190

Val Glu Leu His Gly Asp His Glu Trp Leu Phe Arg Lys Lys Pro Asp
        195                 200                 205

Phe Arg Asn Glu Ser Arg Asp Gly Thr Leu Gly Ser Val Ala Ala Glu
    210                 215                 220

Tyr Val Met Asp Arg Leu Arg Pro Pro His Trp Phe Ser Ala His Met
225                 230                 235                 240

His Val Lys Phe Ala Ala Ile Lys Thr Tyr Ser Glu Ala Gln Pro Glu
                245                 250                 255

Val Glu Glu Thr Lys Gln Glu Leu Ala Pro Ala Ala Ala Pro Val Pro
            260                 265                 270

Ala Thr Glu Asn Asn Pro Asp Glu Ile Asp Leu Asp Met Asp Asp Glu
        275                 280                 285

Asp Glu Asp Thr Lys Pro Asn Pro Glu Pro Glu Ala Lys Lys Ser Glu
    290                 295                 300

Pro Glu Val Glu Glu Ala Lys Glu Ala Ser Asn Glu Val Ser Asp Glu
305                 310                 315                 320

Leu Arg Ala Gln Leu Pro Ala Ser Phe Ala Arg Pro Gln Pro Lys Lys
                325                 330                 335

Thr Pro Gly Gln Pro Val Pro Pro Gly Ile Thr Asn Lys Glu Val Arg
```

```
                340                 345                 350
Phe Leu Ala Leu Asp Lys Cys Leu Pro Gly Arg His Phe Leu Gln Leu
            355                 360                 365

Cys Asp Leu Gln Pro Phe Asn Pro Glu Thr Ser Ser Glu Tyr Pro Pro
        370                 375                 380

Ala Gln Glu Ser Pro Arg Trp Arg Leu Gln Tyr Asp Pro Glu Trp Leu
385                 390                 395                 400

Ala Ile Thr Arg Val Phe His Asp Ser Leu Val Ile Gly Asp Ser Asn
                405                 410                 415

Ala Gln Ser Pro Pro Asp Leu Gly Glu Glu His Tyr Gln Pro Leu Ile
            420                 425                 430

Lys Lys Glu Arg Glu Trp Val Glu Asp Asn Ile Val Lys Ala Gly Lys
        435                 440                 445

Leu Asp Val Pro Tyr Asn Phe Glu Ile Thr Ala Pro Pro His Val Pro
450                 455                 460

Gly Gly Pro Glu Ile Ala Ser Glu Gln Pro Ser Glu Tyr Thr Asn Pro
465                 470                 475                 480

Gln Thr Ser Lys Phe Cys Glu Ile Met Glu Leu Ser Asn Ile Trp Asp
                485                 490                 495

Ala Thr Asp Glu Glu Arg Arg Gln Arg Lys Ala Gln Gly Pro Pro Lys
            500                 505                 510

Thr Asp Gln Arg Phe Thr Gly Gly Gly Arg Gly Gly Arg Gly Arg Gly
        515                 520                 525

Gly Gly Arg Gly Gly Arg Gly Arg Gly Arg Gly Arg Gly Arg Gly Gly
    530                 535                 540

Arg Trp
545

<210> SEQ ID NO 60
<211> LENGTH: 566
<212> TYPE: PRT
<213> ORGANISM: Plasmodium vivax

<400> SEQUENCE: 60

Met Ile Ile Ala Val Val Gly Cys Thr His Gly Glu Leu Asn Phe Ile
1               5                   10                  15

Tyr Ala Thr Ile Glu Lys Leu Glu Gln Asp Asn Asn Phe Lys Val Asp
            20                  25                  30

Leu Leu Ile Cys Cys Gly Asp Phe Glu Cys Val Arg Tyr Gly Val Asp
        35                  40                  45

Asn Asp Cys Leu Asn Val Pro Asn Lys Tyr Lys Lys Glu Glu Asn Asp
    50                  55                  60

Phe Arg Asp Tyr Phe Thr Gly Lys Lys Ala Lys Val Leu Thr Ile
65                  70                  75                  80

Phe Ile Gly Gly Asn His Glu Ala Val Asn Val Leu Lys Gln Leu Tyr
                85                  90                  95

Tyr Gly Gly Trp Val Ala Pro Asn Ile Tyr Phe Leu Gly Tyr Ser Asn
            100                 105                 110

Val His Asn Ile Asn Asp Phe Arg Ile Cys Ser Leu Ser Gly Ile Tyr
        115                 120                 125

Lys Lys Tyr Asn Phe Tyr Lys Lys Tyr Asn Glu His Tyr Pro Tyr Asp
    130                 135                 140

Glu Ile Ser Lys Val Ser Ala Tyr His Ile Arg Lys Phe Glu Ile Glu
145                 150                 155                 160
```

```
Lys Leu Lys Leu Leu Lys Glu Lys Ile Asp Ile Val Val Thr His Asp
                165                 170                 175
Trp Pro Asn Asn Ile Glu Lys His Gly Asp Val Asn Asp Leu Val Arg
            180                 185                 190
Arg Lys Phe His Phe Gln Ser Asp Ile Tyr Asn Asn Thr Leu Gly Asn
        195                 200                 205
Pro His Thr Glu Phe Leu Leu Asn Lys Leu Lys Pro Tyr Phe Trp Phe
    210                 215                 220
Ser Ser His Leu His Val Lys Tyr Ser Ala Ile Phe Leu His Ser Asp
225                 230                 235                 240
Lys Arg Asn Tyr Thr Arg Phe Leu Ser Leu Asp Lys Ala Glu Pro Arg
                245                 250                 255
Lys His Phe Ile Gln Ile Leu Asn Ile Glu Lys Arg Asn Asn Ile Pro
            260                 265                 270
Tyr Leu Ser Phe Asp His Leu Pro Arg Pro Ser Ala Asn Asp Pro Asp
        275                 280                 285
Gly Lys Ser His Phe Phe Asn Glu Asp Tyr Glu Glu Leu Leu Gln His
    290                 295                 300
Val Glu Asp Val Gln Arg Arg Asp Ala Glu Gly Gly Lys Gly His
305                 310                 315                 320
Ser Gly Gly Ala Ala Gln Ala Lys Glu Asn Ala Pro Val Glu Ala Ala
                325                 330                 335
Thr Arg Glu Ala Ala Thr Arg Glu Ala Val Lys Gln Glu Asn Ala Ala
            340                 345                 350
Val Glu Thr Ser Pro Gly Glu Ala Ala Thr Lys Glu Asp Ala Pro Gly
        355                 360                 365
Glu Ala Asp Pro Gln Glu Pro Pro Gln Glu Asn Ala Ala Pro Glu
    370                 375                 380
Arg Lys Lys Leu Phe Ile Cys Tyr Asp Glu Glu Trp Leu Ala Ile Leu
385                 390                 395                 400
Lys Ala Asn Gln His Leu Val Ser Glu Gly Cys Asp Lys Asp Tyr Asn
                405                 410                 415
Leu Glu Lys Leu Lys Cys Pro Ser Lys Glu Asp Phe Glu Tyr Ile Arg
            420                 425                 430
Asp Lys Leu Lys Glu Leu Glu Lys Thr Ser Val Lys Gly Lys Asp Tyr
        435                 440                 445
Tyr Leu Val His Gly Tyr Asn Thr Pro Ser Tyr Lys His Leu Trp Glu
    450                 455                 460
Gln Arg Gln Leu Phe Leu Ser Arg Phe Asp Phe Glu Glu Leu Arg Met
465                 470                 475                 480
Tyr Asp Asp Phe Glu Arg Leu Phe Phe Ala Glu Glu Val Arg Lys Met
                485                 490                 495
Asp Ala Gly Leu Pro Leu Asp Pro Pro Lys Val Glu Glu Asp Glu Glu
            500                 505                 510
Glu Asp Gly Glu Glu Asp Glu Pro Glu Glu Val Gly Asn Asn Gln
        515                 520                 525
Ala Asp Glu His Gly Gly Gly Asn Pro Asn Gly Asp Asn Ala Pro His
    530                 535                 540
Ser Gly Asn Ala Pro Asn Val Glu Gly Ala Ser Glu Thr Asn Glu Ile
545                 550                 555                 560

Ser Leu Ser Ile Asp Cys
                565
```

```
<210> SEQ ID NO 61
<211> LENGTH: 565
<212> TYPE: PRT
<213> ORGANISM: Plasmodium falciparum

<400> SEQUENCE: 61

Met Phe Ile Ala Val Val Gly Cys Thr His Gly Glu Leu Asp Leu Ile
1               5                   10                  15

Tyr Ser Thr Leu Glu Lys Ile Glu Glu Asn Lys Ile Lys Val Asp
            20                  25                  30

Leu Leu Ile Cys Cys Gly Asp Phe Gln Ser Val Arg Tyr Asn Val Asp
                35                  40                  45

Asn Glu Cys Leu Asn Val Pro Ala Lys Tyr Lys Lys Glu Gln Asn Asp
    50                  55                  60

Phe Val Asp Tyr Phe Thr Gly Lys Lys Ala Lys Ile Leu Thr Ile
65                  70                  75                  80

Phe Val Gly Gly Asn His Glu Ala Met Asn Val Leu Lys Gln Leu Tyr
                85                  90                  95

Tyr Gly Gly Trp Val Ala Pro Asn Ile Tyr Tyr Leu Gly Tyr Ser Ser
                100                 105                 110

Val His Asn Ile Asn Asn Phe Arg Ile Cys Ser Leu Ser Gly Ile Tyr
            115                 120                 125

Lys Lys Tyr Ser Phe Phe Lys Lys Tyr Glu Ser Tyr Pro Tyr Thr
    130                 135                 140

Asp Ile Thr Lys Val Ser Ala Tyr His Ile Arg Lys Tyr Glu Ile Glu
145                 150                 155                 160

Lys Leu Lys Leu Leu Lys Asn Asn Val Asp Ile Val Val Thr His Asp
                165                 170                 175

Trp Pro Asn Asn Ile Glu Lys His Gly Asp Val His Asp Leu Leu Arg
                180                 185                 190

Arg Lys Tyr His Phe Gln Ser Asp Val Tyr Asn Asn Thr Leu Gly Asn
            195                 200                 205

Pro His Thr Glu Ile Leu Leu Asn Lys Leu Lys Pro Tyr Phe Trp Phe
    210                 215                 220

Ala Ser His Leu His Val Lys Tyr Ser Ala Leu Tyr Ile His Asn Asp
225                 230                 235                 240

Gln Lys Gln Tyr Thr Arg Phe Leu Ser Leu Asp Lys Ala Gln Glu Tyr
                245                 250                 255

Lys His Phe Ile Gln Ile Leu Asn Ile Val Lys Lys Asp Ser Ser
            260                 265                 270

Ile His Leu Asn Phe Asp His Val Pro Lys Val Leu Pro Glu Pro
    275                 280                 285

Gly Ser Lys Met Asp Ile Gln Asn Asp Ala Gln Pro Asn His Asp Leu
290                 295                 300

Glu Asn Cys Pro Asn Thr Lys Thr Asn Thr Cys Asn Asn Asp His
305                 310                 315                 320

His Asn Asp Asp Ser Ile Asn Leu Asp Tyr Asp His Glu Lys Ala Leu
                325                 330                 335

Tyr Glu Leu Asp Arg Asn Met Gln Leu Asp Gln Glu Lys Asn Asp Glu
            340                 345                 350

Lys Asn Val Asp Lys Ser Ala Asp Lys Asn Val Cys Asn Lys Asp Ile
    355                 360                 365

Ser Leu Glu Asp Lys Asn Gln His Asn Asn Asn Asn Asn Asn Asp
    370                 375                 380
```

Asp Asp Asp Gly Val Asp Ile Gln Ala Asp Thr Ser Thr Asn Val
385                 390                 395                 400

Ala Asp Gln Asn Asn Ser Val Pro Thr Asn Leu Lys Glu Asn Glu
            405                 410                 415

Glu Glu Ser Leu Asn Asp Gln Asn Glu Asn Lys Asp Glu Thr Ser
        420                 425                 430

Gln Asp Glu Asn Ile Thr Asp Glu Lys Lys Lys Lys Phe Tyr Leu
            435                 440                 445

Cys Tyr Asp Ile Glu Trp Leu Ala Ile Val Lys Ala Asn His His Leu
        450                 455                 460

Ile Ser Ala Ser Cys Asp Pro Thr Lys Glu Asp Phe Asp Phe Val Glu
465                 470                 475                 480

Asn Lys Leu Lys Glu Leu Asp Asn Lys Ile Thr Ile Lys Gly Lys Asp
            485                 490                 495

Tyr Tyr Cys Val Asn Gly Tyr Asn Thr Pro Asn Tyr Lys Asn Leu Gln
            500                 505                 510

Glu Gln Arg Gln Leu Phe Leu Lys Arg Phe Glu Leu Glu Glu Leu Ser
            515                 520                 525

Ile Tyr Thr Glu Ser Glu Leu Asn Phe Phe Ala Glu Glu Met Lys Thr
            530                 535                 540

Leu Glu Lys Met Asn Thr Asp Ile His Asn Glu Glu Asp Lys Asn Glu
545                 550                 555                 560

Cys Thr Ile Glu Ala
            565

<210> SEQ ID NO 62
<211> LENGTH: 496
<212> TYPE: PRT
<213> ORGANISM: Toxoplasma gondii

<400> SEQUENCE: 62

Met Lys Ile Ala Ile Glu Gly Cys Cys His Gly Glu Leu Asp Ala Ile
1               5                   10                  15

Tyr Ser Ser Leu Ala Arg Leu Glu Glu Met His Lys Met Lys Val Asp
            20                  25                  30

Leu Leu Ile Cys Cys Gly Asp Phe Gln Cys Val Arg Asp Ser Asn Asp
        35                  40                  45

Leu Gln Phe Leu Ala Cys Pro Pro Lys Tyr Arg Asp Leu Arg Asp Phe
    50                  55                  60

Pro Ala Tyr Phe Arg Gly Glu Lys Glu Ala Pro Cys Leu Thr Val Phe
65                  70                  75                  80

Val Gly Gly Asn His Glu Ala Pro Thr Val Leu Arg Glu Leu Tyr Tyr
                85                  90                  95

Gly Gly Trp Val Ala Pro Lys Ile Phe Tyr Leu Gly His Ala Gly Val
            100                 105                 110

Val Asn Val Gly Gly Val Arg Ile Ala Gly Leu Ser Gly Ile Phe Lys
        115                 120                 125

Ser Gln Asp Tyr Arg Lys Gly Tyr Phe Glu Arg Pro Pro Tyr Thr Glu
    130                 135                 140

Asp Thr Met Arg Ser Ala Tyr His Val Arg Glu Phe Gly Ile Ala Lys
145                 150                 155                 160

Leu Ser Glu Leu Thr Gly Arg Val Asp Ile Val Val Thr His Asp Trp
                165                 170                 175

Pro Glu Gly Ile Tyr Asp Phe Gly Asp Lys Thr Glu Leu Ile Arg Gln
            180                 185                 190

```
Lys Pro Phe Leu Glu Lys Asp Ile Gln Ala His Glu Leu Gly Asn Pro
            195                 200                 205

His Ser Met Glu Leu Leu Lys Lys Leu Lys Pro Ala Phe Trp Phe Ala
    210                 215                 220

Ala His Leu His Thr Arg Phe Ala Ala Val Tyr Val His Pro Gly Pro
225                 230                 235                 240

Glu Gly Lys Ala Thr Arg Phe Leu Ala Leu Asp Lys Val Leu Pro Arg
                245                 250                 255

Arg Glu Phe Leu Gln Ile Leu Glu Val Glu Pro Leu Leu Pro Ala Gly
                260                 265                 270

Tyr Val Gln Gln Leu Ser Pro Gly Ile Ser Arg Arg Ser Pro Thr Leu
                275                 280                 285

Cys Tyr Asp Glu Glu Trp Leu Ala Ile Leu Arg Ala Asn Gln Gln Val
                290                 295                 300

Leu Pro Val Ser Arg Phe Pro Gln Lys Ser Cys Leu Val Thr Lys Ala
305                 310                 315                 320

Thr Ala Asp Asp Leu Ala Thr Val Lys Lys Asn Leu Ala Ser Leu Gly
                325                 330                 335

Leu Arg Asn Tyr Arg Glu Thr Ser Ser Pro Lys Arg Leu Ser Leu Asn
                340                 345                 350

Ser Val Gly Ala Ala Ala Ala Glu Asp Ala Arg Arg Glu Ser Asp
                355                 360                 365

Gly Asp Arg Arg Ser Ala Arg Glu Glu Lys Glu Gly Cys Glu Glu Ala
                370                 375                 380

Ala Ala Gly Val Ser Ala Gly Ala Ser Val Gln Arg Thr Asp Val Ala
385                 390                 395                 400

Ala Glu Thr Pro Pro Gln Pro Gln Gly Gly Gln Glu Glu Ser Thr Val
                405                 410                 415

Phe Glu Trp Ile Asn Trp Ala Asp Pro Arg Ala Pro Tyr Thr Glu Leu
                420                 425                 430

Lys Glu Gln Arg Leu Phe Leu Leu Arg Asn Ile Leu Gly Phe Asp Glu
                435                 440                 445

Ala Asp Asp Lys Phe Gly Glu Ala Arg Gln Arg Glu Ala Ala Asp Val
                450                 455                 460

Asp Val Pro Val Asp Trp Thr Ser Gly His Val Asp Pro Gln Arg Thr
465                 470                 475                 480

Thr Glu Glu Val Asp Ile Cys Leu Asp Leu Ser Asp Glu Thr Ala
                485                 490                 495

<210> SEQ ID NO 63
<211> LENGTH: 521
<212> TYPE: PRT
<213> ORGANISM: Trypanosoma brucei

<400> SEQUENCE: 63

Met Ser Ser Leu Val His His Phe Phe Asn Val Lys Gly Gly Val Thr
1               5                   10                  15

Glu Arg Thr Ala Pro Ser Ser Ser Gly Gly Ala Thr Glu Thr Phe Ala
                20                  25                  30

Asn Leu His Val Ala Val Val Gly Cys Cys His Gly Glu Leu Asp Lys
                35                  40                  45

Ile Tyr Leu Ala Cys Ser Asp His Glu Val Ser Ser Gly Lys Lys Ile
            50                  55                  60

Asp Phe Val Ile Cys Ala Gly Asp Phe Gln Ala Leu Arg Arg Glu Glu
```

-continued

```
            65                  70                  75                  80
Asp Leu Lys Cys Met Ala Val Pro Glu Lys Tyr Arg Ser Leu Gly Asp
                    85                  90                  95
Phe Val Lys Tyr Tyr Gln Gly Glu Lys Arg Ala Pro Tyr Leu Thr Leu
                100                 105                 110
Phe Val Gly Asn His Glu Cys Ser Asp Trp Leu Ala Glu Glu Ser
                115                 120                 125
Tyr Gly Gly Phe Leu Ala Pro Asn Ile Tyr Tyr Leu Gly His Ser Gly
                130                 135                 140
Val Val Val Val Asp Gly Cys Ile Thr Val Ala Gly Ile Ser Gly Ile
145                 150                 155                 160
Phe Lys Ala His Asp Tyr Val Arg Pro Tyr Pro Asn Arg Pro Phe His
                165                 170                 175
Val Ser Glu Ala Ser Lys Arg Ser Ala Tyr His Val Arg Arg Ile Glu
                180                 185                 190
Val Glu Lys Leu Arg Ala Phe Val Arg Ala Leu Arg His Met Gln Gln
                195                 200                 205
Trp Gly Arg Lys Trp Gly Ala Gln Ser Val Ser Pro Leu Ala Thr Ala
210                 215                 220
Ala Asn Ile Ala Asn Pro Ala Gln Lys Val Ser Gln Asp Gly Gly Asn
225                 230                 235                 240
Asp Thr Thr Asn Ser His Ile Thr Leu Pro Pro Val Asp Ile Phe Val
                245                 250                 255
Ser His Asp Trp Pro Thr Gly Val Thr Lys Tyr Gly Asp Glu Glu Gln
                260                 265                 270
Leu Leu Arg Tyr Lys Pro Tyr Phe Arg Glu Asp Ile Arg His Gly Val
                275                 280                 285
Leu Gly Asn Pro His Thr Val Lys Leu Leu Gln Asp Ile Lys Pro Arg
                290                 295                 300
Tyr Trp Ile Ala Ala His Leu His Cys Arg Phe Glu Ala Thr Val Pro
305                 310                 315                 320
His Glu Asn Thr Ser Gly Lys Cys Thr Thr Ala Gly Thr Thr Ser Pro
                325                 330                 335
Val Ala Thr Gln Gln Lys Thr Lys Phe Leu Ala Leu Asp Lys Pro Ala
                340                 345                 350
Lys Gly Lys Gly Phe Ile Asp Phe Ile Asp Val Pro Gly Glu Arg Gly
                355                 360                 365
Ala Val Gly Arg Lys Ser Asp Val Asp Arg Val His His Pro Leu
                370                 375                 380
Trp Leu Arg Val Leu Arg Glu Ser His Asn Tyr Leu Ser Ala Asn Asp
385                 390                 395                 400
Asp Ser Trp Ser Ser Glu Thr Cys Asn Phe Leu Gln Ser Ser Glu Glu
                405                 410                 415
Glu Pro Ile Ser Thr Glu Val Ser Ile Pro Ala His Ser Thr Lys Gln
                420                 425                 430
Leu Leu Gln Ser Leu Gly Leu Pro Pro Ser Pro Ile Gln Gln Ala Gln
                435                 440                 445
Pro Gln Ser Thr Ile Ala Val Ala Gly Gly Ser Gly His His
                450                 455                 460
Arg Pro Val Thr Gly Ser Gly His Ala Lys Leu Asp Asp Lys Ala Gly
465                 470                 475                 480
Ala Pro Asp Ala Asn Cys Ser Ser Val Ala Thr Arg Pro Ala Asp Trp
                485                 490                 495
```

```
Asn Gly Ala Arg Thr Glu Asp Gly Val Asp Ala Gly Asn Asp Leu Pro
                500                 505                 510

Trp Val Glu Asp Ala Val Gly Asp Val
        515                 520
```

<210> SEQ ID NO 64
<211> LENGTH: 503
<212> TYPE: PRT
<213> ORGANISM: Trypanosoma cruzi

<400> SEQUENCE: 64

```
Met Cys Phe Val Val Val Phe Ala Val Phe Leu Leu Leu Pro
1               5                   10                  15

Trp Val Pro Met Cys Gly Val Val Cys Pro His Tyr Ser Ser Phe Phe
                20                  25                  30

Phe Val Arg Phe Val Phe Tyr Tyr Arg Leu Ser Gly Gly Lys Gly Cys
            35                  40                  45

Arg Phe Val Leu Tyr Lys Met Ser Leu Val His Phe Phe His Val
        50                  55                  60

Lys Gly Gly Val Thr Thr Asn Thr Ala Lys Asn Asn Thr Gly Ser Ser
65                  70                  75                  80

Asp Ser Gly Thr Ala Ala Glu Thr Ile His Val Ala Val Gln Gly Cys
                85                  90                  95

Cys His Gly Glu Leu Asp Arg Ile Tyr Ala Ala Cys Ala Ala His Glu
            100                 105                 110

Lys Ala Thr Gly Arg Arg Ile Glu Phe Leu Leu Cys Cys Gly Asp Phe
        115                 120                 125

Gln Ala Val Arg Asp Glu Val Asp Leu Arg Ser Met Ala Val Pro Gln
130                 135                 140

Lys Tyr Cys Val Leu Gly Asp Phe Leu Ala Tyr His Arg Arg Glu Lys
145                 150                 155                 160

His Ala Pro Tyr Leu Thr Leu Phe Val Gly Gly Asn His Glu Gly Ser
                165                 170                 175

Asp Trp Leu Ala Thr Glu Cys Tyr Gly Gly Phe Leu Ala Pro Asn Ile
            180                 185                 190

Tyr Tyr Ile Gly His Ser Gly Ala Val Ile Val Asp Asp Cys Val Thr
        195                 200                 205

Val Ala Gly Leu Ser Gly Ile Phe Lys Gly His Asp Tyr Ala Arg Pro
210                 215                 220

Tyr Pro Gly Arg Pro Phe His Ala Ser Glu Ala Ala Lys Arg Ser Ala
225                 230                 235                 240

Tyr His Val Arg Arg Ile Glu Val Glu Lys Leu Arg Ala Phe Ser Gln
                245                 250                 255

Ala Leu Glu Arg Met Arg Gln Pro Ala Ser Ser Pro Met Thr Ala Ser
            260                 265                 270

Met Ala Gly Pro Gly Ala Ser Pro Ser Arg Cys Ala Gly Glu Phe Pro
        275                 280                 285

His Ile Asp Leu Phe Leu Ser His Asp Trp Pro Ala Gly Ile Thr Lys
290                 295                 300

Tyr Gly Asp Glu Thr Gln Leu Leu Arg Tyr Lys Pro Phe Phe Glu Glu
305                 310                 315                 320

Asp Ile Arg His Gly Ala Leu Gly Asn Pro His Thr Met Thr Leu Leu
                325                 330                 335

Arg Ala Val Lys Pro Arg Tyr Trp Leu Ala Ala His Leu His Cys Gln
```

```
                  340             345             350
Phe Glu Ala Thr Ile Pro His His Asp Val Glu Asn Asp Ala Ala Ala
            355                 360                 365

Ala Gly Val Pro Arg Ala Thr Lys Phe Leu Ala Leu Asp Lys Cys Ser
370                 375                 380

Lys Gly Lys Gly Phe Ile Asp Phe Ile Asp Val Arg Val Ser Arg Gly
385                 390                 395                 400

Pro His Leu Thr Lys Glu Lys Asn Arg Glu Arg Thr Ala Arg Glu Gln
            405                 410                 415

Glu Arg Val Val His His Pro Leu Trp Leu Glu Val Leu Arg Glu Thr
        420                 425                 430

His Gly Phe Leu Thr Ser Asn Asn Asn Glu Trp Ser Ala Gly Ser Cys
    435                 440                 445

Ala Leu Leu Arg Leu Thr Pro Asp Glu Leu Arg Gln Arg Gly Val Trp
450                 455                 460

Leu Leu Ala Arg Ser Thr Ala Ser Val Leu Glu Ala Leu Val Leu Pro
465                 470                 475                 480

Pro Ala Pro Leu Gln Arg Pro Ser Ala Glu Gly Glu Trp Arg Arg Arg
            485                 490                 495

Arg Thr His Ala Ser Ala Leu
            500

<210> SEQ ID NO 65
<211> LENGTH: 620
<212> TYPE: PRT
<213> ORGANISM: Leishmania donovani

<400> SEQUENCE: 65

Met Ser Leu Ala His Lys Ile Phe Ala Thr Leu Lys Ala Ser Gly Asp
1               5                   10                  15

Gly Thr Phe Pro Ser Pro Ala Ala Pro Thr Ser Gly Gln Ser Glu Thr
            20                  25                  30

Ala Thr Thr Thr Ser Ala Ser Pro Ser Gly Ser Trp Asn Glu Arg Phe
        35                  40                  45

Tyr His Ile Ala Val Gln Gly Cys Cys His Gly Glu Leu Asp Arg Ile
    50                  55                  60

Tyr Asp Ser Cys Ser Glu His Glu Arg Gln Thr Gly Lys Arg Ile Asp
65                  70                  75                  80

Val Leu Leu Cys Cys Gly Asp Phe Gln Ala Val Arg Thr Ala Arg Asp
                85                  90                  95

Met Asp Ser Met Ala Val Pro Asp Lys Tyr Lys Val Leu Gly Asp Phe
            100                 105                 110

His Lys Tyr Tyr Ala Asp Val Ser Gly Ala Phe Thr Gly His Lys Ala
        115                 120                 125

Gln Thr Leu Ala Pro Tyr Leu Thr Ile Phe Val Gly Gly Asn His Glu
    130                 135                 140

Asn Ser Asp Leu Leu Ala Gln Glu Ser Tyr Gly Gly Phe Val Ala Pro
145                 150                 155                 160

Asn Val Phe Tyr Leu Gly His Ser Ser Val Val Thr Val Asp Asp Cys
                165                 170                 175

Leu Thr Ile Ala Gly Leu Ser Gly Ile Phe Lys Asp Pro Asp Tyr Asp
            180                 185                 190

Arg Pro Tyr Pro Pro Arg Pro Tyr Ala Val Asn Pro Val Ala Lys Lys
        195                 200                 205
```

```
Ser Ala Tyr His Val Arg Arg Ile Glu Val Ala Lys Leu His Ala Tyr
    210             215                 220
Leu Arg Ala Thr Gln Lys Ile Arg Ser Asn Ser Thr Ile Glu Ala Ala
225             230                 235                 240
Lys Thr Thr Ser Ala Thr Ser Pro Ala Ala Ser Pro Pro Met Val Asp
                245                 250                 255
Leu Phe Leu Ser His Asp Trp Pro Val Gly Ile Thr Gly Tyr Gly Asp
            260                 265                 270
Glu Ala Gln Leu Leu Arg Phe Lys Pro Tyr Phe Lys Asp Asp Ile Arg
        275                 280                 285
Arg His Ala Leu Gly Asn Pro Tyr Thr Met Arg Leu Leu Gln Glu Ala
    290                 295                 300
Lys Ala Pro Tyr Trp Phe Ala Ala His Leu His Cys Tyr Phe Glu Ala
305             310                 315                 320
Thr Val Glu His Pro Ser Ala Gly Ala Thr Glu Met Ala Ala Thr
                325                 330                 335
Ala Ala Ala Ser Thr Lys Phe Val Ala Leu Asp Lys Cys Ala Lys Gly
            340                 345                 350
His Gly Phe Leu Thr Phe Ile Asp Leu Pro Arg Val Arg Arg Gly Gly
        355                 360                 365
Val Arg Ala Ala Pro Pro Ser Glu Ser His Pro His Gly Thr Ala Thr
    370                 375                 380
Val Leu Gly Thr Ser Arg Ile Arg Arg Asp Pro Val Trp Leu Glu Val
385             390                 395                 400
Leu Arg Val Ser His Gln Phe Val Ala Ala Asn Arg Thr Val Glu Ala
                405                 410                 415
Gly Leu Gly Gly Gly Gly Phe Asp Val Asp Glu Ala Val Lys Glu Val
            420                 425                 430
Val Ala Ser Tyr Arg Ser Ala Thr Arg Pro Ser Ala Ala Ala Leu Leu
        435                 440                 445
Ala Pro Thr Thr Glu Thr Leu Leu Ala Ala Leu Gln Leu Ser Pro Ala
    450                 455                 460
Leu Pro Leu Gln Gln Met Ala Pro Ala Ala Ser Pro Glu Ser Pro
465                 470                 475                 480
Thr Lys Gly Ala Asp Gly Arg Ala Ser Pro Ser Ala Thr Arg Arg Asp
                485                 490                 495
Glu Thr Val Trp Gln Asn Arg Asn Ser Thr Arg Cys Ile Gly Gly Ser
            500                 505                 510
Leu Gln Pro His His Pro Arg Ala Arg Thr Glu Ala Thr Arg Ala Ser
        515                 520                 525
Ser Val Ser Thr Ala Ala Pro Lys Ser Ser Thr Pro Leu Trp Tyr Thr
    530                 535                 540
Ala Gly Thr Gln Pro Leu Gln Gln Pro Pro Thr Ser Ala Leu Arg Ile
545                 550                 555                 560
Phe Glu Asp Val Gly Pro Thr Gly Cys Ser Ser Ala Pro Ser Ser Thr
                565                 570                 575
Ser Gly Met Val Ala Gly His Val Ser Ser Ser Phe Ala Cys Thr Asp
            580                 585                 590
Gly Asp Gly Gly Ala Pro Pro Arg Glu Pro Ala Ala Thr Thr Leu Ser
        595                 600                 605
Trp Phe Glu Asp Thr Thr Gln Gln Gln Gln Ser
610                 615                 620
```

```
<210> SEQ ID NO 66
<211> LENGTH: 369
<212> TYPE: PRT
<213> ORGANISM: Cryptosporidium parvum

<400> SEQUENCE: 66
```

| | | | | | | | | | | | | | | |
|---|---|---|---|---|---|---|---|---|---|---|---|---|---|---|
| Val | Ala | Val | Ile | Gly | Cys | Cys | His | Gly | Glu | Leu | Asn | Arg | Leu | Tyr | Met |
| 1 | | | | 5 | | | | | 10 | | | | | 15 | |

Glu Val Glu Lys Tyr Glu Asn Glu Lys Asn Glu Lys Val Asp Leu Ile
            20                  25                  30

Leu Cys Cys Gly Asp Met Gln Thr Ile Arg Asp Glu Asn Asp Leu Gln
        35                  40                  45

Asp Met Ala Val Lys Ser His Arg Ser Lys Lys Gly Asp Phe Trp Glu
    50                  55                  60

Tyr Tyr Glu Gly Leu Lys Lys Ala Pro Lys Leu Thr Ile Phe Ile Gly
65                  70                  75                  80

Gly Asn His Glu Thr Pro Asn Val Leu Ile Pro Leu Tyr Tyr Gly Gly
                85                  90                  95

Trp Val Ala Pro Asn Ile Phe Tyr Leu Gly Ser Ser Gly Val Ile Arg
            100                 105                 110

Val Gly Asp Val Arg Val Ala Gly Ile Ser Gly Ile Tyr Lys Asn Tyr
        115                 120                 125

Asp His Phe Arg Gly Tyr Tyr Glu Ser Lys Pro Phe Thr Glu Glu Ser
    130                 135                 140

Lys Arg Ser Trp Tyr His Ile Arg Trp Leu Glu Ile Gln Lys Leu Leu
145                 150                 155                 160

Leu Ile Glu Asn Ile Lys Ser Asn Phe Leu Gly Ser Thr Glu Ser Arg
                165                 170                 175

Lys Val Asp Val Met Ile Ser His Asp Trp Pro Asn Gly Ile Glu Arg
            180                 185                 190

Phe Gly Asn Leu Asn Tyr Leu Ile Arg Arg Lys Pro Tyr Leu Lys Glu
        195                 200                 205

Asp Ile Glu Leu Gly Arg Leu Gly Ile Pro Gly Cys Ile Glu Leu Ile
    210                 215                 220

Glu His Leu Arg Pro Thr Phe Trp Phe Ser Gly His His Cys Phe
225                 230                 235                 240

Phe Asp Ala Ser Ile Glu Phe Glu Asn Gln Leu Tyr Ser Ser Glu Phe
                245                 250                 255

Arg Ala Ile Asp Lys Phe Lys Asn Ser Asn Ser Pro Val Arg Tyr Phe
            260                 265                 270

Asp Ile Asn Ser Asn Lys Asn Asp Val Arg Ile Tyr Leu Asp Phe Glu
        275                 280                 285

Trp Leu Thr Ile Leu Arg Ser Val Lys Ala Asn Ile Pro Lys Gly Asn
    290                 295                 300

Phe Thr Ile Asp Lys Asn Ser Ile Pro Lys Leu Ser Gly Pro Thr Lys
305                 310                 315                 320

Ser Asp Ile Asp Ala Ile Tyr Lys Asn Leu Lys Glu Val Ile Gly Asp
                325                 330                 335

Phe Asp Glu Asn His Tyr Glu Trp Pro Leu Trp Gly Gln Ala Asn Gly
            340                 345                 350

Asn Phe Lys Asn Leu Gln Asp Gln Tyr Asn Phe Ile Asn Arg Ile Ile
        355                 360                 365

Glu

```
<210> SEQ ID NO 67
<211> LENGTH: 304
<212> TYPE: PRT
<213> ORGANISM: Saccharomyces cerevisiae
<220> FEATURE:
<221> NAME/KEY: MISC_FEATURE
<223> OTHER INFORMATION: X = any amino acid
<220> FEATURE:
<221> NAME/KEY: misc_feature
<222> LOCATION: (16)..(24)
<223> OTHER INFORMATION: Xaa can be any naturally occurring amino acid
<220> FEATURE:
<221> NAME/KEY: misc_feature
<222> LOCATION: (56)..(58)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid
<220> FEATURE:
<221> NAME/KEY: misc_feature
<222> LOCATION: (165)..(167)
<223> OTHER INFORMATION: Xaa can be any naturally occurring amino acid
<220> FEATURE:
<221> NAME/KEY: misc_feature
<222> LOCATION: (200)..(204)
<223> OTHER INFORMATION: Xaa can be any naturally occurring amino acid
<220> FEATURE:
<221> NAME/KEY: misc_feature
<222> LOCATION: (234)..(286)
<223> OTHER INFORMATION: Xaa can be any naturally occurring amino acid

<400> SEQUENCE: 67

Ile Ala Val Gln Gly Cys Cys His Gly Gln Leu Asn Gln Ile Tyr Xaa
1               5                   10                  15

Xaa Xaa Xaa Xaa Xaa Xaa Xaa Thr Pro Ile Asp Leu Leu Ile Ile
            20                  25                  30

Leu Gly Asp Phe Gln Ser Ile Arg Asp Gly Gln Asp Phe Lys Ser Ile
            35                  40                  45

Ala Ile Pro Pro Lys Tyr Gln Xaa Xaa Xaa Asp Phe Ile Ser Tyr Tyr
50                  55                  60

Asn Asn Glu Ile Glu Ala Pro Val Pro Thr Ile Phe Ile Gly Gly Asn
65                  70                  75                  80

His Glu Ser Met Arg His Leu Met Leu Leu Pro His Gly Gly Tyr Val
                85                  90                  95

Ala Lys Asn Ile Phe Tyr Met Gly Tyr Ser Asn Val Ile Trp Phe Lys
            100                 105                 110

Gly Ile Arg Ile Gly Ser Leu Ser Gly Ile Trp Lys Glu Trp Asp Phe
            115                 120                 125

Xaa Xaa Xaa Xaa Xaa Xaa Xaa Asn Asp Leu Glu Asn Asn Trp Lys
    130                 135                 140

Ala Asn Ile Arg Asn Leu Tyr His Val Arg Ile Ser Asp Ile Ala Pro
145                 150                 155                 160

Leu Phe Met Ile Xaa Xaa Xaa Ile Asp Ile Met Leu Ser His Asp Trp
                165                 170                 175

Pro Asn Gly Val Val Tyr His Gly Asp Thr Lys His Leu Leu Lys Leu
            180                 185                 190

Lys Pro Phe Phe Glu Gln Asp Xaa Xaa Xaa Xaa Xaa Leu Gly Ser Pro
            195                 200                 205

Val Thr Trp Gln Leu Leu Arg Asp Leu Arg Pro Gln Trp Trp Leu Ser
            210                 215                 220

Ala His Leu His Val Arg Phe Met Ala Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Gly Glu
            275                 280                 285

Thr Arg Phe Leu Ala Leu Asp Lys Cys Leu Pro Arg Arg Arg Trp Leu
            290                 295                 300
```